(12) United States Patent
Himmelsbach et al.

(10) Patent No.: US 8,772,298 B2
(45) Date of Patent: Jul. 8, 2014

(54) SPIROCYCLIC HETEROCYCLES MEDICAMENTS CONTAINING SAID COMPOUNDS, USE THEREOF AND METHOD FOR THEIR PRODUCTION

(71) Applicants: Frank Himmelsbach, Mittelbiberach (DE); Birgit Jung, Laupheim (DE); Ralf Lotz, Schemmerhofen (DE)

(72) Inventors: Frank Himmelsbach, Mittelbiberach (DE); Birgit Jung, Laupheim (DE); Ralf Lotz, Schemmerhofen (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/920,389

(22) Filed: Jun. 18, 2013

(65) Prior Publication Data
US 2013/0281461 A1 Oct. 24, 2013

Related U.S. Application Data

(62) Division of application No. 12/865,431, filed as application No. PCT/EP2009/000805 on Feb. 5, 2009, now Pat. No. 8,497,369.

(30) Foreign Application Priority Data

Feb. 7, 2008 (EP) .................................. 08101353

(51) Int. Cl.
*A61K 31/497* (2006.01)
*A61K 31/517* (2006.01)

(52) U.S. Cl.
USPC ................................ 514/252.17; 514/266.23

(58) Field of Classification Search
USPC ........................................ 514/252.17, 266.23
See application file for complete search history.

(56) References Cited

U.S. PATENT DOCUMENTS

| | | | |
|---|---|---|---|
| 3,985,749 A | 10/1976 | Foster | |
| 4,322,420 A | 3/1982 | Kobayashi et al. | |
| 4,335,127 A | 6/1982 | Vandenberk et al. | |
| 4,640,920 A | 2/1987 | Boyle et al. | |
| 4,845,629 A | 7/1989 | Murga | |
| 4,921,863 A | 5/1990 | Sugimoto et al. | |
| 5,064,833 A | 11/1991 | Ife et al. | |
| 5,252,586 A | 10/1993 | Cain et al. | |
| 5,457,105 A | 10/1995 | Barker | |
| 5,616,582 A | 4/1997 | Barker | |
| 5,642,285 A | 6/1997 | Woo et al. | |
| 5,721,237 A | 2/1998 | Myers et al. | |
| 5,747,498 A | 5/1998 | Schnur et al. | |
| 5,760,041 A | 6/1998 | Wissner et al. | |
| 5,770,599 A | 6/1998 | Gibson | |
| 5,770,603 A | 6/1998 | Gibson | |
| 5,821,246 A | 10/1998 | Brown et al. | |
| 5,866,572 A | 2/1999 | Barker et al. | |
| 5,929,080 A | 7/1999 | Frost | |
| 5,938,706 A | 8/1999 | Feldman | |
| 5,962,458 A | 10/1999 | Lohmann et al. | |
| 6,004,967 A | 12/1999 | McMahon et al. | |
| 6,046,206 A | 4/2000 | Pamukcu et al. | |
| 6,117,433 A | 9/2000 | Edens et al. | |
| 6,126,917 A | 10/2000 | Mishani et al. | |
| 6,177,433 B1 | 1/2001 | Uckun et al. | |
| 6,225,318 B1 | 5/2001 | Sobolov-Jaynes et al. | |
| 6,270,747 B1 | 8/2001 | Nadel et al. | |
| 6,297,258 B1 | 10/2001 | Wissner et al. | |
| 6,313,130 B1 | 11/2001 | Uckun et al. | |
| 6,326,373 B1 | 12/2001 | Uckun et al. | |
| 6,362,336 B1 | 3/2002 | Lohmann et al. | |
| 6,384,223 B1 | 5/2002 | Gletsos | |
| 6,399,602 B1 | 6/2002 | Barker et al. | |
| 6,403,580 B1 | 6/2002 | Himmelsbach et al. | |
| 6,414,148 B1 | 7/2002 | Thomas et al. | |

(Continued)

FOREIGN PATENT DOCUMENTS

| | | |
|---|---|---|
| CA | 2417897 A1 | 1/2003 |
| CA | 2476008 A1 | 10/2003 |

(Continued)

OTHER PUBLICATIONS

B.C. Baguley et al.: "Inhibition of growth of primary human tumor cell cultures by a 4-anilinoquinaziline inhibitor of the epidermal growth factor receptor family of tyrosine kinase", European Journal of Cancer, 1998, vol. 34, No. 7, pp. 1086-1090.

(Continued)

*Primary Examiner* — Jeffrey H Murray
*Assistant Examiner* — Oluwafemi Masha
(74) *Attorney, Agent, or Firm* — Michael P. Morris; Edward S. Lazer; Edouard G. Lebel

(57) ABSTRACT

The present invention relates to spirocyclic heterocycles of general formula (I)

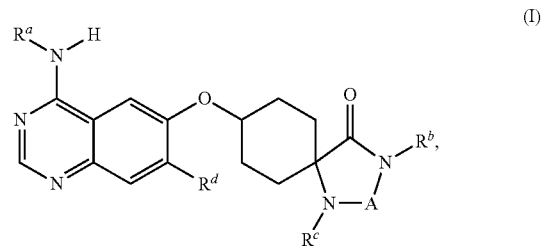

the tautomers, the stereoisomers, the mixtures thereof and the salts thereof, particularly the physiologically acceptable salts thereof with inorganic or organic acids, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways, and the preparation thereof.

9 Claims, No Drawings

(56) References Cited

U.S. PATENT DOCUMENTS

| | | |
|---|---|---|
| 6,551,989 B2 | 4/2003 | Nadel et al. |
| 6,562,319 B2 | 5/2003 | Mishani et al. |
| 6,566,324 B2 | 5/2003 | Nadel et al. |
| 6,617,329 B2 | 9/2003 | Himmelsbach et al. |
| 6,627,634 B2 | 9/2003 | Himmelsbach et al. |
| 6,645,969 B1 | 11/2003 | Myers et al. |
| 6,653,305 B2 | 11/2003 | Himmelsbach et al. |
| 6,656,946 B2 | 12/2003 | Himmelsbach et al. |
| 6,740,651 B2 | 5/2004 | Himmelsbach et al. |
| 6,846,799 B1 | 1/2005 | Nadel et al. |
| 6,924,285 B2 | 8/2005 | Himmelsbach et al. |
| 6,972,288 B1 | 12/2005 | Himmelsbach et al. |
| 7,081,461 B1 | 7/2006 | Mortlock et al. |
| 7,119,084 B2 | 10/2006 | Himmelsbach et al. |
| 7,196,091 B2 | 3/2007 | Himmelsbach et al. |
| 7,354,894 B2 | 4/2008 | Nadel et al. |
| 7,358,222 B2 | 4/2008 | Nadel et al. |
| 7,456,189 B2 | 11/2008 | Himmelsbach et al. |
| 7,531,500 B2 | 5/2009 | Nadel et al. |
| 7,700,547 B2 | 4/2010 | Nadel et al. |
| 7,910,731 B2 | 3/2011 | Himmelsbach et al. |
| 7,998,949 B2 | 8/2011 | Himmelsbach et al. |
| 2001/0036919 A1 | 11/2001 | Nadel et al. |
| 2001/0041178 A1 | 11/2001 | Nadel et al. |
| 2001/0044435 A1 | 11/2001 | Himmelsbach et al. |
| 2002/0049197 A1 | 4/2002 | Himmelsbach et al. |
| 2002/0082270 A1 | 6/2002 | Himmelsbach et al. |
| 2002/0082271 A1 | 6/2002 | Himmelsbach et al. |
| 2002/0115675 A1 | 8/2002 | Himmelsbach et al. |
| 2002/0128553 A1 | 9/2002 | Mishani et al. |
| 2002/0169180 A1 | 11/2002 | Himmelsbach et al. |
| 2002/0173509 A1 | 11/2002 | Himmelsbach et al. |
| 2002/0173646 A1 | 11/2002 | Thomas et al. |
| 2002/0177601 A1 | 11/2002 | Himmelsbach et al. |
| 2003/0148990 A1 | 8/2003 | Nadel et al. |
| 2003/0149062 A1 | 8/2003 | Jung et al. |
| 2003/0158196 A1 | 8/2003 | Jung et al. |
| 2004/0044014 A1 | 3/2004 | Himmelsbach et al. |
| 2004/0048880 A1 | 3/2004 | Himmelsbach et al. |
| 2004/0176361 A1 | 9/2004 | Fujio et al. |
| 2004/0265302 A1 | 12/2004 | Nadel et al. |
| 2005/0014772 A1 | 1/2005 | Himmelsbach et al. |
| 2005/0059661 A1 | 3/2005 | Jung et al. |
| 2005/0070560 A1 | 3/2005 | Himmelsbach et al. |
| 2005/0159436 A1 | 7/2005 | Himmelsbach et al. |
| 2005/0165035 A1 | 7/2005 | Bradbury et al. |
| 2005/0182043 A1 | 8/2005 | Himmelsbach et al. |
| 2005/0215574 A1 | 9/2005 | Bradbury et al. |
| 2006/0063752 A1 | 3/2006 | Himmelsbach et al. |
| 2006/0264450 A1 | 11/2006 | Himmelsbach et al. |
| 2006/0270672 A1 | 11/2006 | Himmelsbach et al. |
| 2007/0135463 A1 | 6/2007 | Himmelsbach et al. |
| 2007/0270330 A1 | 11/2007 | Nadel et al. |
| 2008/0103161 A1 | 5/2008 | Himmelsbach et al. |
| 2008/0175797 A1 | 7/2008 | Nadel et al. |
| 2008/0199462 A1 | 8/2008 | Nadel et al. |
| 2009/0036676 A1 | 2/2009 | Himmelsbach et al. |
| 2009/0203683 A1 | 8/2009 | Himmelsbach et al. |
| 2009/0306072 A1 | 12/2009 | Jung et al. |
| 2009/0306105 A1 | 12/2009 | Himmelsbach et al. |
| 2010/0022505 A1 | 1/2010 | Himmelsbach et al. |
| 2010/0234371 A1 | 9/2010 | Himmelsbach et al. |
| 2011/0046148 A1 | 2/2011 | Himmelsbach et al. |
| 2011/0077246 A1 | 3/2011 | Himmelsbach et al. |
| 2011/0190248 A1 | 8/2011 | Himmelsbach et al. |

FOREIGN PATENT DOCUMENTS

| | | | |
|---|---|---|---|
| CA | 2559699 A1 | 11/2005 | |
| CA | 2559669 A1 | 3/2007 | |
| CA | 2631813 A1 | 6/2007 | |
| CA | 2669187 A1 | 5/2008 | |
| DE | 10042058 A1 | 3/2002 | |
| EP | 288563 A1 | 11/1988 | |
| EP | 326330 A2 | 8/1989 | |
| EP | 520722 A1 | 12/1992 | |
| EP | 0566226 A1 | 10/1993 | |
| EP | 602851 A1 | 6/1994 | |
| EP | 607439 | 7/1994 | |
| EP | 635507 A1 | 1/1995 | |
| EP | 0787722 A1 | 8/1997 | |
| EP | 837063 A1 | 4/1998 | |
| EP | 1230919 A2 | 8/2002 | |
| EP | 1283039 A1 | 2/2003 | |
| EP | 1369418 A1 | 12/2003 | |
| GB | 2033894 A | 5/1980 | |
| GB | 2160201 A | 12/1985 | |
| GB | 2295387 A | 5/1996 | |
| JP | 11-189586 A | 7/1999 | |
| WO | 8802365 A1 | 4/1988 | |
| WO | 9214746 A1 | 9/1992 | |
| WO | 9220642 A1 | 11/1992 | |
| WO | 9308170 A1 | 4/1993 | |
| WO | 9317682 A1 | 9/1993 | |
| WO | 9427965 A1 | 12/1994 | |
| WO | 9500146 A1 | 1/1995 | |
| WO | 9503283 A1 | 2/1995 | |
| WO | 9515758 A1 | 6/1995 | |
| WO | 9519169 A2 | 7/1995 | |
| WO | 9524190 A2 | 9/1995 | |
| WO | 9609294 A1 | 3/1996 | |
| WO | 9615118 A1 | 5/1996 | |
| WO | 9616960 A1 | 6/1996 | |
| WO | 9630347 A1 | 10/1996 | |
| WO | 9633977 A1 | 10/1996 | |
| WO | 9633978 A1 | 10/1996 | |
| WO | 9633979 A1 | 10/1996 | |
| WO | 9633980 A1 | 10/1996 | |
| WO | 9633981 A1 | 10/1996 | |
| WO | 9639145 A1 | 12/1996 | |
| WO | 9703069 A1 | 1/1997 | |
| WO | 9711692 A2 | 4/1997 | |
| WO | 9718813 A1 | 5/1997 | |
| WO | 9722596 A1 | 6/1997 | |
| WO | 9730034 | 8/1997 | |
| WO | 9730035 A1 | 8/1997 | |
| WO | 9730044 A1 | 8/1997 | |
| WO | 9732856 A1 | 9/1997 | |
| WO | 9738983 A1 | 10/1997 | |
| WO | 9738994 A1 | 10/1997 | |
| WO | 9742187 A1 | 11/1997 | |
| WO | 9802434 A1 | 1/1998 | |
| WO | 9813354 A1 | 4/1998 | |
| WO | 9819649 A2 | 5/1998 | |
| WO | 9838984 A2 | 9/1998 | |
| WO | 9843960 A1 | 10/1998 | |
| WO | 9850038 A1 | 11/1998 | |
| WO | 9850370 A1 | 11/1998 | |
| WO | 9901467 A2 | 1/1999 | |
| WO | 9906378 A1 | 2/1999 | |
| WO | 9906396 A1 | 2/1999 | |
| WO | 9909016 A1 | 2/1999 | |
| WO | 9910349 A1 | 3/1999 | |
| WO | 9924037 A1 | 5/1999 | |
| WO | 9935132 A1 | 7/1999 | |
| WO | 9961428 A1 | 12/1999 | |
| WO | 0000202 A1 | 1/2000 | |
| WO | 0006555 A1 | 2/2000 | |
| WO | 0009481 A1 | 2/2000 | |
| WO | 0010981 A1 | 3/2000 | |
| WO | 0012497 A2 | 3/2000 | |
| WO | 0018740 A1 | 4/2000 | |
| WO | 0020402 A1 | 4/2000 | |
| WO | 0024718 A1 | 5/2000 | |
| WO | 0044728 A1 | 8/2000 | |
| WO | 0047212 A1 | 8/2000 | |
| WO | 0051587 A2 | 9/2000 | |
| WO | 0051991 A1 | 9/2000 | |
| WO | 0055141 A1 | 9/2000 | |
| WO | 0055162 A2 | 9/2000 | |
| WO | 0056338 A1 | 9/2000 | |
| WO | 0056720 A1 | 9/2000 | |
| WO | 0068201 A1 | 11/2000 | |

(56) References Cited

FOREIGN PATENT DOCUMENTS

| | | |
|---|---|---|
| WO | 0068203 A1 | 11/2000 |
| WO | 0073260 A1 | 12/2000 |
| WO | 0078735 A1 | 12/2000 |
| WO | 0104102 A1 | 1/2001 |
| WO | 0107432 A2 | 2/2001 |
| WO | 0112227 A1 | 2/2001 |
| WO | 0121594 A1 | 3/2001 |
| WO | 0121595 A1 | 3/2001 |
| WO | 0121596 A1 | 3/2001 |
| WO | 0121597 A1 | 3/2001 |
| WO | 0132632 A2 | 5/2001 |
| WO | 0132651 A1 | 5/2001 |
| WO | 0145641 A2 | 6/2001 |
| WO | 0166099 A2 | 9/2001 |
| WO | 0176586 A1 | 10/2001 |
| WO | 0177085 A1 | 10/2001 |
| WO | 0177104 A1 | 10/2001 |
| WO | 0194341 A1 | 12/2001 |
| WO | 0198277 A2 | 12/2001 |
| WO | 0216352 A1 | 2/2002 |
| WO | 0218351 A1 | 3/2002 |
| WO | 0218370 A1 | 3/2002 |
| WO | 0218372 A1 | 3/2002 |
| WO | 0218373 A1 | 3/2002 |
| WO | 0218376 A1 | 3/2002 |
| WO | 0224684 A1 | 3/2002 |
| WO | 0230924 A1 | 4/2002 |
| WO | 0234711 A1 | 5/2002 |
| WO | 0234744 A1 | 5/2002 |
| WO | 0241882 A2 | 5/2002 |
| WO | 0244166 A1 | 6/2002 |
| WO | 0248117 A1 | 6/2002 |
| WO | 0250043 A1 | 6/2002 |
| WO | 02056882 A1 | 7/2002 |
| WO | 02062767 A1 | 8/2002 |
| WO | 02066445 A1 | 8/2002 |
| WO | 02068409 A1 | 9/2002 |
| WO | 02073235 A2 | 9/2002 |
| WO | 02076976 A2 | 10/2002 |
| WO | 02092577 A1 | 11/2002 |
| WO | 02092578 A1 | 11/2002 |
| WO | 02092579 A1 | 11/2002 |
| WO | 02094760 A2 | 11/2002 |
| WO | 03000188 A2 | 1/2003 |
| WO | 03040108 A1 | 5/2003 |
| WO | 03040109 A2 | 5/2003 |
| WO | 03045364 A2 | 6/2003 |
| WO | 03045395 A1 | 6/2003 |
| WO | 03049740 A1 | 6/2003 |
| WO | 03072539 A1 | 9/2003 |
| WO | 03082290 A1 | 10/2003 |
| WO | 03082831 A1 | 10/2003 |
| WO | 2004064718 A2 | 8/2004 |
| WO | 2004093880 A1 | 11/2004 |
| WO | 2005012290 A1 | 2/2005 |
| WO | 2005026151 A1 | 3/2005 |
| WO | 2005026152 A1 | 3/2005 |
| WO | 2005028469 A1 | 3/2005 |
| WO | 2005028470 A1 | 3/2005 |
| WO | 2005030757 A1 | 4/2005 |
| WO | 2005030765 A1 | 4/2005 |
| WO | 2005041973 A1 | 5/2005 |
| WO | 2005048928 A2 | 6/2005 |
| WO | 2005102349 A1 | 11/2005 |
| WO | 2006008173 A2 | 1/2006 |
| WO | 2006034015 A1 | 3/2006 |
| WO | 2008055854 A1 | 5/2008 |
| WO | 2010026029 A1 | 3/2010 |

OTHER PUBLICATIONS

Ballard, Peter et al, "5-Substituted 4-anilinoquinazolines as potent, selective and orally active inhibitors of erbB2 receptor tyrosine kinase," Bioorganic & Medicinal Chemistry Letters 15(19):4226-4229 (2005).

Ballard, Peter et al, "Inhibitors of epidermal growth factor receptor tyrosine kinase: Novel C-5 substituted anilinoquinazolines designed to target the ribose pocket," Bioorganic & Medicinal Chemistry Letters 16(6):1633-1637 (2006).

Ballard, Peter et al, "Inhibitors of epidermal growth factor receptor tyrosine kinase: Optimization of potency and in vivo pharmacokinetics," Bioorganic & Medicinal Chemistry Letters 16(18):4908-4912 (2006).

Barker et al., Studies Leading to the Identification of ZD1839 (IressaTM): An Orally Active, Selective Epidermal Growth Factor Receptor Tyrosine Kinase Inhibitor Targeted to the Treatment of Cancer, Bioorg. Med. Chem. Lett. 11(14): 1911-1914 (2001).

Bridges et al. (1996) "Tyrosine kinase inhibitors. 8. An unusually steep structure-activity relationship for analogues of 4-(3-bromoanilino)-6,7-dimethoxyquinazoline (PD 153035), a potent inhibitor of the epidermal growth factor receptor" J. Med. Chem.39: 267-276.

Chevalier et al. (1999) "Induction of DNA replication by peroxisome proliferators is independent of both tumour necrosis factor (alpha) priming and EGF-receptor tyrosine kinase activity" J. Cell Sci. 112(24): 4785-4791.

Communication from EPO dated Mar. 9, 2006, in EP Appin. No. 03 710 015.3, the European counterpart of the present application.

Communication from European Patent Office ("EPO") dated May 27, 2005, in EP Appin. No. 03 710 015.3, the European counterpart of the present application.

Communication from European Patent Office in EP Appin. No. 03 710 015.3, the European counterpart of the present application, dated Sep. 22, 2006.

Denny et al., "Structure-Activity Relationships for 4-Anilinoquinazolines as Potent Inhibitors at the ATP Binding Site for the Epidermal Growth Factor Receptor in vitro," Clinical and Experimental Pharmacology and Physiology 23:424-427 (1996).

Drug Chemistry ed. E. Pawelczyk, PZWL, Wassaw, 1986, e.g. chapter 1.2.2.

English translation of Office Action in Chinese Patent Appin. No. 03811739.8, the Chinese counterpart of the present application, dated Jul. 21, 2006.

English Translation of Office Action in Japanese Patent Appin. No. 2003-580299, the Japanese counterpart of the present application, dated May 11, 2006.

English Translation of Response to Office Action in Chinese Patent Appin. No. 03811739.8, the Chinese counterpart of the present application, dated Dec. 5, 2006.

English translation of Response to Office Action in Japanese Patent Appin. No. 2003-580299, the Japanese counterpart of the present application, dated Jul. 28, 2006.

English Translation of Response to Office Action in Japanese Patent Appin. No. 2003-580299, the Japanese counterpart of the present application, dated Oct. 26, 2006.

Gazit et al. (1996) "Tyrophostins IV-Highly Potent Inhibitors . . . Relationship Study of 4-Anilidoquinazolines" Bioorganic & Medicinal Chemistry 4(8): 1203-1207.

Ghosh et al. (1999) "Structure-based design of potent inhibitors of EGF-receptor tyrosine kinase as anti-cancer agents" Anti-Cancer Drug Design 14, 403-410.

Gibson, K.H., et al.: "Epidermal growth factor receptor tyrosine kinase: Structure-activity relationships and antitumor activity of novel quinazolines", Bioorganic & Medicinal Chemistry Letters, 1997, vol. 7, No. 21, pp. 2723-2728.

Goldkorn, Tzipora, et al; EGF-Receptor Phosphorylation and Signaling Are Trageted by H2O2 Redox Stress; Am. J. Respir. Cell Mol. Biol (1998) vol. 19 pp. 786-798.

Harris, Craig et al, "Facile synthesis of 7-amino anilinoquinazolines via direct amination of the quinazoline core," Tetrahedron Letters 46(43):7381-7384 (2005).

Harris, Craig et al, "Selective alkylation of a 6,7-dihydroxyquinazoline," Tetrahedron Letters 46(45):7715-7719 (2005).

Hennequin et al. (1999) "Design and structure-activity relationship of a new class of potent VEGF receptor tyrosine kinaseinhibitors" J. Med. Chem. 42: 5369-5389.

(56) References Cited

OTHER PUBLICATIONS

Hennequin et al. (2002) "Novel 4-anilinoquinazolines with C-7 basic side chains. Design and structure activity relationship of a series of potent, orally active, VEGF receptor tyrosine kinase inhibitors" J. Med. Chem. 45: 1300-1312.
Hennequin, Laurent et al, "Novel 4-anilinoquinazolines with C-6 carbon-linked side Synthesis and structure-activity relationship of a series of potent, orally active, EGF receptor tyrosine kinase inhibitors," Bioorganic & Medicinal Chemistry Letters 16(10):2672-2676 (2006).
International Search Report for PCT/EP2004/010723 mailed Mar. 10, 2005.
International Search Report for PCT/EP2006/065000 mailed Feb. 6, 2007.
International Search Report for PCT/EP2006/068598 mailed Mar. 6, 2007.
International Search Report for PCT/EP2007/061842 mailed Apr. 10, 2008.
International Search Report for PCT/EP2008/051141 mailed Jul. 11, 2008.
International Search Report for PCT/EP2009/000805 mailed May 9, 2009.
International Search Report for PCT/EP2009/059511 mailed Sep. 18, 2009.
International Search Report for PCT/EP2009/059519 mailed Sep. 18, 2009.
International Search Report PCT/EP2003/03062 mailed Jun. 6, 2003.
International Search report, PCT/EP/00/02228, Jul. 18, 2000.
International Search Report, UAE/P/209/2001, Apr. 20, 2010.
Mendelsohn (2002) "Targeting the Epidermal Growth Factor Receptor for Cancer Therapy" Journal of Clinical Oncology 20(18s): 2s-13s.
Mendelsohn et al. (2003) "Status of Epidermal Growth Factor Receptor Antagonists in the Biology and Treatment of Cancer" Journal of Clinical Oncology 21(14): 2787-2799.
Myers et al. (1997) "The preparation and SAR of 4-(anilino), 4-(phenoxy), and 4-(thiophenoxy)-quinazolines: inhibitors of p56lck and EGF-R tyrosine kinase activity" Bioorg. Med. Chem. Lett. 7(4): 417-420.
Notices of Allowability and Allowance dated Jul. 26, 2006, in copending U.S. Appl. No. 10/857,342.
Office Action in Indian Patent Appin. No. 2630/DELNP/2004, the Indian counterpart of the present application, dated Apr. 20, 2006.
Pao et al. (2005) "Epidermal Growth Factor Receptor Mutations, Small-Molecule Kinase Inhibitors, and Non-Small-Cell Lung Cancer: Current Knowledge and Future Directions" Journal of Clinical Oncology 23(11):1-13.
Pending U.S. Appl. No. 11/487,727, filed Aug. 2, 2006.
Rama Krishna Narla et al.: "4-(3'-Bromo-4'hyroxyphenyl)-amino-6,7-dimethoxyquinazoline: A novel quinazoline derivative with potent cytotoxic activity against human glioblastoma cells", Clinical cancer research,. Jun. 1998, vol. 4, pp. 1405-1414.
Reply to May 27, 2005, Communication from EPO dated Sep. 20, 2005.
Response to Office Action in Chinese Patent Appin. No. 03811739.8, the Chinese counterpart of the present application, dated Dec. 5, 2006.
Response to Office Action in Indian Patent Appin. No. 2630/DELNP/2004, the Indian counterpart of the present application, dated Jul. 24, 2006.
Response to Office Action in Japanese Patent Appin. No. 2003-580299, the Japanese counterpart of the present application, dated Jul. 28, 2006.
Rewcastle et al. (1995) "Tyrosine Kinase Inhibitors. 5 . . . 4-(Phenylamino)quinazolines as Potent . . . Inhibitors of the Tyrosine Kinase Domain of the Epidermal Growth Factor Receptor" J.Med. Chem. 38: 3482-3487.
Singh et al. (1998) "Inhibitors of the epidermal growth factor receptor protein tyrosine kinase: A quantitative structure-activity relationship analysis" J. Enzyme Inhibition 13: 125-134.
Smaill et al. (2000) "Tyrosine kinase inhibitors. 17. Irreversible inhibitors of the epidermalgrowth factor receptor: 4-(Phenylamino)quinazoline- and 4-(Phe-nylamino)pyrido" J Med Chem 43(16): 3199.
Stamos et al., "Structure of the Epidermal Growth Factor Receptor Kinase Domain Alone and in Complex with a 4-Anilinoquinazoline Inhibitor," J. Bio. Chem. 277(48):46265-46272 (2002).
Tang, Patricia, A., et al; A Review of Erlotinib and its Clinical Use; Expert OpinionPharmacotherapy (2006) vol. 7, No. 2 pp. 177-193.
Traxler, "Monthly Focus: Oncologic, Endocrine & Metabolic: Tyrosine kinase inhibitors in cancer treatment (Part II)," Expert Opinion on Therapeutic Patents 8:1599-1625 (1998).
Traxler, "Oncologic, Endocrine & Metabolic: Protein tyrosine kinase inhibitors in cancer treatment," Expert Opinion on Therapeutic Patents 7:571-588 (1997).
Tsou et al., "6-Substituted-4-(3-bromophenylamino)quinazolines As Putative Irreversible Inhibitors of the Epidermal Growth Factor Receptor (Egfr) and Human Epidermal Growth Factor Receptor (Her-2) Tyrosine Kinases with Enhanced Antitumor Activity," J. Med. Chem. 44:2719-2734 (2001).
Vema et al., "Design of EGFR Kinase Inhibitors: A Ligand-Based Approach and Its Confirmation with Structure-Based Studies," Bioorg. Med. Chem. 11:4643-4653 (2003).
Wright et al. (2001) "Allosteric inhibition of fructose-1,6-bisphosphatase by anilinoquinazolines" Bioorg Med Chem Lett. 11(1): 17-21.
Boschelli, Diane H.; Small Molecule Inhibitors of Receptor Tyrosine Kinases; Review Article; Chemical Sciences (2001) pp. 1-35.
Dahlin, Constance; Home HealthCare Nurse (2006) vol. 24, No. 3 pp. 148-55.
Kozielski, J; Polish Merkur Lekarski (2003) vol. 14, No. 4 p. 666-7.
International Search Report for PCT/EP2007/061355 mailed Jul. 15, 2008.

SPIROCYCLIC HETEROCYCLES MEDICAMENTS CONTAINING SAID COMPOUNDS, USE THEREOF AND METHOD FOR THEIR PRODUCTION

This application is a divisional of U.S. Ser. No. 12/865,431, filed on Nov. 4, 2010, which is the national phase entry under 35 U.S.C. §371 of International Application No. PCT/EP2009/000805, filed Feb. 5, 2009, which claims priority to European Patent Application No. 08101353.4, filed Feb. 7, 2008, which are hereby incorporated by reference in their entireties.

The present invention relates to spirocyclic heterocycles of general formula

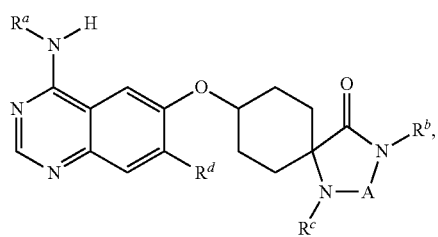

(I)

the tautomers, the stereoisomers, the mixtures thereof and the salts thereof, particularly the physiologically acceptable salts thereof with inorganic or organic acids, which have valuable pharmacological properties, particularly an inhibitory effect on signal transduction mediated by tyrosine kinases, the use thereof for the treatment of diseases, particularly tumoral diseases as well as benign prostatic hyperplasia (BPH), diseases of the lungs and airways and the preparation thereof.

The problem of the present invention is to prepare new compounds which on the basis of their pharmaceutical effectiveness as tyrosine-kinase inhibitors, may be used therapeutically, i.e. for the treatment of pathophysiological processes caused by hyperfunction of tyrosine kinases.

DETAILED DESCRIPTION OF THE INVENTION

It has surprisingly been found that the problem mentioned above is solved by compounds of formula (I), wherein the groups $R^a$ to $R^d$ and A have the meanings given hereinafter.

The present invention therefore relates to compounds of general formula (I),

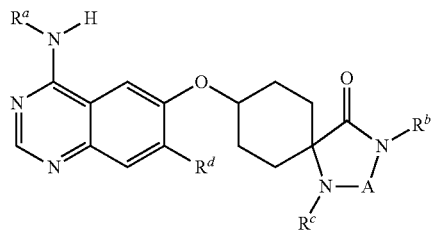

(I)

wherein $R^a$ denotes a phenyl or 1-phenylethyl group, wherein the phenyl nucleus is substituted in each case by the groups $R^1$ to $R^3$, wherein $R^1$ and $R^2$ which may be identical or different, denote hydrogen or
a group selected from among
F, Cl, Br, I, $OCH_2F$, $OCHF_2$, $OCF_3$, $CH_2F$, $CHF_2$, $CF_3$, CN, $NO_2$, $NH_2$ and OH,
or
a group selected from among
$C_{1-4}$-alkyl, $C_{1-4}$-alkyl-O, $C_{2-3}$-alkenyl, $C_{2-3}$-alkynyl, phenyl, phenyl-O, phenyl-$C_{1-3}$-alkyl- and phenyl-$C_{1-3}$- alkyl-O, heteroaryl, heteroaryl-O, heteroaryl-$C_{1-3}$-alkyl and heteroaryl-$C_{1-3}$-alkyl-O, while the above-mentioned phenyl groups are mono- or disubstituted by groups $R^5$,
and
$R^3$ denotes hydrogen,
or
a group selected from among
F, Cl, Br and $CH_3$,
$R^b$ denotes hydrogen, or a group, optionally substituted, selected from among $C_{1-6}$-alkyl, $C_{3-6}$-cycloalkyl- and $C_{3-6}$-cycloalkyl-$C_{1-3}$-alkyl,
$R^c$ denotes hydrogen, or an optionally substituted group selected from among $C_{1-6}$-alkyl, $C_{3-6}$-cycloalkyl, $C_{3-6}$-cycloalkyl-$C_{1-3}$-alkyl, $C_{1-6}$-alkyl-CO, $C_{3-6}$-cycloalkyl-CO, $C_{3-6}$-cycloalkyl-$C_{1-3}$-alkyl-CO, $C_{1-6}$-alkyl-$SO_2$, $C_{3-6}$-cycloalkyl-$SO_2$, $C_{3-6}$-cycloalkyl-$C_{1-3}$-alkyl-$SO_2$, phenyl-CO— and phenyl-$SO_2$,
$R^d$ denotes hydrogen or
a group selected from among
F, Cl, Br, I, OH, $C_{1-4}$-alkyl, $C_{1-4}$-alkyl-O, $C_{1-2}$-alkyl-O substituted by 1 to 3 fluorine atoms, $C_{3-7}$-cycloalkyl-O, $C_{3-7}$-cycloalkyl-$C_{1-4}$-alkyl-O, tetrahydrofuran-3-yl-O, tetrahydropyran-3-yl-O, tetrahydro-pyran-4-yl-O, tetrahydrofuranyl-$C_{1-4}$-alkyl-O— and tetrahydropyranyl-$C_{1-4}$-alkyl-O,
or
$R^4$—$C_{1-4}$-alkyl, while the linking of the groups $R^4$ may take place via each C atom of the alkyl group,
or
$R^4$—$C_{2-4}$-alkyl-O, wherein the group $R^4$ is separated from the oxygen atom by at least 2 C atoms,
or
a group selected from among
pyrrolidin-2-yl-$C_{1-4}$-alkyl-O, pyrrolidin-3-yl-$C_{1-4}$-alkyl-O, piperidin-2-yl-$C_{1-4}$-alkyl-O, piperidin-3-yl-$C_{1-4}$-alkyl-O, piperidin-4-yl-$C_{1-4}$-alkyl-O, azepan-2-yl-$C_{1-4}$-alkyl-O, azepan-3-yl-$C_{1-4}$-alkyl-O, azepan-4-yl-$C_{1-4}$-alkyl-O, morpholin-2-yl-$C_{1-4}$-alkyl-O, morpholin-3-yl-$C_{1-4}$-alkyl-O, 1-($C_{1-3}$-alkyl)-pyrrolidin-2-yl-$C_{1-4}$-alkyl-O, 1-($C_{1-3}$-alkyl)-pyrrolidin-3-yl-$C_{1-4}$-alkyl-O, 1-($C_{1-3}$-alkyl)-piperidin-2-yl-$C_{1-4}$-alkyl-O, 1-($C_{1-3}$-alkyl)-piperidin-3-yl-$C_{1-4}$-alkyl-O, 1-($C_{1-3}$-alkyl)-piperidin-4-yl-$C_{1-4}$-alkyl-O, 1-($C_{1-3}$-alkyl)-azepan-2-yl-$C_{1-4}$-alkyl-O, 1-($C_{1-3}$-alkyl)-azepan-3-yl-$C_{1-4}$-alkyl-O, 1-($C_{1-3}$-alkyl)-azepan-4-yl-$C_{1-4}$-alkyl-O, 4-($C_{1-3}$-alkyl)-morpholin-2-yl-$C_{1-4}$-alkyl-O— and 4-($C_{1-3}$-alkyl)-morpholin-3-yl-$C_{1-4}$-alkyl-O,
wherein
$R^4$ denotes a group, which may be identical or different, selected from among OH, $C_{1-3}$-alkyl-O, $C_{3-6}$-cycloalkyl-O, $NH_2$, $C_{1-3}$-alkyl-NH, ($C_{1-3}$-alkyl)$_2$N, (2-methoxyethyl)$_2$N, pyrrolidin-1-yl, piperidin-1-yl, azepan-1-yl, morpholin-4-yl, 1,4-oxazepan-4-yl, 2-oxa-5-aza-bicyclo[2,2,1]hept-5-yl, 3-oxa-8-aza-bicyclo[3.2.1]oct-8-yl, 8-oxa-3-aza-bicyclo[3.2.1]oct-3-yl, piperazin-1-yl, 4-($C_{1-3}$-alkyl)-piperazin-1-yl, 1,4-diazepan-1-yl, 4-($C_{1-3}$-alkyl)-1,4-diazepan-1-yl, HCO—

NH, $C_{1-4}$-alkyl-CO—NH, $C_{1-3}$-alkyl-O—$C_{1-3}$-alkyl-CO—NH, $C_{1-4}$-alkyl-O—CO—NH, $H_2NCONH$, $C_{1-3}$-alkyl-NH—CO—NH, $(C_{1-3}$-alkyl$)_2$N—CONH, pyrrolidin-1-yl-CO—NH, piperidin-1-yl-CO—NH, piperazin-1-yl-CO—NH, 4-($C_{1-3}$-alkyl)-piperazin-1-yl-CO—NH, morpholin-4-yl-CO—NH— and $C_{1-4}$-alkyl-$SO_2$—NH, while the pyrrolidinyl, piperidinyl, azepan-1-yl, piperazinyl, 1,4-diazepan-1-yl, morpholinyl- and 1,4-oxazepan-4-yl groups mentioned above in the definition of the group $R^d$ may each additionally be substituted by one or two $C_{1-3}$-alkyl groups, and wherein the above-mentioned phenyl groups are mono- or disubstituted by groups $R^5$, wherein $R^5$ denotes hydrogen, or a group, which may be identical or different, selected from among F, Cl, Br, I, OH, CN, $C_{1-3}$-alkyl, $C_{1-3}$-alkyl-O, $CHF_2$, $CF_3$, —O—$CHF_2$ and —O—$CF_3$, and unless stated otherwise, the above-mentioned alkyl groups may be straight-chain or branched, A denotes —CO or —$C_1$-$C_3$-alkylene, while the —$C_1$-$C_3$-alkylene- group may be 1-, 2-, 3- or 4-substituted by a group $R^6$, and $R^6$ which may be identical or different, denotes hydrogen, or a group selected from among OH, $C_1$-$C_4$-alkyl and —O—$C_1$-$C_4$-alkyl optionally in the form of the tautomers, the racemates, the enantiomers, the diastereomers and the mixtures thereof, and optionally the pharmacologically acceptable acid addition salts, solvates and hydrates thereof.

Preferred compounds of formula (I) are those wherein $R^a$ denotes a group selected from among 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 4-fluoro-3-methyl-phenyl- and 3-chloro-2-methyl-phenyl, $R^b$ and $R^c$ which may be identical or different, denote hydrogen or $C_{1-3}$-alkyl, $R^d$ denotes $C_{1-3}$-alkyl-O, unless stated otherwise, the above-mentioned alkyl groups may be straight-chain or branched, A denotes —$CH_2CH_2$, while the —$CH_2CH_2$— group may be substituted by 1 or 2 methyl groups, optionally in the form of the tautomers, the racemates, the enantiomers, the diastereomers and the mixtures thereof, and optionally the pharmacologically acceptable acid addition salts, solvates and hydrates thereof.

The invention further relates to compounds of formula (I) for use as medicaments.

Preferably the compounds of formula (I) are used in cases of inflammatory or allergic diseases of the airways.

The compounds of formula (I) are particularly preferably used in cases of a disease selected from among chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), paediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases, alveolitis, hyperreactive airways, nasal polyps, pulmonary oedema, pneumonitis of different origins, e.g. radiation-induced or caused by aspiration or infectious pneumonitis, collagenoses such as lupus erythematodes, systemic sclerodermy, sarcoidosis and Boeck's disease, and for treating complications in asthma and COPD triggered by viral, bacterial or other causes, for treating viral or bacterial infections of the airways or lungs.

It is also particularly preferred to use the compounds of formula (I) in cases of inflammatory or allergic complaints in which autoimmune reactions are involved. It is also particularly preferred to use the compounds of formula (I) in cases of a disease in the form of benign or malignant tumours.

The invention further relates to a pharmaceutical formulation containing a compound of formula (I).

Preferably an orally administered pharmaceutical formulation containing a compound of formula (I) is used.

The invention further relates to medicament combinations which contain, besides one or more compounds of formula (I), as further active substances, one or more compounds selected from among the categories of betamimetics, anticholinergics, corticosteroids, further PDE4-inhibitors, LTD4-antagonists, EGFR-inhibitors, dopamine agonists, H1-antihistamines, PAF-antagonists and PI3-kinase inhibitors or double or triple combinations thereof.

TERMS AND DEFINITIONS USED

By the term "optionally substituted" is meant within the scope of the invention the above-mentioned group, optionally substituted by a lower-molecular group. Examples of lower-molecular groups regarded as chemically meaningful are groups consisting of 1-25 atoms. Preferably such groups have no negative effect on the pharmacological efficacy of the compounds.

For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

Also included in the subject-matter of this invention are the compounds according to the invention, including the salts thereof, wherein one or more hydrogen atoms, for example one, two, three, four or five hydrogen atoms, are replaced by deuterium.

Where a hyphen open on one side "-" is used in the structural formula of a substituent, this hyphen is to be understood as the linkage point to the remainder of the molecule. The substituent replaces the corresponding groups $R^a$, $R^b$, etc. If no hyphen open on one side is used in the structural formula of a substituent, the linkage point to the remainder of the molecule is clear from the structural formula itself.

Compounds of general formula (I) may contain acid groups, primarily carboxyl groups, and/or basic groups such as e.g. amino functions. Compounds of general formula (I) may therefore be present as internal salts, as salts with pharmaceutically useable inorganic acids such as hydrochloric acid, sulphuric acid, phosphoric acid, sulphonic acid or organic acids (such as for example maleic acid, fumaric acid, citric acid, tartaric acid or acetic acid) or as salts with pharmaceutically useable bases such as alkali metal or alkaline earth metal hydroxides or carbonates, zinc or ammonium hydroxides or organic amines such as e.g. diethylamine, triethylamine, triethanolamine, inter alia. For preparing the alkali metal and alkaline earth metal salts of the compound of formula (I), it is preferable to use the alkali metal and alkaline earth metal hydroxides and hydrides, while the hydroxides and hydrides of the alkali metals, particularly sodium and potassium are preferred, and sodium and potassium hydroxide are particularly preferred. (See also *Pharmaceutical Salts*, S. M. Birge et al., *J. Pharm. Sci.* (1977), 66, 1-19)

As already mentioned, the compounds of general formula (I) may be converted into the salts thereof, particularly for pharmaceutical use, into the pharmacologically acceptable acid addition salts thereof with an inorganic or organic acid. Suitable acids for this purpose include for example succinic acid, hydrobromic acid, acetic acid, fumaric acid, maleic acid, methanesulphonic acid, lactic acid, phosphoric acid, hydrochloric acid, sulphuric acid, tartaric acid or citric acid. In addition, mixtures of the above-mentioned acids may be used.

The present invention relates to the respective compounds, optionally in the form of the individual diastereomers, mixtures of the individual diastereomers and/or individual enantiomers, mixtures of the individual enantiomers or racemates thereof, in the form of the tautomers as well as in the form of the free bases or the corresponding acid addition salts with pharmacologically acceptable acids—such as for example acid addition salts with hydrohalic acids—for example hydrochloric or hydrobromic acid or organic acids—such as for example tartaric acid, fumaric acid, citric acid or methanesulphonic acid.

"Protective groups" for the purposes of the present invention is a collective term for organic groups with which certain functional groups of a molecule containing a number of active centres can temporarily be protected from attack by reagents so that reactions take place only at the desired (unprotected) sites. The protective groups should be introduced selectively under mild conditions. They must be stable for the duration of the protection under all the conditions of the reactions and purifying procedures which are to be carried out; racemisations and epimerisations must be suppressed. Protective groups should be capable of being cleaved again under mild conditions selectively and ideally in high yields. The choice of a suitable protective group, the reaction conditions (solvent, temperature, duration, etc.), and also the options for removing a protective group are known in the art (e.g. Philip Kocienski, Protecting Groups, 3rd ed. 2004, THIEME, Stuttgart, ISBN: 3131370033).

By an "organic solvent" is meant, within the scope of the invention, an organic, low-molecular substance which can dissolve other organic substances by a physical method. To be suitable the prerequisite for the solvent is that neither the dissolving substance nor the dissolved substance should be chemically altered during the dissolving process, i.e. the components of the solution should be recoverable in their original form by physical separation processes such as distillation, crystallisation, sublimation, evaporation or adsorption. For various reasons, not only the pure solvents but also mixtures that combine the dissolving properties may be used. Examples include:

alcohols, preferably methanol, ethanol, propanol, butanol, octanol, cyclohexanol;
glycols, preferably ethyleneglycol, diethyleneglycol;
ethers/glycolethers, preferably diethyl ether, tert-butylmethylether, dibutylether, anisol, 1,4-dioxane, tetrahydrofuran, mono-, di-, tri-, polyethyleneglycol ethers;
ketones, preferably acetone, butanone, cyclohexanone;
esters, preferably acetic acid esters, glycolesters;
amides and other nitrogen compounds, preferably N,N-dimethylformamide, pyridine, N-methylpyrrolidone, acetonitrile;
sulphur compounds, preferably carbon disulphide, dimethylsulphoxide, sulpholane;
nitro compounds, preferably nitrobenzene;
halogenated hydrocarbons, preferably dichloromethane, chloroform, tetrachlormethane, tri- and tetrachloroethene, 1,2-dichloroethane, chlorofluorocarbons;
aliphatic or alicyclic hydrocarbons, preferably benzines, petroleum ether, cyclohexane, methylcyclohexane, decaline, terpene-L.; or
aromatic hydrocarbons, preferably benzene, toluene, o-xylene, m-xylene, p-xylene;
or corresponding mixtures thereof.

The term diastereomerically pure describes within the scope of the present invention compounds of formula (I), which are present in a diastereomeric purity of at least 85% de, preferably at least 90% de, particularly preferably >95% de. The term de (diastereomeric excess) is known in the art and describes the optical purity of diastereomeric compounds.

The term enantiomerically pure describes within the scope of the present invention compounds of formula (I), which are present in an enantiomerical purity of at least 85% ee, preferably at least 90% ee, particularly preferably >95% ee. The term ee (enantiomeric excess) is known in the art and describes the optical purity of chiral compounds.

By the term "$C_{1-6}$-alkyl" (including those which are part of other groups) are meant branched and unbranched alkyl groups with 1 to 6 carbon atoms and by the term "$C_{1-4}$-alkyl" are meant branched and unbranched alkyl groups with 1 to 4 carbon atoms. Preferred are alkyl groups with 1 to 4 carbon atoms, particularly preferably alkyl groups with 1 to 2 carbon atoms. Examples include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-3}$-alkylene" (including those which are part of other groups) are meant branched and unbranched alkylene groups with 1 to 3 carbon atoms. Preferred are alkylene groups with 1 to 2 carbon atoms. Examples include: methylene, ethylene, propylene, 1-methylethylene, butylene, 1-methylpropylene, 1,1-dimethylethylene and 1,2-dimethylethylene. Unless stated otherwise, the definition alkylene includes all the possible isomeric forms of the groups in question with the same number of carbons. Thus, for example, propylene also includes 1-methylethylene.

By the term "$C_{3-7}$-cycloalkyl" (including those which are part of other groups) are meant cyclic alkyl groups with 3 or 7 carbon atoms. Examples include: cyclopropyl, cyclobutyl, cyclopentyl, cyclohexyl or cycloheptyl. Unless otherwise stated, the cyclic alkyl groups may be substituted by one or more groups selected from among methyl, ethyl, iso-propyl, tert-butyl, hydroxy and fluorine.

By the term "aryl" (including those which are part of other groups) are meant aromatic ring systems with 6, 10 or 14 carbon atoms. Examples include: phenyl, naphthyl, anthracenyl or phenanthrenyl, the preferred aryl group being phenyl. Unless otherwise stated, the aromatic groups may be substituted by one or more groups $R^5$.

Particularly preferably the term "aryl" in each case denotes a phenyl group which is mono- or disubstituted by $R^5$, wherein the substituents $R^5$ may be identical or different and
$R^5$ denotes hydrogen, or
a group selected from among
F, Cl, Br, I, OH, CN, $C_{1-3}$-alkyl, $C_{1-3}$-alkyl-O, $CHF_2$, $CF_3$, —O—$CHF_2$ and
—O—$CF_3$.

By the term "heteroaryl" are meant 5-10-membered mono- or bicyclic heteroaryl rings, wherein up to three C atoms may be replaced by one or more heteroatoms selected from among oxygen, nitrogen and sulphur, these rings containing sufficient conjugated double bonds to form an aromatic system. Each of the above-mentioned heterocycles may optionally also be fused to a benzene ring. The heteroaryl rings may, unless otherwise described, carry one or more substituents, for example.

The ring may be linked to the molecule via a carbon atom or, if available, via a nitrogen atom. The following are examples of five- or six-membered heterocyclic aromatic groups:

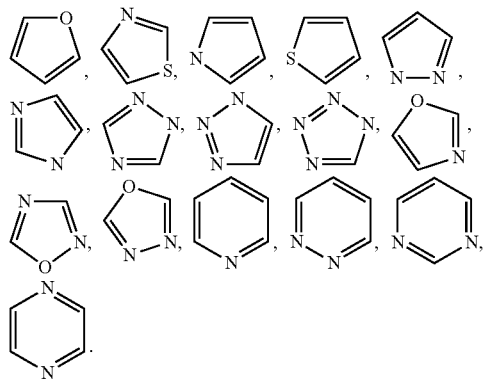

Examples of 5-10-membered bicyclic heteroaryl rings include pyrrolizine, indole, indolizine, isoindole, indazole, purine, quinoline, isoquinoline, quinoxaline, benzimidazole, benzofuran, benzothiophene, benzothiazole, benzoisothiazole, pyridopyrimidine, pteridine, pyrimidopyrimidine.

Particularly preferably, the term "heteroaryl" denotes a pyridinyl, pyridazinyl, pyrimidinyl or pyrazinyl group, which is mono- or disubstituted in each case by the group $R^5$, wherein the substituents $R^5$ may be identical or different and $R^5$ is as hereinbefore defined.

"Halogen" within the scope of the present invention denotes fluorine, chlorine, bromine or iodine. Unless stated to the contrary, fluorine, chlorine and bromine are regarded as preferred halogens.

The substituent $R^a$ may represent a phenyl or 1-phenylethyl group, preferably a phenyl group, wherein the phenyl nucleus is substituted in each case by the groups $R^1$ to $R^3$.

Particularly preferably the substituent $R^a$ denotes a group, selected from among 3-chloro-2-fluoro-phenyl, 3-chloro-4-fluoro-phenyl, 5-chloro-2-fluoro-phenyl, 2-fluoro-3-methyl-phenyl, 2-fluoro-5-methyl-phenyl, 4-fluoro-3-methyl-phenyl- and 3-chloro-2-methyl-phenyl. Most particularly preferably the substituent $R^a$ denotes a 3-chloro-2-fluoro-phenyl group.

The substituent $R^b$ may represent hydrogen, or an optionally substituted group selected from among $C_{1-6}$-alkyl, $C_{3-6}$-cycloalkyl- and $C_{3-6}$-cycloalkyl-$C_{1-3}$-alkyl, preferably hydrogen and $C_{1-3}$-alkyl, particularly preferably hydrogen and methyl.

The substituent $R^c$ may represent hydrogen, or an optionally substituted group selected from among $C_{1-6}$-alkyl, $C_{3-6}$-cycloalkyl, $C_{3-6}$-cycloalkyl-$C_{1-3}$-alkyl, $C_{1-6}$-alkyl-CO, $C_{3-6}$-cycloalkyl-CO, $C_{3-6}$-cycloalkyl-$C_{1-3}$-alkyl-CO, $C_{1-6}$-alkyl-$SO_2$, $C_{3-6}$-cycloalkyl-$SO_2$—, $C_{3-6}$-cycloalkyl-$C_{1-3}$-alkyl-$SO_2$, phenyl-CO— and phenyl-$SO_2$, preferably hydrogen and $C_{1-3}$-alkyl, particularly preferably hydrogen and methyl.

The substituent $R^d$ may denote hydrogen or
a group selected from among
F, Cl, Br, I, OH, $C_{1-4}$-alkyl, $C_{1-4}$-alkyl-O, $C_{1-2}$-alkyl-O substituted by 1 to 3 fluorine atoms, $C_{3-7}$-cycloalkyl-O, $C_{3-7}$-cycloalkyl-$C_{1-4}$-alkyl-O, tetrahydrofuran-3-yl-O, tetrahydropyran-3-yl-O, tetrahydro-pyran-4-yl-O, tetrahydrofuranyl-$C_{1-4}$-alkyl-O— and tetrahydropyranyl-$C_{1-4}$-alkyl-O,
or
$R^4$—$C_{1-4}$-alkyl, wherein the linking of the groups $R^4$ may take place via each C atom of the alkyl group,
or
$R^4$—$C_{2-4}$-alkyl-O, wherein the group $R^4$ is separated from the oxygen atom by at least 2 C atoms,
or
a group selected from among
pyrrolidin-2-yl-$C_{1-4}$-alkyl-O, pyrrolidin-3-yl-$C_{1-4}$-alkyl-O, piperidin-2-yl-$C_{1-4}$-alkyl-O, piperidin-3-yl-$C_{1-4}$-alkyl-O, piperidin-4-yl-$C_{1-4}$-alkyl-O, azepan-2-yl-$C_{1-4}$-alkyl-O, azepan-3-yl-$C_{1-4}$-alkyl-O, azepan-4-yl-$C_{1-4}$-alkyl-O, morpholin-2-yl-$C_{1-4}$-alkyl-O, morpholin-3-yl-$C_{1-4}$-alkyl-O, 1-($C_{1-3}$-alkyl)-pyrrolidin-2-yl-$C_{1-4}$-alkyl-O, 1-($C_{1-3}$-alkyl)-pyrrolidin-3-yl-$C_{1-4}$-alkyl-O, 1-($C_{1-3}$-alkyl)-piperidin-2-yl-$C_{1-4}$-alkyl-O, 1-($C_{1-3}$-alkyl)-piperidin-3-yl-$C_{1-4}$-alkyl-O, 1-($C_{1-3}$-alkyl)-piperidin-4-yl-$C_{1-4}$-alkyl-O, 1-($C_{1-3}$-alkyl)-azepan-2-yl-$C_{1-4}$-alkyl-O, 1-($C_{1-3}$-alkyl)-azepan-3-yl-$C_{1-4}$-alkyl-O, 1-($C_{1-3}$-alkyl)-azepan-4-yl-$C_{1-4}$-alkyl-O, 4-($C_{1-3}$-alkyl)-morpholin-2-yl-$C_{1-4}$-alkyl-O and 4-($C_{1-3}$-alkyl)-morpholin-3-yl-$C_{1-4}$-alkyl-O—,
preferably $C_{1-3}$-alkyl-O—, particularly preferably $CH_3$—O—,
wherein the pyrrolidinyl, piperidinyl, azepan-1-yl, piperazinyl, 1,4-diazepan-1-yl, morpholinyl and 1,4-oxazepan-4-yl groups mentioned above in the definition of the group $R^d$ may each additionally be substituted by one or two $C_{1-3}$-alkyl groups,
and
wherein the above-mentioned phenyl groups are mono- or disubstituted by groups $R^5$.

The substituent $R^1$ may denote hydrogen or
a group selected from among
F, Cl, Br, I, $OCH_2F$, $OCHF_2$, $OCF_3$, $CH_2F$, $CHF_2$, $CF_3$, CN, $NO_2$, $NH_2$ and OH,
or
a group selected from among
$C_{1-4}$-alkyl, $C_{1-4}$-alkyl-O, $C_{2-3}$-alkenyl, $C_{2-3}$-alkynyl,
phenyl, phenyl-O, phenyl-$C_{1-3}$-alkyl, phenyl-$C_{1-3}$-alkyl-O, heteroaryl, heteroaryl-O, heteroaryl-$C_{1-3}$-alkyl and heteroaryl-$C_{1-3}$-alkyl-O,
wherein the above-mentioned phenyl groups are mono- or disubstituted by groups $R^5$,
preferably hydrogen, fluorine, chlorine, bromine or methyl, particularly preferably hydrogen, fluorine, chlorine or methyl.

The substituent $R^2$ may represent hydrogen or a group selected from among

F, Cl, Br, I, $OCH_2F$, $OCHF_2$, $OCF_3$, $CH_2F$, $CHF_2$, $CF_3$, ON, $NO_2$, $NH_2$ and OH, or a group selected from among $C_{1-4}$-alkyl, $C_{1-4}$-alkyl-O, $C_{2-3}$-alkenyl, $C_{2-3}$-alkynyl, phenyl, phenyl-O, phenyl-$C_{1-3}$-alkyl, phenyl-$C_{1-3}$-alkyl-O, heteroaryl, heteroaryl-O, heteroaryl-$C_{1-3}$-alkyl and heteroaryl-$C_{1-3}$-alkyl-O, wherein the above-mentioned phenyl groups are mono- or disubstituted by groups $R^5$, preferably hydrogen, fluorine, chlorine or methyl, particularly preferably hydrogen, fluorine or chlorine.

The substituent $R^3$ may represent hydrogen, or a group selected from among F, Cl, Br and $CH_3$, preferably hydrogen.

The substituent $R^4$ may represent a group, which may be identical or different, selected from among OH, $C_{1-3}$-alkyl-O, $C_{3-6}$-cycloalkyl-O, $NH_2$, $C_{1-3}$-alkyl-NH, $(C_{1-3}$-alkyl$)_2$N, (2-methoxyethyl$)_2$N, pyrrolidin-1-yl, piperidin-1-yl, azepan-1-yl, morpholin-4-yl, 1,4-oxazepan-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-($C_{1-3}$-alkyl)-piperazin-1-yl, 1,4-diazepan-1-yl, 4-($C_{1-3}$-alkyl)-1,4-diazepan-1-yl, HCO—NH, $C_{1-4}$-alkyl-CO—NH, $C_{1-3}$-alkyl-O—$C_{1-3}$-alkyl-CO—NH, $C_{1-4}$-alkyl-O—CO—NH, $H_2$NCONH, $C_{1-3}$-alkyl-NH—CO—NH, $(C_{1-3}$-alkyl$)_2$N—CONH, pyrrolidin-1-yl-CO—NH, piperidin-1-yl-CO—NH, piperazin-1-yl-CO—NH, 4-($C_{1-3}$-alkyl)-piperazin-1-yl-CO—NH, morpholin-4-yl-CO—NH— and $C_{1-4}$-alkyl-$SO_2$—NH—.

The substituent $R^5$ may represent hydrogen, or a group, which may be identical or different, selected from among F, Cl, Br, I, OH, CN, $C_{1-3}$-alkyl, $C_{1-3}$-alkyl-O, $CHF_2$, $CF_3$, —O—$CHF_2$ and —O—$CF_3$.

A may denote —CO— or —$C_1$-$C_3$-alkylene, preferably —$CH_2CH_2$—, wherein the —$C_1$-$C_3$-alkylene group may be 1-, 2-, 3- or 4-, preferably 1- or 2-substituted by a group $R^6$, The substituent $R^6$, which may be identical or different, may represent hydrogen, or a group selected from among OH, $C_1$-$C_4$-alkyl and —O—$C_1$-$C_4$-alkyl, preferably methyl.

A particularly preferred definition of A is —$CH_2CH_2$—.

Methods of Preparation

The following methods are suitable, for example, for preparing compounds of general formula (I):

a) reacting a compound of general formula

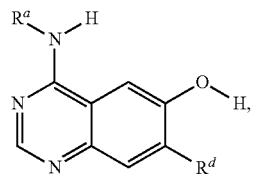

(II)

wherein $R^a$ and $R^d$ are as hereinbefore defined, with a compound of general formula

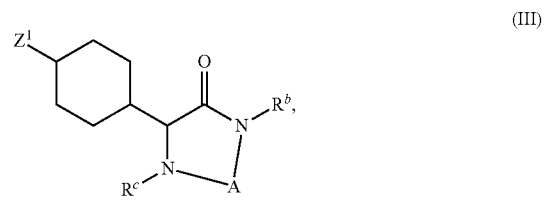

(III)

wherein $R^b$, $R^c$ and A are as hereinbefore defined and $Z^1$ denotes a leaving group such as a halogen atom, e.g. a chlorine, bromine or iodine atom, a sulphonyloxy group such as a methanesulphonyloxy or p-toluenesulphonyloxy group or a hydroxy group.

With a compound of general formula (III), wherein $Z^1$ denotes a halogen atom or a sulphonyloxy group, the reaction is expediently carried out in a solvent such as ethanol, isopropanol, acetonitrile, toluene, tetrahydrofuran, 1,4-dioxane, N,N-dimethylformamide, dimethylsulphoxide or N-methylpyrrolidinone, preferably in the presence of a base such as potassium carbonate, caesium carbonate, potassium hydroxide, potassium-tert-butoxide, sodium hydride or N-ethyl-diisopropylamine, at temperatures in the range from 20° C. to 160° C., for example at temperatures in the range from 60° C. to 140° C.

With a compound of general formula III wherein $Z^1$ denotes a hydroxy group, the reaction is carried out in the presence of a dehydrating agent, preferably in the presence of a phosphine and an azodicarboxylic acid derivative such as e.g. triphenylphosphine/diethyl azodicarboxylate, conveniently in a solvent such as methylene chloride, acetonitrile, tetrahydrofuran, 1,4-dioxane, toluene or ethyleneglycol diethylether at temperatures between −50 and 150° C., but preferably at temperatures between −20 and 80° C.

b) In order to prepare compounds of general formula I wherein $R^b$ and $R^c$ each denote a hydrogen atom and A represents a —CO— group, reacting a compound of general formula

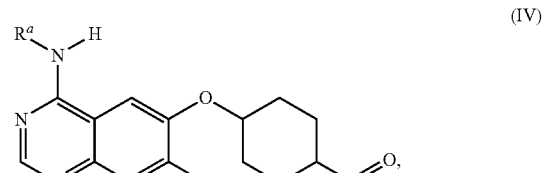

(IV)

wherein $R^a$ and $R^d$ are as hereinbefore defined, with an alkali metal cyanide and ammonium carbonate.

The reaction is carried out for example in a solvent or mixture of solvents such as methanol, ethanol, ethanol/water or isopropanol at temperatures between ambient temperature and 120° C. Further references to the synthesis of hydantoins can be found for example in the following publication: Meusel, M.; Guetschow, M., Organic Preparations and Procedures International (2004), 36 (5), 391-443.

c) reacting a compound of general formula (V)

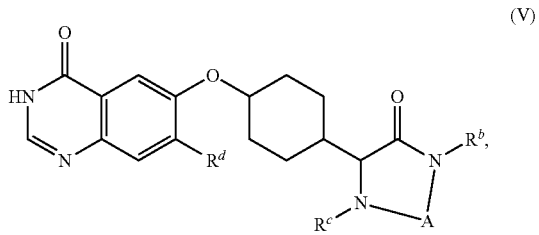

(V)

wherein $R^b$, $R^c$, $R^d$ and A are as hereinbefore defined, with a halogenating agent, for example an acid halide such as thionyl chloride, thionyl bromide, phosphorus trichloride, phosphorus pentachloride or phosphorus oxychloride, to obtain an intermediate compound of general formula (VI),

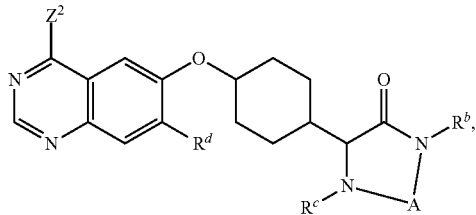

(VI)

wherein $R^b$, $R^c$, $R^d$ and A are as hereinbefore defined and $Z^2$ denotes a halogen atom such as a chlorine or bromine atom, and subsequent reaction with a compound of general formula (VII),

$R^a$—$NH_2$   (VII), wherein $R^a$ is as hereinbefore defined, or the salts thereof.

The reaction with the halogenating agent is optionally carried out in a solvent such as methylene chloride, chloroform, acetonitrile or toluene and optionally in the presence of a base such as N,N-diethylaniline, pyridine, triethylamine or N-ethyl-diisopropylamine at temperatures in the range from 20° C. to 160° C., preferably from 40° C. to 120° C. Preferably, however, the reaction is carried out with thionyl chloride and catalytic amounts of N,N-dimethylformamide at the boiling temperature of the reaction mixture or, however, with phosphorus oxychloride in acetonitrile in the presence of triethylamine at the boiling temperature of the reaction mixture.

The reaction of the compound of general formula (VI) with the compound of general formula (VII) or the salts thereof is conveniently carried out in a solvent such as ethanol, isopropanol, acetonitrile, 1,4-dioxane or N,N-dimethylformamide, optionally in the presence of a base such as potassium carbonate, triethylamine or N-ethyl-diisopropylamine, at temperatures in the range from 20° C. and 160° C., preferably from 60° C. to 120° C. However, the reaction is preferably carried out in isopropanol at the boiling temperature of the reaction mixture.

The reaction of a compound of general formula (V) to obtain a compound of general formula (I) may also be carried out as a one-pot reaction, for example in acetonitrile in the presence of triethylamine.

d) In order to prepare compounds of general formula I wherein $R^d$ denotes one of the optionally substituted alkyloxy groups mentioned hereinbefore:

reacting a compound of general formula

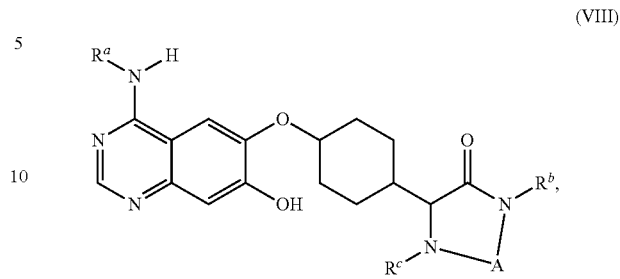

(VIII)

wherein $R^a$, $R^b$, $R^c$ and A are as hereinbefore defined, with a compound of general formula

$Z^3$—$R^{d'}$   (IX)

wherein $R^{d'}$ denotes a group selected from among $C_{1-4}$-alkyl, $C_{1-2}$-alkyl substituted by 1 to 3 fluorine atoms, $C_{3-7}$-cycloalkyl, $C_{3-7}$-cycloalkyl-$C_{1-4}$-alkyl, tetrahydrofuran-3-yl, tetrahydropyran-3-yl, tetrahydro-pyran-4-yl, tetrahydrofuranyl-$C_{1-4}$-alkyl and tetrahydropyranyl-$C_{1-4}$-alkyl, or $R^4$—$C_{2-4}$-alkyl, wherein the group $R^4$ is separated from $Z^3$ by at least 2 C atoms, or a group selected from among
pyrrolidin-2-yl-$C_{1-4}$-alkyl, pyrrolidin-3-yl-$C_{1-4}$-alkyl, piperidin-2-yl-$C_{1-4}$-alkyl, piperidin-3-yl-$C_{1-4}$-alkyl, piperidin-4-yl-$C_{1-4}$-alkyl, azepan-2-yl-$C_{1-4}$-alkyl, azepan-3-yl-$C_{1-4}$-alkyl, azepan-4-yl-$C_{1-4}$-alkyl, morpholin-2-yl-$C_{1-4}$-alkyl, morpholin-3-yl-$C_{1-4}$-alkyl, 1-($C_{1-3}$-alkyl)-pyrrolidin-2-yl-$C_{1-4}$-alkyl, 1-($C_{1-3}$-alkyl)-pyrrolidin-3-yl-$C_{1-4}$-alkyl, 1-($C_{1-3}$-alkyl)-piperidin-2-yl-$C_{1-4}$-alkyl, 1-($C_{1-3}$-alkyl)-piperidin-3-yl-$C_{1-4}$-alkyl, 1-($C_{1-3}$-alkyl)-piperidin-4-yl-$C_{1-4}$-alkyl, 1-($C_{1-3}$-alkyl)-azepan-2-yl-$C_{1-4}$-alkyl, 1-($C_{1-3}$-alkyl)-azepan-3-yl-$C_{1-4}$-alkyl, 1-($C_{1-3}$-alkyl)-azepan-4-yl-$C_{1-4}$-alkyl, 4-($C_{1-3}$-alkyl)-morpholin-2-yl-$C_{1-4}$-alkyl, 4-($C_{1-3}$-alkyl)-morpholin-3-yl-$C_{1-4}$-alkyl, and $Z^3$ denotes a leaving group such as a halogen atom, an alkylsulphonyloxy, arylsulphonyloxy or a hydroxy group.

If the leaving group is a halogen atom such as a chlorine, bromine or iodine atom or an alkylsulphonyloxy or arylsulphonyloxy group such as the methanesulphonyloxy or p-toluenesulphonyloxy group, the reaction is preferably carried out in the presence of an organic or inorganic base such as potassium carbonate, caesium carbonate, potassium hydroxide, sodium hydride or N-ethyl-diisopropylamine. If the leaving group is a hydroxy group, the reaction is carried out in the presence of a dehydrating agent, preferably in the presence of a phosphine and an azodicarboxylic acid derivative such as e.g. triphenylphosphine/diethyl azodicarboxylate.

e) In order to prepare compounds of general formula I wherein Rd denotes a $R^{4'}$—$C_{2-4}$-alkyl-O— group, wherein the group $R^{4'}$ is separated from the oxygen atom by at least 2 C atoms, and $R^{4'}$ denotes a group selected from among $NH_2$, $C_{1-3}$-alkyl-NH, ($C_{1-3}$-alkyl)$_2$N, (2-methoxyethyl)$_2$N, pyrrolidin-1-yl, piperidin-1-yl, azepan-1-yl, morpholin-4-yl, 1,4-oxazepan-4-yl, 2-oxa-5-aza-bicyclo[2.2.1]hept-5-yl, 3-oxa-8-aza-bicyclo[3.2.1]oct-8-yl, 8-oxa-3-aza-bicyclo[3.2.1]oct-3-yl, piperazin-1-yl, 4-($C_{1-3}$-alkyl)piperazin-1-yl, 1,4-diazepan-1-yl, 4-($C_{1-3}$-alkyl)-1,4-diazepan-1-yl: reacting a compound of general formula

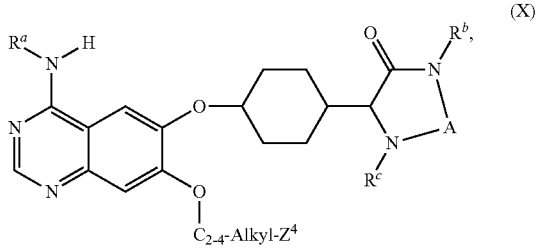

(X)

wherein $R^a$, $R^b$, $R^c$ and A are as hereinbefore defined and $Z^4$ denotes a leaving group such as a halogen atom, e.g. a chlorine, bromine or iodine atom or a sulphonyloxy group such as a methanesulphonyloxy or p-toluenesulphonyloxy group, with

(XI)

wherein $R^{4'}$ is as hereinbefore defined.

f) In order to prepare compounds of general formula I wherein $R^b$ denotes a hydrogen atom:

cleaving a protective group from a compound of general formula

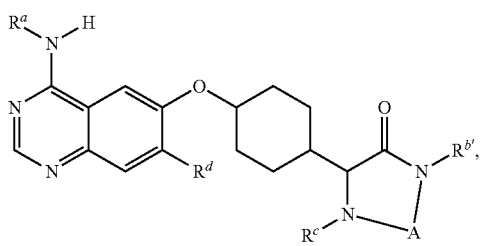

(XII)

wherein $R^a$, $R^c$, $R^d$ and A are as hereinbefore defined and $R^{b'}$ denotes a protective group, for example an optionally substituted benzyl group, a tert.-butyl group or a 2-(trimethylsilyl)ethyl group.

An optionally substituted benzyl group is for example cleaved hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid, at ambient temperatures between 0 and 100° C., but preferably at ambient temperatures between 20 and 60° C., and under a hydrogen pressure of 1 to 7 bar, but preferably from 3 to 5 bar. A 2,4-dimethoxybenzyl group is preferably cleaved in trifluoroacetic acid in the presence of anisol, thioanisol, pentamethylbenzene or triethylsilane.

An optionally substituted benzyl group or a tert.-butyl group may for example also be cleaved by treating with an acid such as trifluoroacetic acid, hydrochloric acid or hydrobromic acid, optionally using a solvent such as 1,4-dioxane, isopropanol, methylene chloride or toluene, optionally in the presence of anisole, thioanisole, pentamethylbenzene or triethylsilane.

A 2-(trimethylsilyl)ethyl group is cleaved for example by treatment with fluorides such as tetrabutylammonium fluoride, optionally using a solvent such as tetrahydrofuran or 1,4-dioxane.

Other suitable protective groups and possible ways of introducing and cleaving them are described for example in "Protective Groups in Organic Synthesis" by Theodora W. Greene and Peter G. M. Wuts, Wiley-VCH, or Philip Kocienski, Protecting Groups, 3rd ed. 2004, THIEME.

g) In order to prepare compounds of general formula I wherein $R^c$ denotes a hydrogen atom:

cleaving a protective group from a compound of general formula

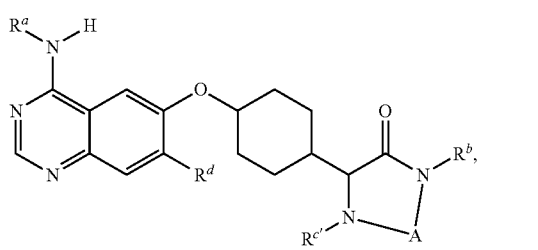

(XIII)

wherein $R^a$, $R^b$, $R^d$ and A are as hereinbefore defined and $R^{c'}$ denotes a protective group, for example an optionally substituted benzyl group or a formyl, acetyl, trifluoroacetyl, methoxycarbonyl, ethoxycarbonyl, tert.-butoxycarbonyl or benzyloxycarbonyl group.

The protective group is cleaved, for example, hydrolytically in an aqueous solvent, e.g. In water, isopropanol/water, acetic acid/water, tetrahydrofuran/water or 1,4-dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

An optionally substituted benzyl group, or a benzyloxycarbonylbenzyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 600° C., and under a hydrogen pressure of 1 to 7 bar, but preferably from 3 to 5 bar.

A tert.-butyloxycarbonyl group is preferably cleaved by treatment with an acid such as trifluoroacetic acid or hydrochloric acid, optionally using a solvent such as methylene chloride, 1,4-dioxane, methanol or diethyl ether.

A trifluoroacetyl group is preferably cleaved by treatment with an acid such as hydrochloric acid, optionally in the presence of a solvent such as acetic acid at temperatures between 50 and 120° C. or by treatment with sodium hydroxide solution, optionally in the presence of a solvent such as tetrahydrofuran at temperatures between 0 and 50° C.

Other suitable protective groups and possible ways of introducing and cleaving them are described for example in "Protective Groups in Organic Synthesis" by Theodora W. Greene and Peter G. M. Wuts, Wiley-VCH, or Philip Kocienski, Protecting Groups, 3rd ed. 2004, THIEME.

h) In order to prepare compounds of general formula I wherein A denotes a —C$_2$-C$_3$-alkylene group:
cyclising a compound of general formula

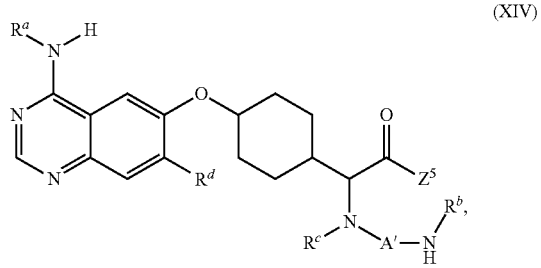

(XIV)

wherein R$^a$, R$^b$, R$^c$ and R$^d$ are as hereinbefore defined, A' denotes a —C$_2$-C$_3$-alkylene group and Z$^5$ denotes a leaving group such as a halogen atom, a hydroxy or alkyloxy group.

If the leaving group is a hydroxy group, the reaction is carried out in the presence of a dehydrating agent such as N,N'-carbonyldiimidazole, N,N'-dicyclohexylcarbodiimide, O-(benzotriazol-1-yl)-N,N,N'N'-tetramethyluronium-tetrafluoroborate (TBTU) or O-(7-azabenzotriazol-1-yl)-N,N,N',N'-tetramethyluronium-hexafluorophosphate (HATU), conveniently in a solvent such as methylene chloride, N,N-dimethylformamide, acetonitrile, tetrahydrofuran, 1,4-dioxane or ethyleneglycol diethyl ether at temperatures between −50° C. and 100° C., but preferably at temperatures between −20° C. and 60° C.

If the leaving group is a halogen atom, the reaction is preferably carried out in the presence of a base such as triethylamine, pyridine or N-ethyl-diisopropylamine, conveniently in a solvent such as methylene chloride, N,N-dimethylformamide, acetonitrile, tetrahydrofuran, 1,4-dioxane or ethyleneglycol diethyl ether at temperatures between −50° C. and 100° C., but preferably at temperatures between −20° C. and 60° C.

If the leaving group is an alkyloxy group, the reaction is optionally carried out in the presence of a base such as potassium carbonate, sodium hydroxide, triethylamine or N-ethyl-diisopropylamine, conveniently in a solvent such as methanol, ethanol, isopropanol, methylene chloride, N,N-dimethylformamide, acetonitrile, tetrahydrofuran, 1,4-dioxane or ethyleneglycol diethyl ether at temperatures between −50° C. and 120° C., but preferably at temperatures between 0° C. and 80° C.

If according to the invention a compound of general formula I is obtained which contains an amino, alkylamino or imino group, this may be converted by acylation or sulphonylation into a corresponding acyl or sulphonyl compound of general formula I, wherein the acylating agents used may be for example carboxylic acid halides, carboxylic acid anhydrides and carboxylic acids with activating agents such as N,N'-carbonyldiimidazole, N,N'-dicyclohexylcarbodiimide or O-(benzotriazol-1-yl)-N,N,N'N'-tetramethyluronium-tetrafluoroborate and sulphonyl halides as sulphonylating agents, and/or if a compound of general formula I is obtained which contains an amino, alkylamino or imino group, it may be converted by alkylation or reductive alkylation into a corresponding alkyl compound of general formula I and/or if a compound of general formula I is obtained which contains an alkoxycarbonyl group, it may be converted by ester cleaving into a carboxylic acid, and/or if a compound of general formula I is obtained which contains an alkoxycarbonyl group, it may be converted by reaction with an amine into a carboxylic acid amide derivative and/or if a compound of general formula I is obtained which contains a carboxy group, it may be converted by reaction with an amine into a carboxylic acid amide derivative.

In the reactions described hereinbefore any reactive groups present such as hydroxy, amino, alkylamino or imino groups may be protected during the reaction by conventional protective groups which are cleaved again after the reaction.

For example a protecting group for a hydroxy group might be the trimethylsilyl, acetyl, trityl, benzyl or tetrahydropyranyl group.

Protecting groups for an amino, alkylamino or imino group might be, for example, the formyl, acetyl, trifluoroacetyl, ethoxycarbonyl, tert.-butoxycarbonyl, benzyloxycarbonyl, benzyl, methoxybenzyl or 2,4-dimethoxybenzyl group.

Any protective group used is optionally subsequently cleaved for example by hydrolysis in an aqueous solvent, e.g. in water, isopropanol/water, acetic acid/water, tetrahydrofuran/water or 1,4-dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

A benzyl, methoxybenzyl or benzyloxycarbonyl group, however, is cleaved by hydrogenolysis, for example, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and under a hydrogen pressure of 1 to 7 bar, but preferably from 3 to 5 bar. A 2,4-dimethoxybenzyl group, however, is preferably cleaved in trifluoroacetic acid in the presence of anisole, thioanisole, pentamethylbenzene or triethylsilane.

A tert.-butyl or tert.-butyloxycarbonyl group is preferably cleaved by treatment with an acid such as trifluoroacetic acid or hydrochloric acid or by treating with iodotrimethylsilane, optionally using a solvent such as methylene chloride, 1,4-dioxane, methanol, isopropanol or diethyl ether.

A trifluoroacetyl group is preferably cleaved by treatment with an acid such as hydrochloric acid, optionally in the presence of a solvent such as acetic acid at temperatures between 50 and 120° C. or by treatment with sodium hydroxide solution, optionally in the presence of a solvent such as tetrahydrofuran at temperatures between 0 and 50° C.

Other suitable protective groups and possible ways of introducing and cleaving them are described for example in "Protective Groups in Organic Synthesis" by Theodora W. Greene and Peter G. M. Wuts, Wiley-VCH, or Philip Kocienski, Protecting Groups, 3rd ed. 2004, THIEME.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)- or (−)-menthyloxycarbonyl.

Furthermore, the compounds of formula I obtained may be converted into the salts thereof, particularly for pharmaceutical use into the physiologically acceptable salts with inorganic or organic acids or bases. Acids which may be used for this purpose include for example hydrochloric acid, hydrobromic acid, sulphuric acid, methanesulphonic acid, ethanesulphonic acid, benzenesulphonic acid, p-toluenesulphonic acid, phosphoric acid, fumaric acid, succinic acid, benzoic acid, salicylic acid, mandelic acid, lactic acid, malonic acid, citric acid, L-malic acid, L-tartaric acid or maleic acid. Suitable bases for this purpose include for example sodium hydroxide solution, potassium hydroxide solution, calcium hydroxide, diethanolamine or N-methyl-D-glucamine.

The compounds of general formulae II to XIV used as starting materials are known from the literature to some extent or may be obtained by methods known from the literature (cf. Examples I to XII), optionally with the additional introduction of protecting groups.

Standard processes for preparing the starting materials are described for example in "March's Advanced Organic Chemistry" by Michael B. Smith and Jerry March, Wiley-VCH or in "Science of Synthesis/Houben-Weyl" published by Thieme.

For example, the compounds of general formula (V) and (VI) may be obtained as follows:

Scheme 1

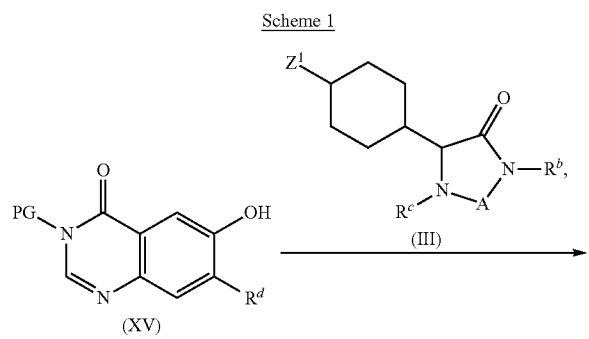

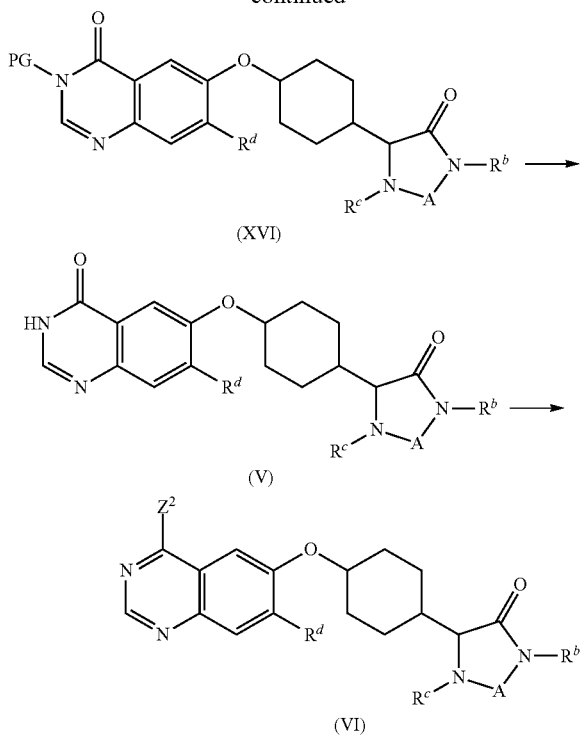

Starting from a compound of general formula (XV), wherein PG denotes a protective group such as for example benzyl, 4-methoxybenzyl or 2,4-dimethoxybenzyl, the reaction is carried out with a compound of general formula (III) analogously to the previously described process a) to obtain a compound of general formula (XVI). The compounds of general formula (XV) are known from the literature (cf. e.g. WO 2004/108664 or WO 2007/003486) or may be obtained by methods known from the literature.

The cleaving of the protective group from a compound of general formula (XVI) to obtain a compound of general formula (V) is carried out, if PG denotes benzyl, with hydrogen, for example, in the presence of a catalyst such as palladium/charcoal (e.g. analogously to Example XI). The cleaving of the protective group if PG denotes 4-methoxybenzyl or 2,4-dimethoxybenzyl may also be carried out oxidatively (e.g. with cerium(IV)-ammonium nitrate or with 2,3-dichloro-5,6-dicyano-1,4-benzoquinone) or with acids (e.g. with trifluoroacetic acid in the presence of anisole, thioanisole, pentamethylbenzene or triethylsilane).

A compound of general formula (V) may then be converted into a compound of general formula (VI), as described in the previous process c). The meanings for $R^b$, $R^c$, $R^d$, A, $Z^1$ and $Z^2$ in the compounds of Scheme 1 are defined as mentioned hereinbefore.

As already mentioned hereinbefore, the compounds of general formula (I) according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosine kinase itself. It is also possible to block the transmission of signals to components located further downstream.

The following Examples are intended to illustrate the present invention without restricting it:

Preparation of the Starting Compounds

Example I

Methyl trans-1-(2-amino-ethylamino)-4-[4-(3-chloro-2-fluoro-phenylamino)-7-methoxy-quinazolin-6-yloxy]-cyclohexanecarboxylate

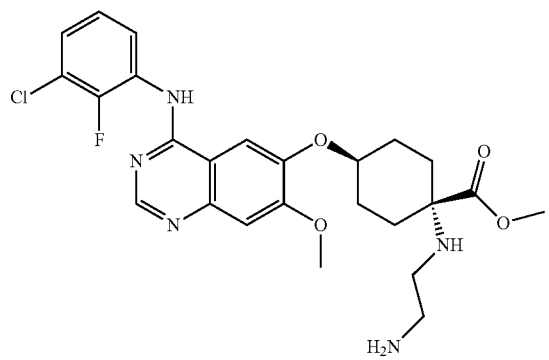 [SMILES: COc1cc2ncnc(Nc3cccc(Cl)c3F)c2cc1O[C@H]1CC[C@@](NCCN)(C(=O)OC)CC1]

3.30 ml trifluoroacetic acid are added to 1.60 g methyl trans-1-(2-tert.-butoxycarbonylamino-ethylamino)-4-[4-(3-chloro-2-fluoro-phenylamino)-7-methoxy-quinazolin-6-yloxy]-cyclohexanecarboxylate in 13 ml methylene chloride. The reaction mixture is stirred for three hours at ambient temperature, then another 1 ml trifluoroacetic acid is added. After a further hour the reaction is finished and the reaction mixture is evaporated down, taken up in methylene chloride and some methanol and made alkaline with 10% potassium carbonate solution. The organic phase is separated off and the aqueous phase is extracted with methylene chloride. The combined organic phases are dried on magnesium sulphate and evaporated down.

Yield: 1.30 g (97% of theory)

Mass spectrum (ESI$^+$): m/z=518, 520 [M+H]$^+$

The following compounds are obtained analogously to Example I:

(1) methyl trans-1-amino-4-[4-(3-chloro-2-fluoro-phenylamino)-7-methoxy-quinazolin-6-yloxy]-cyclohexanecarboxylate

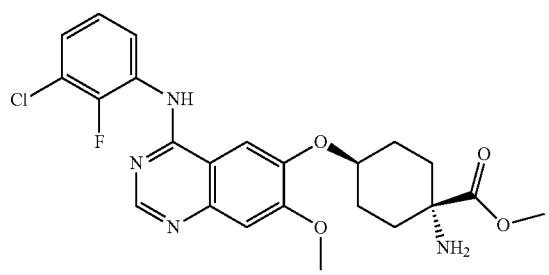 [SMILES: COc1cc2ncnc(Nc3cccc(Cl)c3F)c2cc1O[C@H]1CC[C@@](N)(C(=O)OC)CC1]

Mass spectrum (ESI$^+$): m/z=475, 477 [M+H]$^+$ (2) methyl trans-4-[4-(3-chloro-2-fluoro-phenylamino)-7-methoxy-quinazolin-6-yloxy]-1-(2-methylamino-ethylamino)-cyclohexanecarboxylate

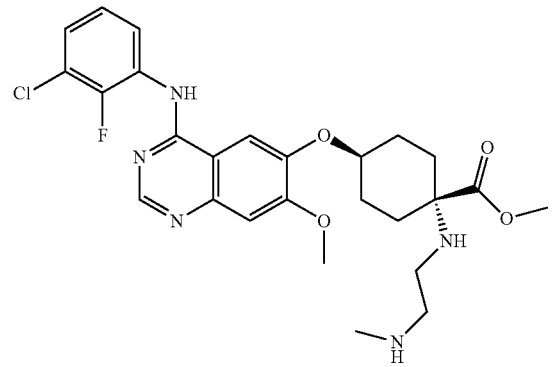 [SMILES: CNCCN[C@]1(C(=O)OC)CC[C@@H](Oc2cc3c(Nc4cccc(Cl)c4F)ncnc3cc2OC)CC1]

Mass spectrum (ESI$^+$): m/z=532, 534 [M+H]$^+$ (3) methyl cis-1-(2-amino-ethylamino)-4-[4-(3-chloro-2-fluoro-phenylamino)-7-methoxy-quinazolin-6-yloxy]-cyclohexanecarboxylate

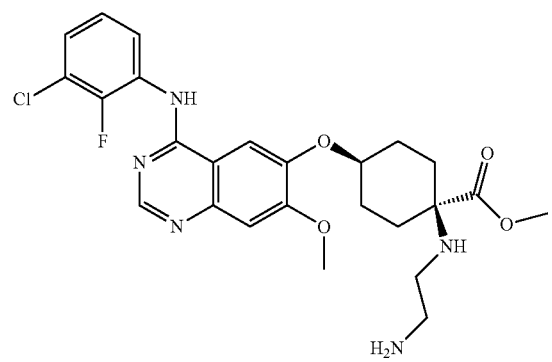 [SMILES: COc1cc2ncnc(Nc3cccc(Cl)c3F)c2cc1O[C@H]1CC[C@](NCCN)(C(=O)OC)CC1]

Example II

Methyl trans-1-(2-tert.-butoxycarbonylamino-ethylamino)-4-[4-(3-chloro-2-fluoro-phenylamino)-7-methoxy-quinazolin-6-yloxy]-cyclohexanecarboxylate

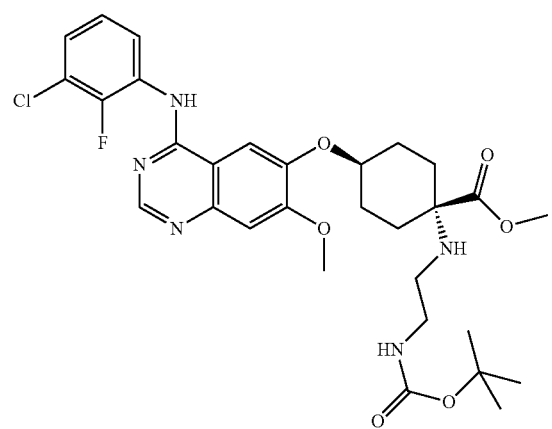 [SMILES: COc1cc2ncnc(Nc3cccc(Cl)c3F)c2cc1O[C@H]1CC[C@@](NCCNC(=O)OC(C)(C)C)(C(=O)OC)CC1]

0.44 g N-tert.-butoxycarbonyl-2-aminoacetaldehyde are added to 1.20 g methyl trans-1-amino-4-[4-(3-chloro-2-fluoro-phenylamino)-7-methoxy-quinazolin-6-yloxy]-cyclohexanecarboxylate in 40 ml of tetrahydrofuran under an argon atmosphere. Then 0.18 ml glacial acetic acid and 0.80 g sodium triacetoxyborohydride are added and the reaction mixture is stirred overnight at ambient temperature. As the reaction has not yet finished, 90 mg N-tert.-butoxycarbonyl-2-aminoacetaldehyde and 200 mg sodium triacetoxyborohydride are both added twice more. After a further night at ambient temperature the reaction is complete. The reaction mixture is diluted with ethyl acetate and combined with sodium hydroxide solution. The organic phase is separated off and the aqueous phase is extracted with ethyl acetate. The combined organic phases are washed with saturated sodium chloride solution, dried on magnesium sulphate and evaporated down. The crude product is further reacted without any further purification.

$R_f$ value: 0.35 (silica gel, methylene chloride/methanol/conc. ammonia=90:10:1)

Mass spectrum (ESI$^+$): m/z=618, 620 [M+H]$^+$

The following compounds are obtained analogously to Example II:

(1) methyl trans-1-[2-(N-tert.-butoxycarbonyl-N-methyl-amino)-ethylamino]-4-[4-(3-chloro-2-fluoro-phenylamino)-7-methoxy-quinazolin-6-yloxy]-cyclohexanecarboxylate

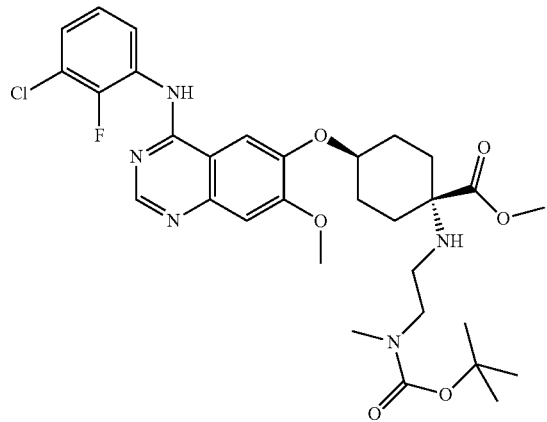 [SMILES: COc1cc2ncnc(Nc3cccc(Cl)c3F)c2cc1O[C@H]1CC[C@@](NCCN(C)C(=O)OC(C)(C)C)(C(=O)OC)CC1]

Mass spectrum (ESI$^+$): m/z=632, 634 [M+H]$^+$ (2) methyl cis-1-(2-tert.-butoxycarbonylamino-ethylamino)-4-[4-(3-chloro-2-fluoro-phenylamino)-7-methoxy-quinazolin-6-yloxy]-cyclohexanecarboxylate

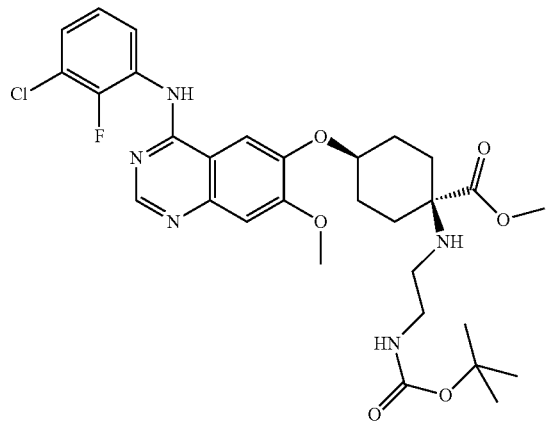 [SMILES: COc1cc2ncnc(Nc3cccc(Cl)c3F)c2cc1O[C@H]1CC[C@](NCCNC(=O)OC(C)(C)C)(C(=O)OC)CC1]

Mass spectrum (ESI$^+$): m/z=618, 620 [M+H]$^+$

Example III

Methyl trans-1-tert.-butoxycarbonylamino-4-[4-(3-chloro-2-fluoro-phenylamino)-7-methoxy-quinazolin-6-yloxy]-cyclohexanecarboxylate

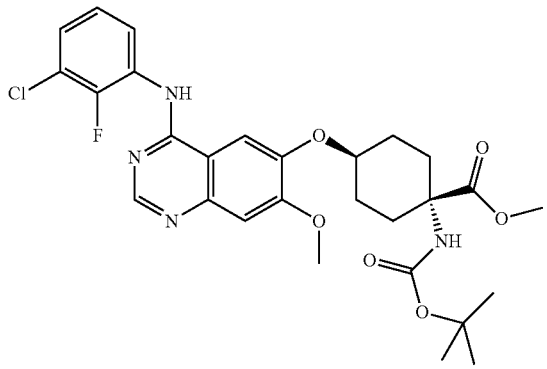 [SMILES: COc1cc2ncnc(Nc3cccc(Cl)c3F)c2cc1O[C@H]1CC[C@@](NC(=O)OC(C)(C)C)(C(=O)OC)CC1]

A mixture of 3.30 g 4-(3-chloro-2-fluoro-phenylamino)-7-methoxy-quinazolin-6-ol in 23 ml N,N-dimethylformamide is heated to 50° C. Then 2.30 g potassium carbonate and 4.40 g methyl cis-1-tert.-butoxycarbonylamino-4-methanesulphonyloxy-cyclohexanecarboxylate are added. The reaction mixture is heated to 80° C. and stirred overnight at this temperature. Then a further 1.00 g methyl cis-1-tert.-butoxycarbonylamino-4-methanesulphonyloxy-cyclohexanecarboxylate and 0.90 g potassium carbonate are added. After another four hours at 80° C. the reaction mixture is cooled to ambient temperature, diluted with ethyl acetate and washed several times with water. The organic phase is washed with saturated sodium chloride solution, dried on magnesium sulphate and evaporated down. The flask residue is purified by chromatography through a silica gel column with methylene chloride/methanol/conc. ammonia (98/2/0.1 to 8/2/0.1).

Yield: 5.50 g (93% of theory)

Mass spectrum (ESI$^+$): m/z=575, 577 [M+H]$^+$

Example IV

Methyl cis-1-tert.-butoxycarbonylamino-4-methanesulphonyloxy-cyclohexanecarboxylate

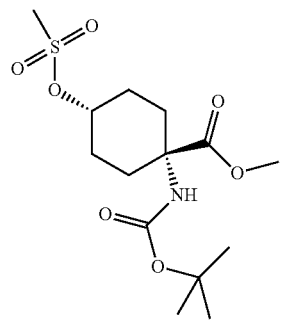 [SMILES: COC(=O)[C@]1(NC(=O)OC(C)(C)C)CC[C@@H](OS(C)(=O)=O)CC1]

1.40 ml methanesulphonic acid chloride are slowly added dropwise to 4.39 g methyl cis-1-tert.-butoxycarbonylamino-4-hydroxy-cyclohexanecarboxylate and 2.80 ml triethylamine in 45 ml methylene chloride while cooling with an ice bath, keeping the temperature below 10° C. Then the reaction mixture is allowed to come up to ambient temperature and stirred overnight. 20 ml of saturated sodium hydrogen carbonate solution are then added, the phases are separated and the aqueous phase is extracted with methylene chloride. The combined organic phases are washed with saturated sodium chloride solution, dried on magnesium sulphate and evaporated down, leaving a viscous oil. The crude product is further reacted without any further purification.

Yield: 5.44 g (96% of theory)

$R_f$ value: 0.50 (silica gel, methylene chloride/methanol=95:5)

Mass spectrum (ESI$^+$): m/z=352 [M+H]$^+$

Example V

Methyl cis-1-tert.-butoxycarbonylamino-4-hydroxy-cyclohexanecarboxylate

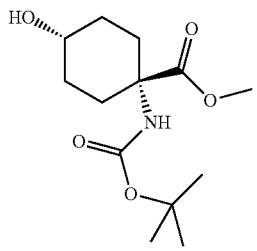 [SMILES: COC(=O)[C@]1(NC(=O)OC(C)(C)C)CC[C@@H](O)CC1]

4.50 g methyl 1-tert.-butoxycarbonylamino-4-oxo-cyclohexanecarboxylate in 45 ml of tetrahydrofuran are combined with 6 ml of water and 630 mg sodiumborohydride under an argon atmosphere. The reaction mixture is stirred for two hours at ambient temperature, diluted with diethyl ether, combined with 1N hydrochloric acid and stirred thoroughly. The organic phase is separated off, washed with 10% potassium carbonate solution and saturated sodium chloride solution, dried on magnesium sulphate and evaporated down. A colourless oil is left, which slowly crystallises overnight.

Yield: 4.39 g (97% of theory)

Mass spectrum (ESI$^+$): m/z=274 [M+H]$^+$

Example VI

Methyl 1-tert.-butoxycarbonylamino-4-oxo-cyclohexanecarboxylate

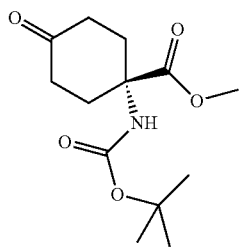

3.90 g potassium carbonate and 1.30 ml methyl iodide are added to 4.65 g 1-tert.-butoxycarbonylamino-4-oxo-cyclohexanecarboxylic acid in 45 ml N,N-dimethylformamide and the reaction mixture is stirred for three hours at ambient temperature. Then the solvent is distilled off using the rotary evaporator and the residue is divided between 10% potassium carbonate solution and diethyl ether. The aqueous phase is separated off and extracted with diethyl ether and the combined organic phases are washed with saturated sodium chloride solution, dried on magnesium sulphate and evaporated down. A colourless oil is left, which slowly crystallises.

Mass spectrum (ESI$^+$): m/z=272 [M+H]$^+$

Example VII

Methyl cis-1-amino-4-[4-(3-chloro-2-fluoro-phenylamino)-7-methoxy-quinazolin-6-yloxy]-cyclohexanecarboxylate

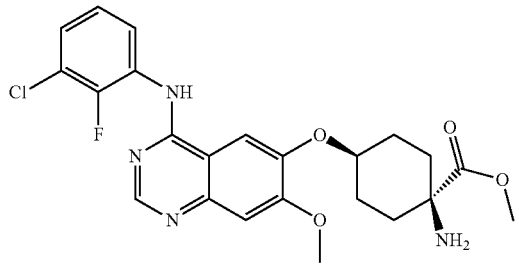 [SMILES: COc1cc2ncnc(Nc3cccc(Cl)c3F)c2cc1O[C@H]1CC[C@](N)(C(=O)OC)CC1]

1.95 g cis/trans-1-amino-4-[4-(3-chloro-2-fluoro-phenylamino)-7-methoxy-quinazolin-6-yloxy]-cyclohexanecarboxylic acid are dissolved in a little methanol and while cooling with an ice bath this mixture is added dropwise to a solution of 700 µl thionyl chloride in 20 ml of methanol. The reaction mixture is heated to ambient temperature overnight with stirring and then refluxed for a further 2 h. As there is still no reaction to be seen, the reaction mixture is cooled, combined with another 700 µl thionyl chloride while cooling with an ice bath and refluxed for another 8 h. As the reaction is still not complete after cooling to ambient temperature, another 700 µl thionyl chloride are added while cooling with an ice bath. After a further 4 h of refluxing the reaction is complete and the solvent is distilled off using the rotary evaporator. The flask residue is divided between methylene chloride and 10% potassium carbonate solution. The aqueous phase is separated off and extracted with methylene chloride. The combined organic phases are dried on magnesium sulphate and evaporated down. The flask residue is chromatographed through a reversed phase column with an acetonitrile/water/ammonia mixture as eluant, in the course of which the cis and trans compounds can be separated.

Yield: 330 mg (16% of theory)

Mass spectrum (ESI⁺): m/z=475, 477 [M+H]⁺

Example VIII cis/trans-1-amino-4-[4-(3-chloro-2-fluoro-phenylamino)-7-methoxy-quinazolin-6-yloxy]-cyclohexanecarboxylic acid

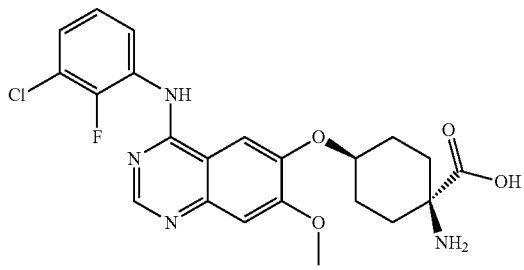

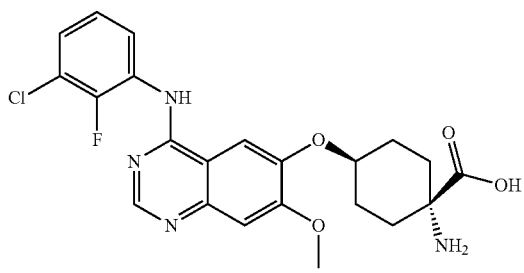

A mixture of 3.00 g syn/anti-8-[4-(3-chloro-2-fluoro-phenylamino)-7-methoxy-quinazolin-6-yloxy]-1,3-diaza-spiro[4.5]decan-2,4-dione and 30 ml of 2 N sodium hydroxide solution is heated to 135° C. with stirring for approx. 25 h. After cooling to ambient temperature the reaction mixture is neutralised with hydrochloric acid. Then the water is distilled off in vacuo using the rotary evaporator, during which time aprecipitate is formed, which is suction filtered and dried. The crude product thus obtained is further reacted without any further purification.

Yield: 1.95 g (69% of theory)

Mass spectrum (ESI⁺): m/z=461, 463 [M+H]⁺

Example IX syn/anti-8-[4-(3-chloro-2-fluoro-phenylamino)-7-methoxy-quinazolin-6-yloxy]-1,3-diaza-spiro[4.5]decan-2,4-dione

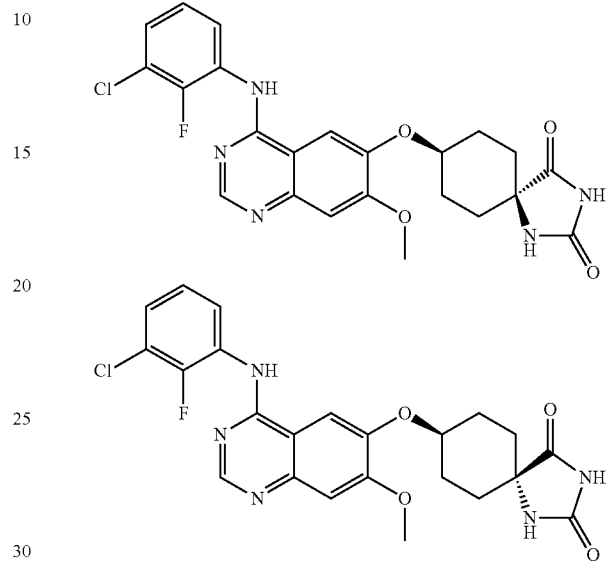

A suspension of 3.00 g 4-[4-(3-chloro-2-fluoro-phenylamino)-7-methoxy-quinazolin-6-yloxy]-cyclohexanone in 30 ml 60% aqueous ethanol is combined with 2.10 g ammonium carbonate and 470 mg potassium cyanide and the reaction mixture is refluxed for 2 h. After cooling to ambient temperature another 0.50 g ammonium carbonate and 100 mg potassium cyanide are added and the reaction mixture is refluxed for a further 2 h. Then the mixture is left overnight to cool to ambient temperature, during which time a light-coloured precipitate is formed. This is suction filtered, washed with water and dried.

Yield: 3.05 g (87% of theory)

Mass spectrum (ESI): m/z=486, 488 [M+H]⁺

Example X

4-[4-(3-chloro-2-fluoro-phenylamino)-7-methoxy-quinazolin-6-yloxy]-cyclohexanone

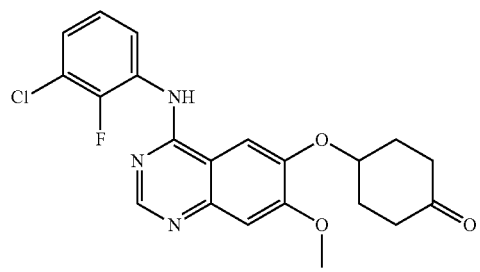 [SMILES: COc1cc2ncnc(Nc3cccc(Cl)c3F)c2cc1OC1CCC(=O)CC1]

3.25 ml phosphorus oxychloride are added dropwise to 6.50 g 6-(1,4-dioxa-spiro[4.5]dec-8-yloxy)-7-methoxy-3H-quinazolin-4-one in 65 ml acetonitrile under an argon atmosphere. Then the reaction mixture is heated to 40° C., combined dropwise with 5.00 ml triethylamine and refluxed for 2 h. After cooling to ambient temperature 1.40 ml triethylamine and 2.60 ml 3-chloro-2-fluoro-aniline, dissolved in 5 ml acetonitrile, are added and the reaction mixture is stirred overnight at 40° C. Then a further 0.70 ml of 3-chloro-2-fluoro-aniline dissolved in 2 ml acetonitrile are added dropwise and the reaction mixture is stirred for a further 10 h. After cooling to ambient temperature the precipitate formed is suction filtered, taken up in 1 N hydrochloric acid, combined with 6 N isopropanolic hydrochloric acid and stirred at ambient temperature until the ketal cleaving is complete. The precipitate formed is suction filtered and combined with methylene chloride and 1 N sodium hydroxide solution. The aqueous phase is separated off and extracted with methylene chloride, the combined extracts are evaporated down and the flask residue is brought to crystallisation with diisopropylether.

Yield: 5.90 g (73% of theory)

Mass spectrum (ESI$^+$): m/z=416, 418 [M+H]$^+$

The following compounds are obtained analogously to Example X:

1) 4-[(2-fluoro-5-methyl-phenyl)amino]-6-(4-oxo-cyclohexyloxy)-7-methoxy-quinazoline

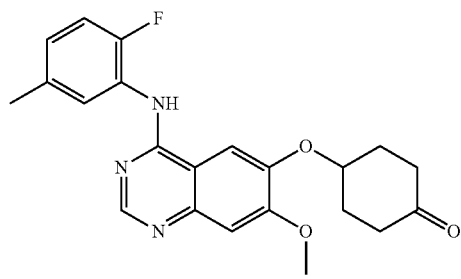 [SMILES: COc1cc2ncnc(Nc3cc(C)ccc3F)c2cc1OC1CCC(=O)CC1]

Mass spectrum (ESI$^+$): m/z=396 [M+H]$^+$ (2) 4-[(2,4-difluoro-3-methyl-phenyl)amino]-6-(4-oxo-cyclohexyloxy)-7-methoxy-quinazoline

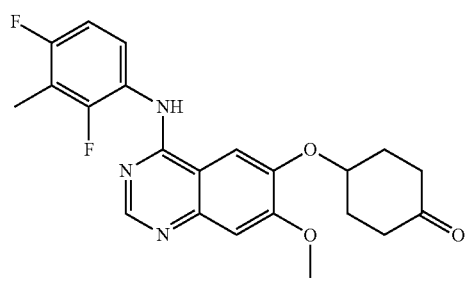 [SMILES: COc1cc2ncnc(Nc3ccc(F)c(C)c3F)c2cc1OC1CCC(=O)CC1]

Mass spectrum (ESI$^+$): m/z=414 [M+H]$^+$ (3) 4-[(2-fluoro-3-methyl-phenyl)amino]-6-(4-oxo-cyclohexyloxy)-7-methoxy-quinazoline

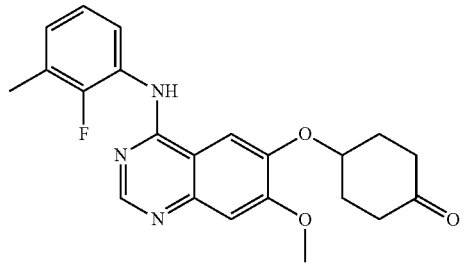 [SMILES: COc1cc2ncnc(Nc3cccc(C)c3F)c2cc1OC1CCC(=O)CC1]

Mass spectrum (ESI$^+$): m/z=396 [M+H]$^+$ (4) 4-[(3-chloro-2-methyl-phenyl)amino]-6-(4-oxo-cyclohexyloxy)-7-methoxy-quinazoline

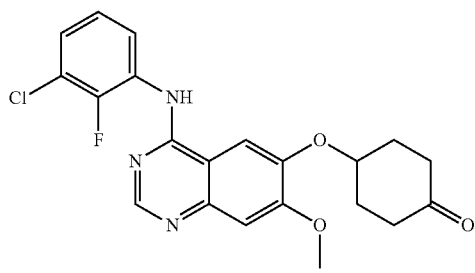 [SMILES: COc1cc2ncnc(Nc3cccc(Cl)c3F)c2cc1OC1CCC(=O)CC1]

Mass spectrum (ESI$^+$): m/z=412, 414 [M+H]$^+$ (5) 4-[(5-chloro-2-fluoro-phenyl)amino]-6-(4-oxo-cyclohexyloxy)-7-methoxy-quinazoline

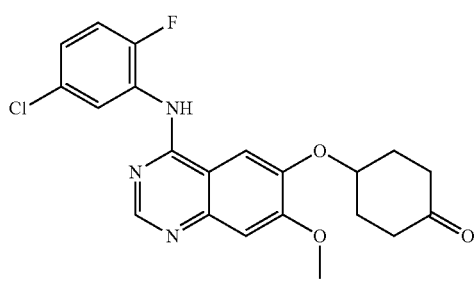 [SMILES: COc1cc2ncnc(Nc3cc(Cl)ccc3F)c2cc1OC1CCC(=O)CC1]

Mass spectrum (ESI$^+$): m/z=416, 418 [M+H]$^+$ (6) 4-[(4-fluoro-3-methyl-phenyl)amino]-6-(4-oxo-cyclohexyloxy)-7-methoxy-quinazoline

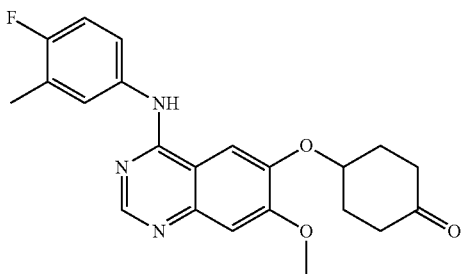 [SMILES: COc1cc2ncnc(Nc3ccc(F)c(C)c3)c2cc1OC1CCC(=O)CC1]

Mass spectrum (ESI⁺): m/z=396 [M+H]⁺

(7) 4-[(3-fluoro-5-methyl-phenyl)amino]-6-(4-oxo-cyclohexyloxy)-7-methoxy-quinazoline

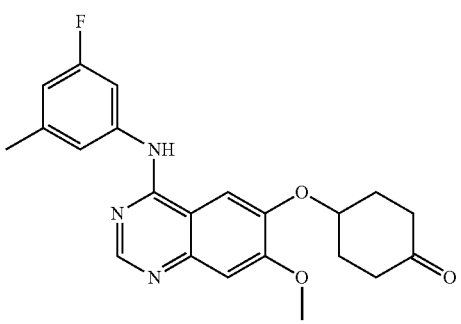 [SMILES: COc1cc2ncnc(Nc3cc(C)cc(F)c3)c2cc1OC1CCC(=O)CC1]

Mass spectrum (ESI⁺): m/z=396 [M+H]⁺

(8) (R)-4-[(1-phenylethyl)amino]-6-(4-oxo-cyclo-hexyloxy)-7-methoxy-quinazoline

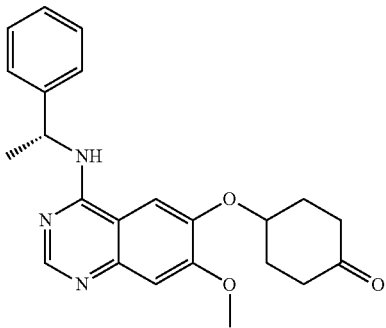 [SMILES: COc1cc2ncnc(N[C@H](C)c3ccccc3)c2cc1OC1CCC(=O)CC1]

Mass spectrum (ESI⁺): m/z=392 [M+H]⁺

Example XI 6-(1,4-Dioxa-spiro[4.5]dec-8-yloxy)-7-methoxy-3H-quinazolin-4-one

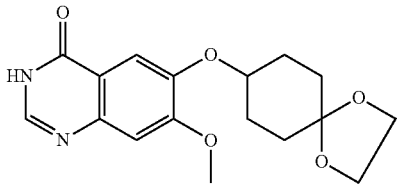 [SMILES: COc1cc2nc[nH]c(=O)c2cc1OC1CCC2(CC1)OCCO2]

27.20 g of 3-benzyl-6-(1,4-dioxa-spiro[4.5]dec-8-yloxy)-7-methoxy-3H-quinazolin-4-one are dissolved in 270 ml glacial acetic acid, combined with 2.70 g palladium on activated charcoal (10%) and hydrogenated at 60° C. until the uptake of hydrogen has ended. Then the glacial acetic acid is distilled off using the rotary evaporator and evaporated off with toluene. The flask residue is mixed with water and made alkaline with saturated sodium hydrogen carbonate solution. The precipitate formed is suction filtered and dried.

Yield: 20.30 g (95% of theory)
Mass spectrum (ESI⁺): m/z=333 [M+H]⁺

Example XII 3-benzyl-6-(1,4-dioxa-spiro[4.5]dec-8-yloxy)-7-methoxy-3H-quinazolin-4-one

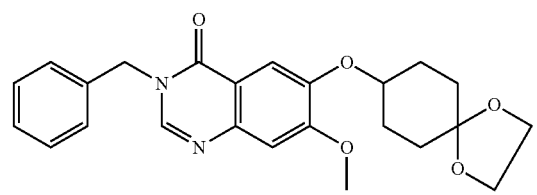 [SMILES: COc1cc2ncn(Cc3ccccc3)c(=O)c2cc1OC1CCC2(CC1)OCCO2]

20.00 g 3-benzyl-6-hydroxy-7-methoxy-3H-quinazolin-4-one in 150 ml N,N-dimethylformamide are heated to 50° C., then 16.00 g potassium carbonate and 20.00 g 1,4-dioxa-spiro[4.5]dec-8-yl methanesulphonate are added and the reaction mixture is stirred overnight at 80° C. Then another 6.00 g potassium carbonate and 8.00 g 1,4-dioxa-spiro[4.5]dec-8-yl methanesulphonate are added and the mixture is stirred for a further 4 h at 80° C. Within the next 24 h a total of a further 6.00 g potassium carbonate and 10.00 g 1,4-dioxa-spiro[4.5]dec-8-yl methanesulphonate are added batchwise until the reaction is complete. After cooling to ambient temperature a total of 450 ml of water are very slowly added dropwise with stirring, whereupon a precipitate is formed which is suction filtered, washed with water and dried.

Yield: 27.20 g (91% of theory)
Mass spectrum (ESI⁺): m/z=423 [M+H]⁺

Preparation of the End Compounds

Example 1 anti-9-[4-(3-chloro-2-fluoro-phenylamino)-7-methoxy-quinazolin-6-yloxy]-1,4-diaza-spiro[5.5]undecan-5-one

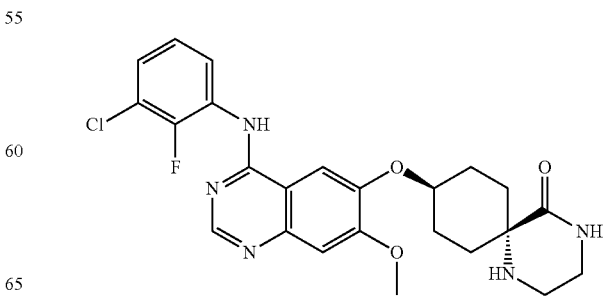

1.30 ml 4 N sodium hydroxide solution are added to 1.30 g methyl trans-1-(2-amino-ethylamino)-4-[4-(3-chloro-2-fluoro-phenylamino)-7-methoxy-quinazolin-6-yloxy]-cyclohexanecarboxylate in 14 ml of methanol and the reaction mixture is stirred for three hours at ambient temperature. Then the solvent is distilled off in vacuo using the rotary evaporator. The flask residue is purified by chromatography through a silica gel column with methylene chloride/methanol/conc. ammonia (98/2/0.1 to 8/2/0.1) as eluant. The product fractions are evaporated down and stirred with diisopropylether. The solid residue is suction filtered and dried.

Yield: 700 mg (57% of theory)

$R_f$ value: 0.30 (silica gel, methylene chloride/methanol/conc. ammonia=90:10:1)

Mass spectrum (ESI$^+$): m/z=486, 488 [M+H]$^+$

The following compounds are obtained analogously to Example 1:

(1) anti-9-[4-(3-chloro-2-fluoro-phenylamino)-7-methoxy-quinazolin-6-yloxy]-4-methyl-1,4-diaza-spiro[5.5]undecan-5-one

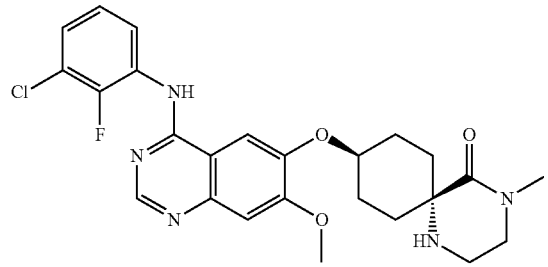 [SMILES: COc1cc2ncnc(Nc3cccc(Cl)c3F)c2cc1O[C@H]1CC[C@@]2(CC1)NCCN(C)C2=O]

Mass spectrum (ESI$^+$): m/z=500, 502 [M+H]$^+$ (2) syn-9-[4-(3-chloro-2-fluoro-phenylamino)-7-methoxy-quinazolin-6-yloxy]-1,4-diaza-spiro[5.5]undecan-5-one

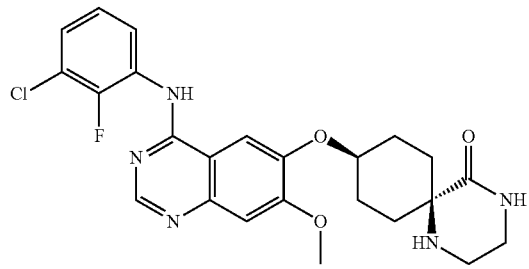 [SMILES: COc1cc2ncnc(Nc3cccc(Cl)c3F)c2cc1O[C@H]1CC[C@]2(CC1)NCCNC2=O]

Mass spectrum (ESI$^+$): m/z=486, 488 [M+H]$^+$

Example 2 anti-9-[4-(3-chloro-2-fluoro-phenylamino)-7-methoxy-quinazolin-6-yloxy]-1-methyl-1,4-diaza-spiro[5.5]undecan-5-one

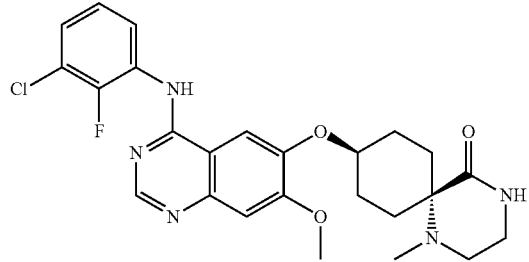 [SMILES: COc1cc2ncnc(Nc3cccc(Cl)c3F)c2cc1O[C@H]1CC[C@]2(CC1)C(=O)NCCN2C]

125 μl of 37% aqueous formaldehyde solution, followed by 50 μl of glacial acetic acid and 280 mg sodium triacetoxyborohydride are added to 400 mg anti-9-[4-(3-chloro-2-fluoro-phenylamino)-7-methoxy-quinazolin-6-yloxy]-1,4-diaza-spiro[5.5]undecan-5-one in 12 ml of tetrahydrofuran. The reaction mixture is stirred overnight at ambient temperature, diluted with ethyl acetate, combined with 1N sodium hydroxide solution and stirred. The organic phase is separated off, washed with water and saturated sodium chloride solution, dried on magnesium sulphate and evaporated down. The flask residue is purified by chromatography through a silica gel column with methylene chloride/methanol/conc. ammonia (99/1/0.2 to 8/2/0.1) as eluant. The crude product is stirred with methanol, suction filtered and dried.

Yield: 230 mg (56% of theory)

Mass spectrum (ESI$^+$): m/z=500, 502 [M+H]$^+$

The following compound is obtained analogously to Example 2:

(1) anti-9-[4-(3-chloro-2-fluoro-phenylamino)-7-methoxy-quinazolin-6-yloxy]-1,4-dimethyl-1,4-diaza-spiro[5.5]undecan-5-one

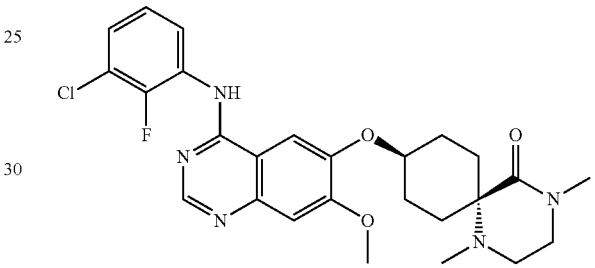

Mass spectrum (ESI$^+$): m/z=514, 516 [M+H]$^+$

Example 3 syn/anti-8-[4-(3-chloro-2-fluoro-phenylamino)-7-methoxy-quinazolin-6-yloxy]-1,3-diaza-spiro[4.5]decan-2,4-dione

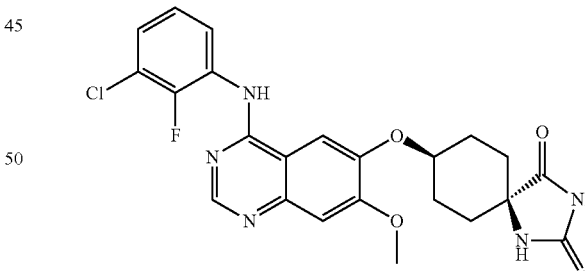

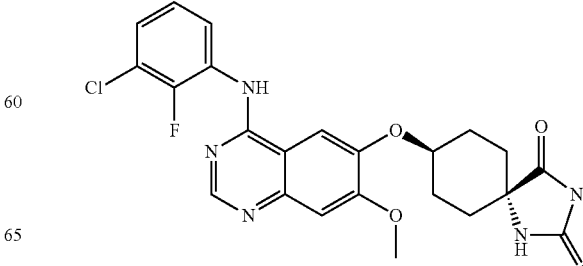

A suspension of 3.00 g 4-[4-(3-chloro-2-fluoro-phenylamino)-7-methoxy-quinazolin-6-yloxy]-cyclohexanone in 30 ml of 60% aqueous ethanol is combined with 2.10 g ammonium carbonate and 470 mg potassium cyanide and the reaction mixture is refluxed for 2 h. After cooling to ambient temperature a further 0.50 g ammonium carbonate and 100 mg potassium cyanide are added and the reaction mixture is refluxed for a further 2 h. Then it is left overnight to cool to ambient temperature, during which time a light-coloured precipitate is formed. This is suction filtered, washed with water and dried.

Yield: 3.05 g (87% of theory)
Mass spectrum (ESI$^+$): m/z=486, 488 [M+H]$^+$

Biological Test

The biological properties of the new compounds are investigated as follows, for example:

The inhibition of the EGF-R-mediated signal transmission can be demonstrated e.g. with cells which express human EGF-R and whose survival and proliferation depend on stimulation by EGF or TGF-alpha. A murine haematopoietic cell line is genetically modified so as to express functional human EGF-R. The proliferation of this cell line can therefore be stimulated by EGF.

The test is carried out as follows:

The cells are cultivated in RPMI/1640 medium. The proliferation is stimulated with 20 ng/ml of human EGF (Promega). To investigate the inhibitory activity of the compounds according to the invention these compounds are dissolved in 100% dimethylsulphoxide (DMSO) and added to the cultures in various dilutions, the maximum DMSO concentration being 1%. The cultures are incubated for 48 hours at 37° C.

In order to determine the inhibitory activity of the compounds according to the invention the relative cell number is measured in O.D. Units using the Cell Titer 96™ AQueous Non-Radioactive Cell Proliferation Assay (Promega). The relative cell number is calculated as a percentage of the control and the concentration of active substance which inhibits the proliferation of the cells by 50% (IC50) is derived therefrom.

The compounds of general formula (I) according to the invention exhibit IC50 values of <10 micromolar, preferably <1 micromolar, for example.

| Compound (Example No.) | Inhibition of EGFR-dependent proliferation IC$_{50}$ [nM] |
| --- | --- |
| 1 | 4 |
| 1(1) | 2 |
| 1(2) | 2 |
| 2 | 1 |
| 2(1) | 2 |

Indications

As has been found, the compounds of formula (I) are characterised by their versatility in the therapeutic field. Particular mention should be made of the possible applications for which the compounds of formula (I) according to the invention are preferably used on the basis of their pharmaceutical efficacy as tyrosine inhibitors.

The compounds of general formula (I) according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis). Moreover, EGFR inhibitors are useful for the treatment of viral infections in which the virus uses the signal transduction pathway of the EGFR for entering or attacking the cell or for replication or for the reaction of the host to the virus.

The compounds according to the invention are also useful for preventing and treating diseases of the airways and lungs which are accompanied by increased or altered production of mucus caused by stimulation of tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways. The compounds are also useful for treating viral or bacterial complications and for treating viral or bacterial infections of the airways or lungs when tyrosine kinase is activated during the entry, replication or tissue reaction of the host.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, the treatment of nasal polyps, etc.

The compounds of formula (I) may be used on their own or in combination with other active substances of formula (I). Optionally the compounds of formula (I) may also be used in combination with W, wherein W denotes a pharmacologically active substance and is selected (for example) from among the betamimetics, anticholinergics, corticosteroids, PDE4-inhibitors, LTD4-receptor (cysLT1, cysLT2, cysLT3) antagonists, EGFR-inhibitors, dopamine-agonists, H1-antihistamines, PAF-antagonists, SYK-inhibitors, PDE3 inhibitors, lipoxin A4 derivatives, FPRL1 modulators, LTB4-receptor (BLT1, BLT2) antagonists, histamine H1 receptor antagonists, histamine H4 receptor antagonists, PI3 kinase inhibitors, inhibitors of non-receptor tyrosine kinases such as for example LYN, LCK, SYK, ZAP-70, FYN, BTK or ITK, inhibitors of MAP kinases such as for example p38, ERK1, ERK2, JNK1, JNK2, JNK3 or SAP, inhibitors of the NF-kappaB signal pathway such as for example IKK kinase inhibitors, iNOS inhibitors, MRP4 inhibitors, leukotriene biosynthesis inhibitors such as for example 5-lipoxygenase (5-LO) inhibitors, cPLA2 inhibitors, leukotriene A4 hydrolase inhibitors or FLAP inhibitors, non-steroidal anti-inflammatory agents (NSAIDs), CRTH2 antagonists, DP1-receptor modulators, thromboxane receptor antagonists, chemokine receptor antagonists of CCR1, CCR2, CCR2A, CCR2B, CCR4, CCR5, CCR6, CCR7, CCR8, CCR9, CCR10, CCR11, CXCR1, CXCR2, CXCR3, CXCR4, CXCR5, CXCR6, CX3CR1, neurokinin (NK1, NK2) antagonists, sphingosine 1-phosphate receptor modulators, modulators of adenosine receptors, modulators of purinergic receptors such as for example P2X7, histone deacetylase (HDAC) activators, bradykinin (BK1, BK2) antagonists, TACE inhibitors, mucoregulators, PPAR gamma agonists, Rho kinase inhibitors, interleukin 1-beta converting enzyme (ICE) inhibitors, toll-like receptor (TLR) modulators, HMG-CoA reductase inhibitors, VLA-4 antagonists, ICAM-1 inhibitors, SHIP agonists, TNFalpha antagonists, GABAa receptor antagonists, immunotherapeutics, substances to counteract swelling of the airways and antitussive agents. In addition, double or triple combinations of W may be combined with the compounds of formula (I). Examples of combinations of W with the compounds of formula 1 would include:

W denotes a betamimetic, combined with an anticholinergic, corticosteroid, PDE4-inhibitor, EGFR-inhibitor, p38 MAP kinase inhibitor or LTD4-receptor antagonist, W denotes an anticholinergic, combined with a betamimetic, corticosteroid, PDE4-inhibitor, EGFR-inhibitor, p38 MAP kinase inhibitor or LTD4-receptor antagonist, W denotes a corticosteroid, combined with a PDE4-inhibitor, EGFR-inhibitor or LTD4-receptor antagonist, W denotes a PDE4-inhibitor, combined with an EGFR-inhibitor, p38 MAP kinase inhibitor or LTD4-receptor antagonist or p38 MAP kinase inhibitor W denotes an EGFR-inhibitor, combined with an anticholinergic.

Examples of betamimetics which may be used here preferably include compounds which are selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, and 3-(4-{6-[2-hydroxy-2-(4-hydroxy-3-hydroxymethyl-phenyl)-ethylamino]-hexyloxy}-butyl)-benzyl-sulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol, 6-hydroxy-8-{1-hydroxy-2-[2-(4-methoxy-phenyl)-1,1-dimethyl-ethylamino]-ethyl}-4H-benzo[1.4]oxazin-3-one, 6-hydroxy-8-{1-hydroxy-2-[2-(4-phenoxy-acetate ethyl)-1,1-dimethyl-ethylamino]-ethyl}-4H-benzo[1.4]oxazin-3-one, 6-hydroxy-8-{1-hydroxy-2-[2-(4-phenoxy-essigsäure)-1,1-dimethyl-ethylamino]-ethyl}-4H-benzo[1.4]oxazin-3-one, 8-{2-[1,1-dimethyl-2-(2.4.6-trimethylphenyl)-ethylamino]-1-hydroxy-ethyl}-6-hydroxy-4H-benzo[1.4]oxazin-3-one, 6-hydroxy-8-{1-hydroxy-2-[2-(4-hydroxy-phenyl)-1,1-dimethyl-ethylamino]-ethyl}-4H-benzo[1.4]oxazin-3-one, 6-hydroxy-8-{1-hydroxy-2-[2-(4-isopropyl-phenyl)-1.1 dimethyl-ethylamino]-ethyl}-4H-benzo[1.4]oxazin-3-one, 8-{2-[2-(4-ethyl-phenyl)-1,1-dimethyl-ethylamino]-1-hydroxy-ethyl}-6-hydroxy-4H-benzo[1.4]oxazin-3-one, 8-{2-[2-(4-ethoxy-phenyl)-1,1-dimethyl-ethylamino]-1-hydroxy-ethyl}-6-hydroxy-4H-benzo[1.4]oxazin-3-one, 4-(4-{2-[2-hydroxy-2-(6-hydroxy-3-oxo-3,4-dihydro-2H-benzo[1.4]oxazin-8-yl)-ethylamino]-2-methyl-propyl}-phenoxy)-butyric acid, 8-{2-[2-(3,4-difluoro-phenyl)-1,1-dimethyl-ethylamino]-1-hydroxy-ethyl}-6-hydroxy-4H-benzo[1.4]oxazin-3-one, 1-(4-ethoxy-carbonylamin-3-cyano-5-fluorophenyl)-2-(tert-butylamino) ethanol, 2-hydroxy-5-(1-hydroxy-2-{2-[4-(2-hydroxy-2-phenyl-ethylamino)-phenyl]-ethylamino}-ethyl)-benzaldehyde, N-[2-hydroxy-5-(1-hydroxy-2-{2-[4-(2-hydroxy-2-phenyl-ethylamino)-phenyl]-ethylamino}-ethyl)-phenyl]-formamide, 8-hydroxy-5-(1-hydroxy-2-{2-[4-(6-methoxy-biphenyl-3-ylamino)-phenyl]-ethylamino}-ethyl)-1H-quinolin-2-one, 8-hydroxy-5-[1-hydroxy-2-(6-phenethylamino-hexylamino)-ethyl]-1H-quinolin-2-one, 5-[2-(2-{4-[4-(2-amino-2-methyl-propoxy)-phenylamino]-phenyl}-ethylamino)-1-hydroxy-ethyl]-8-hydroxy-1H-quinolin-2-one, [3-(4-{6-[2-hydroxy-2-(4-hydroxy-3-hydroxymethyl-phenyl)-ethylamino]-hexyloxy}-butyl)-5-methyl-phenyl]-urea, 4-(2-{6-[2-(2,6-dichloro-benzyloxy)-ethoxy]-hexylamino}-1-hydroxy-ethyl)-2-hydroxymethyl-phenol, 3-(4-{6-[2-hydroxy-2-(4-hydroxy-3-hydroxymethyl-phenyl)-ethylamino]-hexyloxy}-butyl)-benzenesulphonamide, 3-(3-{7-[2-hydroxy-2-(4-hydroxy-3-hydroxymethyl-phenyl)-ethylamino]-heptyloxy}-propyl)-benzenesulphonamide, 4-(2-{6-[4-(3-cyclopentanesulphonyl-phenyl)-butoxy]-hexylamino}-1-hydroxy-ethyl)-2-hydroxymethyl-phenol, N-adamantan-2-yl-2-(3-{2-[2-hydroxy-2-(4-hydroxy-3-hydroxymethyl-phenyl)-ethylamino]-propyl}-phenyl)-acetamide, (R,S)-4-(2-{[6-(2,2-difluoro-4-phenylbutoxy)hexyl]amino}-1-hydroxy-ethyl)-2-(hydroxymethyl)phenol, (R,S)-4-(2-{[6-(2,2-difluoro-2-phenylethoxy)hexyl]amino}-1-hydroxy-ethyl)-2-(hydroxymethyl)phenol, (R,S)-4-(2-{[4.4-difluoro-6-(4-phenylbutoxy)hexyl]amino}-1-hydroxy-ethyl)-2-(hydroxymethyl)phenol, (R,S)-4-(2-{[6-(4.4-difluoro-4-phenylbutoxy)hexyl]amino}-1-hydroxy-ethyl)-2-(hydroxymethyl)phenol, (R,S)-5-(2-{[6-(2,2-difluoro-2-phenylethoxy)hexyl]amino}-1-hydroxy-ethyl)-8-hydroxyquinolin-2(1H)-one, (R,S)-[2-({6-[2,2-difluoro-2-(3-methylphenyl)ethoxy]hexyl}amino)-1-hydroxyethyl]-2-(hydroxymethyl)phenol, 4-(1R)-2-{[6-(2,2-difluoro-2-phenylethoxy)hexyl]amino}-1-hydroxyethyl)-2-(hydroxymethyl)phenol, (R,S)-2-(hydroxymethyl)-4-(1-hydroxy-2-{[4.4.5I5-tetrafluoro-6-(3-phenylpropoxy)hexyl]amino}ethyl)phenol, (R,S)-[5-(2-{[6-(2,2-difluoro-2-phenylethoxy)hexyl]amino}-1-hydroxy-ethyl)-2-hydroxyphenyl]formamide, (R,S)-4-[2-({6-[2-(3-bromophenyl)-2,2-difluoroethoxy]hexyl}amino)-1-hydroxyethyl]-2-(hydroxymethyl)phenol, (R,S)—N-[3-(1,1-difluoro-2-{[6-({2-hydroxy-2-[4-hydroxy-3-(hydroxymethyl)phenyl]ethyl}amino)hexyl]oxy}ethyl)phenyl]urea, 3-[3-(1,1-difluoro-2-{[6-({2-hydroxy-2-[4-hydroxy-3-(hydroxymethyl)phenyl]ethyl}-amino)hexyl]oxy}ethyl)phenyl]imidazolidine-2,4-dione, (R,S)-4-[2-({6-[2,2-difluoro-2-(3-methoxyphenyl)ethoxy]hexyl}amino)-1-hydroxyethyl]-2-(hydroxymethyl)phenol, 5-((1R)-2-{[6-(2,2-difluoro-2-phenylethoxy)hexyl]amino}-1-hydroxyethyl)-8-hydroxyquinolin-2(1H)-one, 4-((1R)-2-{[4.4-difluoro-6-(4-phenylbutoxy)hexyl]amino}-1-hydroxy-ethyl)-2-(hydroxymethyl)phenol, (R,S)-4-(2-{[6-(3.3-difluoro-3-phenylpropoxy)hexyl]amino}-1-hydroxy ethyl)-2-(hydroxymethyl)phenol, (R,S)-2-({6-(2,2-difluoro-2-phenylethoxy)-4.4-difluorohexyl]amino}-1-hydroxyethyl)-2-(hydroxymethyl)phenol and (R,S)-4-(2-{[6-(2,2-difluoro-3-phenylpropoxy)hexyl]amino}-1-hydroxy-ethyl)-2-(hydroxymethyl)phenol, optionally in the form of ihrer racemates, enantiomers, diastereomers and optionally in the form of the pharmacologically acceptable acid addition salts, solvates or hydrates thereof. Preferably, according to the invention, the acid addition salts of the betamimetics are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Examples of anticholinergics which may be used here preferably include compounds which are selected from among: tiotropium salts, preferably the bromide salt, oxitropium salts, preferably the bromide salt, flutropium salts, preferably the bromide salt, ipratropium salts, preferably the bromide salt, aclidinium salts, preferably the bromide salt, glycopyrronium salts, preferably the bromide salt, trospium salts, preferably the chloride salt, tolterodine, (3R)-1-phenethyl-3-(9H-xanthen-9-carbonyloxy)-1-azoniabicyclo[2,2,2]octane-salts. In the above-mentioned salts the cations are the pharmacologically active constituents. As X$^-$ anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other specified compounds are: tropenol 2,2-diphenylpropionate methobromide, scopine 2,2-diphenylpropionate methobromide, scopine 2-fluoro-2,2-diphenylacetate methobromide, tropenol 2-fluoro-2,2-diphenylacetate methobromide, tropenol 3,3',4,4'-tetrafluorobenzilate methobromide, scopine 3,3',4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide; tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide; tropenol 9-methyl-fluorene-9-carboxylate methobromide, scopine 9-methyl-fluorene-9-carboxylate methobromide, cyclopropyltropine benzilate methobromide, cyclopropyltropine 2,2-diphenylpropionate methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, cyclopropyltropine methyl 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate-methobromide, scopine 9-methyl-xanthene-9-carboxylate-methobromide, tropenol 9-ethyl-xanthene-9-carboxylate methobromide, tropenol 9-difluoromethyl-xanthene-9-carboxylate methobromide, scopine 9-hydroxymethyl-xanthene-9-carboxylate methobromide.

The above-mentioned compounds may also be used as salts within the scope of the present invention, while instead of the methobromide, the metho-X salts may be used wherein X may have the meanings given hereinbefore for X$^-$.

Compounds which may be used as corticosteroids are preferably those selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, tipredane and pregna-1,4-diene-3.20-dione, 6-fluoro-11-hydroxy-16,17-[(1-methylethylidene)bis(oxy)]-21-[[4-[(nitrooxy)methyl]benzoyl]oxy], (6α,11β,16α)-(9Cl) (NCX-1024), 16,17-butylidenedioxy-6,9-difluoro-11-hydroxy-17-(methylthio)androst-4-en-3-one (RPR-106541), (S)-fluoromethyl 6,9-difluoro-17-[(2-furanylcarbonyl)oxy]-11-hydroxy-16-methyl-3-oxo-androsta-1,4-diene-17-carbothionate, (S)-(2-oxo-tetrahydro-furan-3S-yl) 6,9-difluoro-11-hydroxy-16-methyl-3-oxo-17-propionyloxy-androsta-1,4-dien-17-carbothionate, cyanomethyl 6alpha,9alpha-difluoro-11beta-hydroxy-16alpha-methyl-3-oxo-17alpha-(2,2,3,3-tetramethylcyclopropylcarbonyl)oxy-androsta-1,4-diene-17beta-carboxylate, optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, apremilast, arofyllin, atizoram, oglemilastum, tetomilast, and 5-[(N-(2,5-dichloro-3-pyridinyl)-carboxamid]-8-methoxy-quinoline (D-4418), 5-N-(3.5-dichloro-1-oxido-4-pyridinyl)-carboxamid]-8-methoxy-2-(trifluoromethyl)-quinoline (D-4396 (Sch-351591)), N-(3,5-dichloropyrid-4-yl)-[1-(4-fluorobenzyl)-5-hydroxy-indol-3-yl]glyoxylic acid amide (AWD-12-281 (GW-842470)), 9-[(2-fluorophenyl)methyl]-N-methyl-2-(trifluoromethyl)-9H-purin-6-amine (NCS-613), 4-[(2R)-2-[3-(cyclopentyloxy)-4-methoxyphenyl]-2-phenylethyl]-pyridine (CDP-840), N-[(3R)-3,4,6,7-tetrahydro-9-methyl-4-oxo-1-phenylpyrrolo[3.2.1-jk][1.4]benzodiazepin-3-yl]-4-pyridinecarboxamide (PD-168787), 4-[6,7-diethoxy-2.3-bis(hydroxymethyl)-1-naphthalenyl]-1-(2-methoxyethyl)-2(1H)-pyridinone (T-440), 2-[4-[6,7-diethoxy-2,3-bis(hydroxymethyl)-1-naphthalenyl]-2-pyridinyl]-4-(3-pyridinyl)-1(2H)-phthalazinone (T-2585), (3-(3-cyclopenyloxy-4-methoxybenzyl)-6-ethylamino-8-isopropyl-3H-purine (V-11294A), beta-[3-(cyclopentyloxy)-4-methoxyphenyl]-1,3-dihydro-1,3-dioxo-2H-isoindole-2-propanamide (CDC-801), imidazo[1,5-a]pyrido[3.2-e]pyrazin-6(5H)-one, 9-ethyl-2-methoxy-7-methyl-5-propyl-(D-22888), 5-[3-(cyclopentyloxy)-4-methoxyphenyl]-3-[(3-methylphenyl)methyl], (3S,5S)-2-piperidinone (HT-0712), 4-[1-[3,4-bis(difluoromethoxy)phenyl]-2-(3-methyl-1-oxido-4-pyridinyl)ethyl]-alpha,alpha-bis(trifluoromethyl)-benzenemethanol (L-826141), N-(3,5-dichloro-1-oxo-pyridin-4-yl)-4-difluoromethoxy-3-cyclopropylmethoxybenzamide, (−)p-[(4aR*.10bS*)-9-ethoxy-1,2,3,4,4a,10b-hexahydro-8-methoxy-2-methylbenzo[s][1.6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-5-methyl-isothioureido]benzyl)-2-pyrrolidone and cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl) cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene] acetate, (S)-(−)-ethyl[4-(3-cyclopentyloxy-4- methoxyphenyl)pyrrolidin-2-ylidene]acetate, 9-cyclopentyl-5.6-dihydro-7-ethyl-3-(2-thienyl)-9H-pyrazolo[3,4-c]-1,2,4-triazolo[4.3-a]pyridine and 9-cyclopentyl-5,6-dihydro-7-ethyl-3-(tert-butyl)-9H-pyrazolo[3,4-c]-1,2,4-triazolo[4.3-a]pyridine, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

EGFR-inhibitors which may be used are preferably compounds selected from among cetuximab, trastuzumab, panitumumab (=ABX-EGF), Mab ICR-62, gefitinib, canertinib, erlotinib, 4-[(3-chloro-4-fluorophenyl)amino]-6-{[4-(morpholin-4-yl)-1-oxo-2-buten-1-yl]amino}-7-cyclopropyl-methoxy-quinazoline, 4-[(3-chloro-4-fluorophenyl)amino]-6-{[4-(N,N-diethylamino)-1-oxo-2-buten-1-yl]amino}-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-cyclopentyloxy-quinazoline, 4-[(R)-(1-phenyl-ethyl)amino]-6-{[4-(N,N-bis-(2-methoxy-ethyl)-amino)-1-oxo-2-buten-1-yl]amino}-7-cyclopropyl-methoxy-quinazoline, 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline, 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline, 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N-cyclopropyl-N-methyl-amino)-1-oxo-2-buten-1-yl]amino}-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline, 4-[(3-ethynyl-phenyl)amino]-6,7-bis-(2-methoxy-ethoxy)-quinazoline, 4-[(3-chloro-4-fluorophenyl)amino]-7-[3-(morpholin-4-yl)-propyloxy]-6-[(vinylcarbonyl)amino]-quinazoline, 4-[(R)-(1-phenyl-ethyl)amino]-6-(4-hydroxy-phenyl)-7H-pyrrolo[2,3-d]pyrimidin, 3-cyano-4-[(3-chloro-4-fluorophenyl)amino]-6-{[4-(N,N-dimethylamino)-1-oxo-2-buten-1-yl]amino}-7-ethoxy-quinoline, 4-{[3-chloro-4-(3-fluoro-benzyloxy)-phenyl]amino}-6-(5-{[(2-methanesulphonyl-ethyl)amino]methyl}-furan-2-yl)quinazoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline, 4-[(3-ethynyl-phenyl)amino]-6-{[4-(5.5-dimethyl-2-oxo-morpholin-4-yl)-1-oxo-2-buten-1-yl]amino}-quinazoline, 4-[(3-chloro-4-fluoro-phenyl)amino]-6-[2-(2,2-dimethyl-6-oxo-morpholin-4-yl)-ethoxy]-7-methoxy-quinazoline, 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline, 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-[1-(tert.-butyloxycarbonyl)-piperidin-4-yloxy]-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3-chloro-4-fluoro-phenyl)amino]-6-(1-methyl-piperidin-4-yloxy)-7-methoxy-quinazoline, 4-[(3-chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(methoxymethyl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-((S)-tetrahydrofuran-3-yloxy)-7-hydroxy-quinazoline, 4-[(3-chloro-4-fluoro-phenyl)amino]-6-(tetrahydropyran-4-yloxy)-7-(2-methoxy-ethoxy)-quinazoline, 4-[(3-chloro-4-fluoro-phenyl)amino]-6-{trans-4-[(dimethylamino)sulphonylamino-cyclohexan-1-yloxy}-7-methoxy-quinazoline, 4-[(3-chloro-4-fluoro-phenyl)amino]-6-{trans-4-[(morpholin-4-yl)carbonylamino]-cyclohexan-1-yloxy}-7-methoxy-quinazoline, 4-[(3-chloro-4-fluoro-phenyl)amino]-6-{trans-4-[(morpholin-4-yl)sulphonylamino-cyclohexan-1-yloxy}-7-methoxy-quinazoline, 4-[(3-chloro-4-fluoro-phenyl)amino]-6-(tetrahydropyran-4-yloxy)-7-(2-acetylamino-ethoxy)-quinazoline, 4-[(3-chloro-4-fluoro-phenyl)amino]-6-(tetrahydropyran-4-yloxy)-7-(2-methanesulphonylamino-ethoxy)-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(1-aminocarbonylmethyl-piperidin-4-yloxy)-7-methoxy-quinazoline, 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)

carbonyl]-N-methyl-amino}-cyclohexan-1-yloxy)-7-methoxy-quinazoline, 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline, 4-[(3-chloro-4-fluoro-phenyl)amino]-6-(trans-4-ethansulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-ethoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-chloro-4-fluoro-phenyl)amino]-6-(cis-4-acetylamino-cyclohexan-1-yloxy)-7-methoxy-quinazoline, 4-[(3-ethynyl-phenyl)amino]-6-[1-(tert.-butyloxycarbonyl)-piperidin-4-yloxy]-7-methoxy-quinazoline, 4-[(3-ethynyl-phenyl)amino]-6-(tetrahydropyran-4-yloxy)-7-methoxy-quinazoline, 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline, 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]-piperidin-4-yloxy}-7-methoxy-quinazoline, 4-[(3-chloro-4-fluoro-phenyl)amino]-6-{1-[(morpholin-4-yl)carbonyl]-piperidin-4-yloxy}-7-(2-methoxy-ethoxy)-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7(2-methoxy-ethoxy)-quinazoline, 4-[(3-chloro-4-fluoro-phenyl)amino]-6-(1-isopropyloxycarbonyl-piperidin-4-yloxy)-7-methoxy-quinazoline, 4-[(3-chloro-4-fluoro-phenyl)amino]-6-(cis-4-methylamino-cyclohexan-1-yloxy)-7-methoxy-quinazoline, 4-[(3-chloro-4-fluoro-phenyl)amino]-6-{cis-4-[N-(2-methoxy-acetyl)-N-methyl-amino]-cyclohexan-1-yloxy}-7-methoxy-quinazoline, 4-[(3-ethynyl-phenyl)amino]-6-(piperidin-4-yloxy)-7-methoxy-quinazoline, 4-[(3-ethynyl-phenyl)amino]-6-[1-(2-methoxy-acetyl)-piperidin-4-yloxy]-7-methoxy-quinazoline, 4-[(3-ethynyl-phenyl)amino]-6-{1-[(morpholin-4-yl)carbonyl]-piperidin-4-yloxy}-7-methoxy-quinazoline, 4-[(3-chloro-4-fluoro-phenyl)amino]-6-{1-[(cis-2,6-dimethyl-morpholin-4-yl)carbonyl]-piperidin-4-yloxy}-7-methoxy-quinazoline, 4-[(3-chloro-4-fluoro-phenyl)amino]-6-{1-[(2-methyl-morpholin-4-yl)carbonyl]-piperidin-4-yloxy}-7-methoxy-quinazoline, 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-{1-[(2-methoxyethyl)carbonyl]-piperidin-4-yloxy}-7-methoxy-quinazoline, 4-[(3-chloro-4-fluoro-phenyl)amino]-6-{1-[(3-methoxypropyl-amino)-carbonyl]-piperidin-4-yloxy}-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, 3-cyano-4-[(3-chloro-4-fluorophenyl)amino]-6-{[4-(N,N-dimethylamino)-1-oxo-2-buten-1-yl]amino}-7-ethoxy-quinoline; [4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-7-(2-{4-[(S)-(2-oxo-tetrahydrofuran-5-yl)carbonyl]-piperazin-1-yl}-ethoxy)-6-[(vinylcarbonyl)amino]-quinazoline, 4-[(3-chloro-4-fluoro-phenyl)amino]-7-[2-((S)-6-methyl-2-oxo-morpholin-4-yl)-ethoxy]-6-[(vinylcarbonyl)amino]-quinazoline, 4-[(3-chloro-4-fluoro-phenyl)amino]-7-[4-((R)-6-methyl-2-oxo-morpholin-4-yl)-butyloxy]-6-[(vinylcarbonyl)amino]-quinazoline, 4-[(3-chloro-4-fluoro-phenyl)amino]-7-[4-((S)-6-methyl-2-oxo-morpholin-4-yl)-butyloxy]-6-[(vinylcarbonyl)amino]-quinazoline, and 4-[(3-chloro-4-fluorophenyl)amino]-6-[(4-{N-[2-(ethoxycarbonyl)-ethyl]-N-[(ethoxycarbonyl)methyl]amino}-1-oxo-2-buten-1-yl)amino]-7-cyclopropyl-methoxy-quinazoline, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Dopamine receptor agonists used here are preferably compounds selected from among bromocriptin, cabergolin, alpha-dihydroergocryptin, lisuride, pergolide, pramipexol, roxindol, topinirol, talipexol, tergurid and viozan, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

PAF-antagonists used here are preferably compounds selected from among lexipafant and 4-(2-chlorophenyl)-9-methyl-2-[3(4-morpholinyl)-3-propanon-1-yl]-6H-thieno-[3.2-f]-[1.2.4]triazolo[4.3-a][1.4]diazepines, 6-(2-chlorophenyl)-8.9-dihydro-1-methyl-8-[(4-morpholinyl)carbonyl]-4H.7H-cyclo-penta-[4.5]thieno-[3.2-f][1.2.4]triazolo[4.3-a][1.4]diazepines, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTB4-receptor antagonists used here are preferably compounds selected from among for example amebulant (=ethyl [[4-[[3-[[4-[1-(4-hydroxyphenyl)-1-methylethyl]phenoxy] methyl]phenyl]methoxy]phenyl]iminomethyl]-carbamate), optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

LTD4-receptor antagonists used here are preferably compounds selected from among montelukast, pranlukast, zafirlukast, and (E)-8-[2-[4-[4-(4-fluorophenyl)butoxy]phenyl]ethenyl]-2-(1H-tetrazol-5-yl)-4H-1-benzopyran-4-one (MEN-91507), 4-[6-acetyl-3-[3-(4-acetyl-3-hydroxy-2-propylphenylthio)propoxy]-2-propylphenoxy]butyric acid (MN-001), 1-(((R)-(3-(2-(6,7-difluoro-2-quinolinyl)ethenyl) phenyl)-3-(2-(2-hydroxy-2-propyl)phenyl)thio)methylcyclopropaneacetic acid, 1-(((1(R)-3(3-(2-(2,3-dichlorothieno [3.2-b]pyridin-5-yl)-(E)-ethenyl)phenyl)-3-(2-(1-hydroxy-1-methylethyl)phenyl)propyl)thio)methyl) cyclopropaneacetic acid, [2-[[2-(4-tert-butyl-2-thiazolyl)-5-benzofuranyl]oxymethyl]phenyl]acetic acid optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

By salts or derivatives which the LTD4-receptor antagonists are optionally capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

Histamine H1 receptor antagonists that may be used are preferably compounds selected from among epinastine, cetirizine, azelastine, fexofenadine, levocabastine, loratadine, mizolastine, ketotifen, emedastine, dimetinden, clemastine, bamipine, cexchlorpheniramine, pheniramine, doxylamine, chlorophenoxamine, dimenhydrinate, diphenhydramine, promethazine, ebastine, olopatadine, desloratidine and meclozine, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Histamine H4 receptor antagonists that may be used are preferably compounds such as e.g. (5-chloro-1H-indol-2-yl) (4-methyl-1-piperazinyl)-methanone (JNJ-7777120), optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Inhibitors of non-receptor tyrosine kinases that may be used such as for example LYN, LCK, SYK, ZAP-70, FYN, BTK or ITK are preferably compounds selected from among 2-[(2-aminoethyl)amino]-4-[(3-bromophenyl)amino]-5-pyrimidinecarboxamide; 2-[[7-(3,4-dimethoxyphenyl)imidazo[1,2-c]pyrimidin-5-yl]amino]-3-pyridinecarboxamide; 6-[[5-fluoro-2-[3,4,5-trimethoxyphenyl)amino]-4-pyrimidinyl]amino]-2,2-dimethyl-2H-pyrido[3.2-b]-1,4-oxazin-3 (4H)-one; N-[3-bromo-7-(4-methoxyphenyl)-1,6-naphthyridin-5-yl]-1,3-propanediamine, 7-(4-methoxyphenyl)-N-methyl-1,6-naphthyridin-5-amine; N-[7-(4-methoxyphenyl)-1,6-naphthyridin-5-yl]-1,3-propanediamine; N-[7-(2-thienyl)-1,6-naphthyridin-5-yl-1, 3-propanediamine; N-[7-[4-(dimethylamino)phenyl]-1,6-naphthyridin-5-yl]-1,2-ethanediamine; N-[7-(4-methoxyphenyl)-2-(trifluoromethyl)-1,6-naphthyridin-5-yl]-1,3-propanediamine; N-[7-(4-methoxyphenyl)-3-phenyl-1,6-naphthyridin-5-yl]-1,3-propanediamine; N-(7-phenyl-1,6-naphthyridin-5-yl)-1,3-propanediamine; N-[7-(3-fluorophenyl)-1,6-naphthyridin-5-yl]-1,3-propanediamine; N-[7-(3-chlorophenyl)-1,6-naphthyridin-5-yl]-1,3-propanediamine; N-[7-[3-(trifluoromethoxy) phenyl]-1,6-naphthyridin-5-yl]-1,3-propanediamine; N-[7-(4-fluorophenyl)-1,6-naphthyridin-5-yl]-1,3-propanediamine; N-[7-(4-fluorophenyl)-1,6-naphthyridin-5-yl]-1,3-propanediamine; N-[7-(4-chlorophenyl)-1,6-naphthyridin-5-yl]-1,3-propanediamine; N-[7-(4'-methyl[1, 1'-biphenyl]-4-yl)-1,6-naphthyridin-1,3-propanediamine; N-[7-[4-(dimethylamino)phenyl]-1,6-naphthyridin-5-yl]-1, 3-propanediamine; N-[7-[4-(diethylamino)phenyl]-1,6-naphthyridin-5-yl]-1,3-propanediamine; N-[7-[4-(4-morpholinyl)phenyl]-1,6-naphthyridin-5-yl]-1,3-propanediamine; N-[7-[4-[[2-(dimethylamino)ethyl] methylamino]phenyl]-1,6-naphthyridin-5-yl]-1,3-propanediamine; N-[7-(4-bromophenyl)-1,6-naphthyridin-5-yl]-1,3-propanediamine; N-[7-(4-methylphenyl)-1,6-naphthyridin-5-yl]-1,3-propanediamine; N-[7-[4-(methylthio)phenyl]-1,6-naphthyridin-5-yl]-1,3-propanediamine; N-[7-[4-(1-methylethyl)phenyl]-1,6-naphthyridin-5-yl]-1,3-propanediamine; 7-[4-(dimethylamino)phenyl]-N-methyl-1,6-naphthyridin-5-amine; 7-[4-(dimethylamino)phenyl]-N,N-dimethyl-1,6-naphthyridin-5-amine; N-[7-[4-(dimethylamino)phenyl]-1, 6-naphthyridin-5-yl]-1,4-butanediamine; N-[7-[4-(dimethylamino)phenyl]-1,6-naphthyridin-5-yl]-1,5-pentanediamine; 3-[[7-[4-(dimethylamino)phenyl]-1,6-naphthyridin-5-yl]oxy]-1-propanol; 4-[5-(4-aminobutoxy)-1,6-naphthyridin-7-yl]-N,N-dimethyl-benzenamine; 4-[[7-[4-(dimethylamino)phenyl]-1,6-naphthyridin-5-yl]amino]-1-butanol; N-[7-[4-(dimethylamino)phenyl]-1,6-naphthyridin-5-yl]-N-methyl-1,3-propanediamine; N-[7-[4-(dimethylamino)phenyl]-1,6-naphthyridin-5-yl]-N'-methyl-1,3-propanediamine; N-[7-[4-(dimethylamino)phenyl]-1,6-naphthyridin-5-yl]-N,N'-dimethyl-1,3-propanediamine; 1-amino-3-[[7-[4-(dimethylamino)phenyl]-1,6-naphthyridin-5-yl]amino]-2-propanol; N-[7-[4-(dimethylamino)phenyl]-1,6-naphthyridin-5-yl]-2,2-dimethyl-1,3-propanediamine; 7-[4-(dimethylamino)phenyl]-N-(3-pyridinylmethyl)-1,6-naphthyridin-5-amine; N-[(2-aminophenyl)methyl]-7-[4-(dimethylamino)phenyl]-1,6-naphthyridin-5-amine; N-[7-[6-(dimethylamino)[1,1'-biphenyl]-3-yl]-1,6-naphthyridin-5-yl]-1,3-propanediamine; N-[7-[3-chloro-4-(diethylamino)phenyl]-1,6-naphthyridin-5-yl]-1,3-propanediamine; N-[7-[4-(dimethylamino)-3-methoxyphenyl]-1,6-naphthyridin-5-yl]-1,3-propanediamine; N-[7-[4-(diethylamino)phenyl]-3-methyl-1,6-naphthyridin-5-yl]-1,3-propanediamine; N-[7-(3'-fluoro[1,1'-biphenyl]-3-yl)-1,6-naphthyridin-5-yl]-1,2-ethanediamine, N-[7-(4-methoxyphenyl)-1,6-naphthyridin-5-yl]-1,6-naphthyridine-1,3-propanediamine; N,N'-bis(3-aminopropyl)-7-(4-methoxyphenyl)-2,5-diamine; N-[7-(4-methoxyphenyl)-2-(phenylmethoxy)-1,6-naphthyridin-5-yl]-1,6-naphthyridine-1,3-propanediamine; N5-(3-aminopropyl)-7-(4-methoxyphenyl)-N2-(phenylmethyl)-2,5-diamine;

N-[7-(2-naphthalenyl)-1,6-naphthyridin-5-yl]-1,3-propanediamine; N-[7-(2'-fluoro[1,1'-biphenyl]-4-yl)-1,6-naphthyridin-5-yl]-1,3-propanediamine; N-[7-(3,4,5-trimethoxyphenyl)-1,6-naphthyridin-5-yl]-1,3-propanediamine; N-[7-(3,4-dimethylphenyl)-1,6-naphthyridin-5-yl]-1,3-propanediamine; 1-amino-3-[[7-(2-naphthalenyl)-1,6-naphthyridin-5-yl]amino]-2-propanol; 1-amino-3-[[7-(2'-fluoro[1,1'-biphenyl]-4-yl)-1,6-naphthyridin-5-yl]amino]-2-propanol; 1-amino-3-[[7-(4'-methoxy[1,1'-biphenyl]-4-yl)-1,6-naphthyridin-5-yl]amino]-2-propanol; 1-amino-3-[[7-(3,4,5-trimethoxyphenyl)-1,6-naphthyridin-5-yl]amino]-2-propanol; 1-amino-3-[[7-(4-bromophenyl)-1,6-naphthyridin-5-yl]amino]-2-propanol; N-[7-(4'-methoxy[1,1'-biphenyl]-4-yl)-1,6-naphthyridin-5-yl]-2,2-dimethyl-1,3-propanediamine; 1-[[7-[4-(dimethylamino)phenyl]-1,6-naphthyridin-5-yl]amino]-2-propanol; 2-[[2-[[7-[4-(dimethylamino)phenyl]-1,6-naphthyridin-5-yl]amino]ethyl]thio]-ethanol;

7-[4-(dimethylamino)phenyl]-N-(3-methyl-5-isoxazolyl)-1,6-naphthyridin-5-amine; 7-[4-(dimethylamino)phenyl]-N-4-pyrimidinyl-1,6-naphthyridin-5-amine; N-[7-[4-(dimethylamino)phenyl]-1,6-naphthyridin-5-yl]-1,3-cyclohexanediamine; N,N-dimethyl-4-[5-(1-piperazinyl)-1,6-naphthyridin-7-yl]-benzenamine; 4-[5-(2-methoxyethoxy)-1,6-naphthyridin-7-yl]-N,N-dimethyl-benzenamin; 1-[7-[4-(dimethylamino)phenyl]-1,6-naphthyridin-5-yl]-4-piperidinol; 1-[7-[4-(dimethylamino)phenyl]-1,6-naphthyridin-5-yl]-3-pyrrolidinol; 7-[4-(dimethylamino)phenyl]-N-(2-furanylmethyl)-1,6-naphthyridin-5-amine; 7-[4-(dimethylamino)phenyl]-N-[3-(1H-imidazol-1-yl)propyl]-1,6-naphthyridin-5-amine; 1-[7-[4-(dimethylamino)phenyl]-1,6-naphthyridin-5-yl]-4-piperidinecarboxamide; 1-[3-[[7-[4-(dimethylamino)phenyl]-1,6-naphthyridin-5-yl]amino]propyl]-2-pyrrolidinone; N-[3'-[5-[(3-aminopropyl)amino]-1,6-naphthyridin-7-yl][1,1'-biphenyl]-3-yl]-acetamide; N-[7-(4'-fluoro[1,1'-biphenyl]-4-yl)-1,6-naphthyridin-5-yl]-1,3-propanediamine; N-[4'-[5-[(3-aminopropyl)amino]-1,6-naphthyridin-7-yl][1,1'-biphenyl]-3-yl]-acetamid; N-[7-[4-(1,3-benzodioxol-5-yl)phenyl]-1,6-naphthyridin-5-yl]-1,3-propanediamine; N-[7-[4-(2-thienyl)phenyl]-1,6-naphthyridin-5-yl]-1,3-propanediamine; N-[7-[4-fluoro-3-(trifluoromethyl)phenyl]-1,6-naphthyridin-5-yl]-1,3-propanediamine; N-[7-[4-(3-pyridinyl)phenyl]-1,6-naphthyridin-5-yl]-1,3-propanediamine;

N-[7-(1,3-benzodioxol-5-yl)-1,6-naphthyridin-5-yl]-1,3-propanediamine; N-[7-(6-methoxy-2-naphthalenyl)-1,6-naphthyridin-5-yl]-1,3-propanediamine; 7-[4-(dimethylamino)phenyl]-N-(4-pyridinylmethyl)-1,6-naphthyridin-5-amine; 3-[[7-[4-(dimethylamino)phenyl]-1,6-naphthyridin-5-yl]methylamino]-propanenitril; 7-[4-(dimethylamino)phenyl]-N-[1-(phenylmethyl)-4-piperidinyl]-1,6-naphthyridin-5-amine; N-[7-[4-(dimethylamino)phenyl]-1,6-naphthyridin-5-yl]-1,2-cyclohexanediamin, N-[7-[4-(dimethylamino)phenyl]-1,6-naphthyridin-5-yl]-1,2-cyclohexanediamine, (1R,2S)-rel-., N-[7-[4-(dimethylamino)phenyl]-1,6-naphthyridin-5-yl]-1,2-benzenedimethanamine; N-[7-[4-(diethylamino)phenyl]-1,6-naphthyridin-5-yl]-1,4-butanediamine; N-[7-[3',5'-bis(trifluoromethyl)[1,1'-biphenyl]-4-yl]-1,6-naphthyridin-5-yl].3-propanediamine; N-[7-(3'-methoxy[1,1'-biphenyl]-4-yl)-1,6-naphthyridin-5-yl]-1,3-propanediamine; N-[7-(3'-fluoro[1,1'-biphenyl]-4-yl)-1,6-naphthyridin-5-yl]-1,3-propanediamine; 4-[[7-[4-(dimethylamino)phenyl]-1,6-naphthyridin-5-yl]oxy]-1-butanol; N-[7-[4-(dimethylamino)phenyl]-1,6-naphthyridin-5-yl]-1,4-cyclohexanediamine; 7-[4-(dimethylamino)phenyl]-N-(2.2.6.6-tetramethyl-4-piperidinyl)-1,6-naphthyridin-5-amine; N-[7-[3-bromo-4-(dimethylamino)phenyl]-1,6-naphthyridin-5-yl]-1,3-propanediamine; N-[7-(1-methyl-1H-indol-5-yl)-1,6-naphthyridin-5-yl]-1,3-propanediamine; N-[7-[3-(trifluoromethyl)phenyl]-1,6-naphthyridin-5-yl]-1,3-propanediamine; N-[7-[4-(trifluoromethyl)phenyl]-1,6-naphthyridin-5-yl]-1,3-propanediamine; N-[7-(3-bromo-4-methoxyphenyl)-1,6-naphthyridin-5-yl]-1,3-propanediamine; N-[7-[4-[[3-(dimethylamino)propyl]methylamino]phenyl]-1,6-naphthyridin-5-yl]-1,4-cyclohexanediamine; N-[7-[4-[[2-(dimethylamino)ethyl]methylamino]phenyl]-1,6-naphthyridin-5-yl]-1,4-cyclohexanediamine; N-[7-[4-(dimethylamino)-3-methoxyphenyl]-1,6-naphthyridin-5-yl]-1,4-cyclohexanediamine; N-[7-[4-(4-morpholinyl)phenyl]-1,6-naphthyridin-5-yl]-1,4-cyclohexanediamine; N-[7-[3-bromo-4-(4-morpholinyl)phenyl]-1,6-naphthyridin-5-yl]-1,4-cyclohexanediamine; 4-[[7-[4-[[2-(dimethylamino)ethyl]methylamino]phenyl]-1,6-naphthyridin-5-yl]oxy]-cyclohexanol; N-[7-[3-bromo-4-(4-morpholinyl)phenyl]-1,6-naphthyridin-5-yl]-1,3-propanediamine; N,N-dimethyl-4-[5-(4-methyl-1-piperazinyl)-1,6-naphthyridin-7-yl]-benzenamine; 4-[[7-[4-[[3-(dimethylamino)propyl]methylamino]phenyl]-1,6-naphthyridin-5-yl]oxy]-cyclohexanol; N-[7-[4-[[2-(dimethylamino)ethyl]methylamino]phenyl]-1,6-naphthyridin-5-yl]-1,4-butanediamine; 1,1-dimethylethyl[3-[[5-[(3-aminopropyl)amino]-7-(4-methoxyphenyl)-1,6-naphthyridin-2-yl]amino]propyl]-carbamate, optionally in the form of the racemates, enantiomers, diastereomers thereof and optionally in the form of the pharmacologically acceptable acid addition salts, solvates or hydrates thereof. According to the invention the preferred acid addition salts are selected from among hydrochloride, hydrobromide, hydriodide, hydrosulphate, hydrophosphate, hydromethanesulphonate, hydronitrate, to hydromaleate, hydroacetate, hydrocitrate, hydrofumarate, hydrotartrate, hydroxalate, hydrosuccinate, hydrobenzoate and hydro-p-toluenesulphonate.

MAP Kinase inhibitors used are preferably compounds selected from among:

bentamapimod (AS-602801), doramapimod (BIRB-796), 5-carbamoylindole (SD-169), 6-[(aminocarbonyl)(2,6-difluorophenyl)amino]-2-(2,4-difluorophenyl)-3-pyridinecarboxamide (VX-702), alpha-[2-[[2-(3-pyridinyl)ethyl]amino]-4-pyrimidinyl]-2-benzothiazoleacetonitrile (AS-601245), 9,12-epoxy-1H-diindolo[1,2,3-fg:3',2',1'-kl]pyrrolo[3,4-i][1.6]benzodiazocine-10-carboxylic acid (CEP-1347) and 4-[3-(4-chlorophenyl)-5-(1-methyl-4-piperidinyl)-1H-pyrazole-4-yl]-pyrimidine (SC-409), optionally in the form of the racemates, enantiomers, diastereomers thereof and optionally in the form of the pharmacologically acceptable acid addition salts, solvates or hydrates thereof.

iNOS-inhibitors used are preferably compounds selected from among: S-(2-aminoethyl)isothiourea, aminoguanidine, 2-aminomethylpyridine, 5,6-dihydro-6-methyl-4H-1,3-thiazin-2-amine (AMT), L-canavanine, 2-iminopiperidine, S-isopropylisothiourea, S-methylisothiourea, S-ethylisothiourea, S-methyltiocitrulline, S-ethylthiocitrulline, L-NA ($N^\omega$-nitro-L-arginine), L-NAME ($N^\omega$-nitro-L-argininemethylester), L-NMMA ($N^\omega$-monomethyl-L-arginine), L-NIO ($N^\omega$-iminoethyl-L-ornithine), L-NIL ($N^\omega$-iminoethyl-lysine), (S)-6-acetimidoylamino-2-amino-hexanoic acid (1H-tetrazol-5-yl)-amide (SC-51), N-[[3-(aminomethyl)phenyl]methyl]-ethanimidamide (1400 W), (S)-4-(2-acetimidoylamino-ethylsulphanyl)-2-amino-butyric acid (GW274150), 2-[2-(4-methoxy-pyridin-2-yl)-ethyl]-3H-imidazo[4,5-b]pyridine (BYK191023), 2-((R)-3-amino-1-phenyl-propoxy)-4-chloro-5-fluorobenzonitrile, 2-((1R,3S)-3-amino-4-hydroxy-1-thiazol-5-yl-butylsulphanyl)-6-trifluoromethyl-nicotinonitrile, 2-((1R,3S)-3-amino-4-hydroxy-1-thiazol-5-yl-butylsulphanyl)-4-chloro-benzonitrile, 2-((1R,3S)-3-amino-4-hydroxy-1-thiazol-5-yl-butylsulphanyl)-5-chloro-benzonitrile, (2S,4R)-2-amino-4-(2-chloro-5-trifluoromethyl-phenylsulphanyl)-4-thiazol-5-yl-butan-1-ol, 2-((1R,3S)-3-amino-4-hydroxy-1-thiazol-5-yl-butylsulphanyl)-5-chloro-nicotinonitrile, 4-((S)-3-amino-4-hydroxy-1-phenyl-butylsulphanyl)-6-methoxy-nicotinonitrile, substituted 3-phenyl-3,4-dihydro-1l-isoquinolinamine such as e.g. (1S,5S,6R)-7-chloro-5-methyl-2-aza-bicyclo[4.1.0]hept-2-en-3-ylamine (ONO-1714), (4R,5R)-5-ethyl-4-methyl-thiazolidin-2-ylideneamine, (4R,5R)-5-ethyl-4-methyl-selenazolidin-2-ylideneamine, 4-aminotetrahydrobiopterine, (E)-3-(4-chloro-phenyl)-N-(1-{2-oxo-2-[4-(6-trifluoromethyl-pyrimidin-4-yloxy)-piperidin-1-yl]-ethylcarbamoyl}-2-pyridin-2-yl-ethyl)-acrylamide (FR260330), 3-(2,4-difluoro-phenyl)-6-[2-(4-imidazol-1-ylmethyl-phenoxy)-ethoxy]-2-phenyl-pyridine (PPA250), methyl 3-{[(benzo[1,3]dioxol-5-ylmethyl)-carbamoyl]-methyl}-4-(2-imidazol-1-yl-pyrimidin-4-yl)-piperazine-1-carboxylate (BBS-1), (R)-1-(2-imidazol-1-yl-6-methyl-pyrimidin-4-yl)-pyrrolidin-2-carboxylate (2-benzo[1,3]dioxol-5-yl-ethyl)-amide (BBS-2) and the pharmaceutical salts, prodrugs or solvates thereof.

As iNOS-inhibitors within the scope of the present invention it is also possible to use antisense oligonucleotides, particularly those antisense oligonucleotides that bind iNOS-coding nucleic acids. For example, WO 01/52902 describes antisense oligonucleotides, particularly antisense oligonucleotides that bind iNOS coding nucleic acids, for modulating the expression of iNOS.

MRP4-inhibitors used are preferably compounds selected from among N-acetyl-dinitrophenyl-cysteine, cGMP, cholates, diclofenac, dehydroepiandrosterone 3-glucuronide, dehydroepiandrosterone 3-sulphate, dilazep, dinitrophenyl-s-glutathione, estradiol 17-glucuronide, estradiol 3,17-disulphate, estradiol 3-glucuronide, estradiol 3-sulphate, estrone 3-sulphate, flurbiprofen, folate, n5-formyl-tetrahydrofolate, glycocholate, glycolithocholic acid sulphate, ibuprofen, indomethacin, indoprofen, ketoprofen, lithocholic acid sulphate sulphate, methotrexate, ((E)-3-[[[3-[2-(7-chloro-2-quinolinyl)ethenyl]phenyl]-[[3-dimethylamino)-3-oxopropyl]thio]methyl]thio]-propanoic acid), alpha-naphthyl-beta-D-glucuronide, nitrobenzyl mercaptopurine riboside, probenecid, sildenafil, sulphinepyrazone, taurochenodeoxycholate, taurocholate, taurodeoxycholate, taurolithocholate, topotecan, trequinsin, zaprinast and dipyridamole, optionally in the form of the racemates, enantiomers and diastereomers thereof and the pharmacologically acceptable acid addition salts and hydrates thereof.

The leukotriene biosynthesis inhibitors used such as for example those selected from among the 5-lipoxygenase (5-LO) inhibitors, cPLA2 inhibitors, leukotriene A4 hydrolase inhibitors or FLAP inhibitors, are preferably compounds selected from among zileuton, tipelukast, licofelone, darapladib, optionally in the form of the racemates, enantiomers and diastereomers thereof and the pharmacologically acceptable acid addition salts and hydrates thereof.

Non-steroidal anti-inflammatories (NSAIDs) that may be used are preferably compounds selected from among piroxicam, diclofenac, naproxen, flurbiprofen, fenoprofen, ketoprofen, ibuprofen, nimesulide, indomethacin, sulindac, azapropazone, phenylbutazone, aspirin; meloxicam, celecoxib, rofecoxib, valdecoxib, lumarocoxib, parecoxib, tenoxicam and etoricoxib, optionally in the form of the racemates, enantiomers and diastereomers thereof and optionally in the form of the pharmacologically acceptable acid addition salts, prodrugs, solvates or hydrates thereof.

CRTH2 antagonists used are preferably compounds selected from among ramatroban and laropiprant, optionally in the form of the racemates, enantiomers and diastereomers thereof and optionally in the form of the pharmacologically acceptable acid addition salts, prodrugs, solvates or hydrates thereof.

DP1-receptor modulators used are preferably compounds selected from among 7-[(1R,2R,3S,5S)-2-[[(5-hydroxy-benzo[b]thien-3-yl)carbonyl]amino]-6,6-dimethylbicyclo[3.1.1]hept-3-yl], (5Z)-5-heptenoic acid (S-5751), laropiprant, and 2-[[4-[(1R,2S,3R,5R)-5-chloro-2-[(3S)-3-cyclohexyl-3-hydroxy-1-propyn-1-yl]-3-hydroxycyclopentyl]butyl]thio]-acetic acid (TS-002), optionally in the form of the racemates, enantiomers and diastereomers thereof and optionally in the form of the pharmacologically acceptable acid addition salts, prodrugs, solvates or hydrates thereof.

Thromboxane receptor antagonists used here are preferably compounds to selected from among seratrodast, N-[[(1,1-dimethylethyl)amino]carbonyl]-2-[(4-methylphenyl)amino]-5-nitro-benzenesulphonamide (BM-573), (+/−)-sodium[2-(4-chlorophenylsulphonylaminomethyl)-indan-5-yl]acetate monohydrate (Z-335) and 2-[[[4-[[(4-chlorophenyl)sulphonyl]amino]butyl][[3-[[4-(1-methylethyl)-2-thiazolyl]methoxy]phenyl]methyl]amino]sulphonyl]-benzoic acid (KP-496), optionally in the form of the racemates, enantiomers and diastereomers thereof and optionally in the form of the pharmacologically acceptable acid addition salts, prodrugs, solvates or hydrates thereof.

Chemokine receptor antagonists that may be used are preferably compounds selected from among N-[5-chloro-2-[2-[(2R)-4-[(4-fluorophenyl)methyl]-2-methyl-1-piperazinyl]-2-oxoethoxy]phenyl]-urea hydrochloride (1:1) (BX-471), 2, N-[(1S,2S,4R)-4-(aminocarbonyl)-1-[(3-fluorophenyl)methyl]-2,7-dihydroxy-7-methyloctyl]-quinoxalinecarboxamide (CP-481715), (4,6-dimethyl-5-pyrimidinyl)[4-[(3S)-4-[(1R)-2-methoxy-1-[4-(trifluoromethyl)phenyl]ethyl]-3-methyl-1-piperazinyl]-4-methyl-1-piperidinyl]-methanone (Sch-417690), 2-hydroxy-N,N-dimethyl-3-[[2-[[(1R)-1-(5-methyl-2-furanyl)propyl]amino]-3,4-dioxo-1-cyclobuten-1-yl]amino]-benzamide (SCH-527123) and 1,4,8,11-tetraaza-cyclotetradecane, 1,1'-[1,4-phenylenebis(methylene)]bis, hydrochloride (1:8) (AMD-3100), optionally in the form of the racemates, enantiomers and diastereomers thereof and optionally in the form of the pharmacologically acceptable acid addition salts, prodrugs, solvates or hydrates thereof.

Neurokinin (NK1 or NK2) antagonists that may be used are preferably compounds selected from among: saredutant, nepadutant and figopitant, optionally in the form of the racemates, enantiomers and diastereomers thereof and optionally in the form of the pharmacologically acceptable acid addition salts, prodrugs, solvates or hydrates thereof.

Sphingosine1-phosphate receptor modulators that may be used are preferably compounds such as e.g. sonepcizumab, optionally in the form of the racemates, enantiomers and diastereomers thereof and optionally in the form of the pharmacologically acceptable acid addition salts, prodrugs, solvates or hydrates thereof.

Mucoregulators that may be used are preferably compounds selected from among:

3-[2-oxo-2-[2-[[3-(trifluoromethyl)phenyl]amino]-3-pyridinyl]ethyl]-1(3H)-isobenzofuranone (MSI-2216), erdosteine, fluorovent, talniflumate, fudosteine, optionally in the form of the racemates, enantiomers and diastereomers thereof and optionally in the form of the pharmacologically acceptable acid addition salts, prodrugs, solvates or hydrates thereof.

PPAR gamma agonists that may be used are preferably compounds selected from among: rosiglitazone, ciglitazone, pioglitazone and N-[2-[2-[(3-fluorophenyl)imino]-4-[4-(4-morpholinyl)phenyl]-3(2H)-thiazolyl]ethyl]-N'-methyl-urea (SMP-028), optionally in the form of the racemates, enantiomers and diastereomers thereof and optionally in the form of the pharmacologically acceptable acid addition salts, prodrugs, solvates or hydrates thereof.

Rho kinase inhibitors that may be used are preferably compounds such as e.g. Fasudil, optionally in the form of the racemates, enantiomers and diastereomers thereof and optionally in the form of the pharmacologically acceptable acid addition salts, prodrugs, solvates or hydrates thereof.

Adenosine receptor modulators that may be used are preferably compounds selected from among 4-(3,4-dichlorophenyl)-5-(4-pyridinyl)-2-thiazolamine (CGH-2466), 3-ethyl-3,9-dihydro-1-propyl-8-[1-[[3-(trifluoromethyl)phenyl]methyl]-1H-pyrazol-4-yl]-1H-purine-2,6-dione (CVT-6883), N-(4-cyanophenyl)-2-[4-(2.3.6.9-tetrahydro-2,6-dioxo-1,3-dipropyl-1H-purin-8-yl)phenoxy]-acetamide (MRS-1754), optionally in the form of the racemates, enantiomers and diastereomers thereof and optionally in the form of the pharmacologically acceptable acid addition salts, prodrugs, solvates or hydrates thereof.

Bradykinin (BK2 or BK1) antagonists that may be used are preferably compounds selected from among icatibant and 1-piperazinepentanaminium, delta-amino-4-[[4-[[[2,4-dichloro-3-[[(2,4-dimethyl-8-quinolinyl)oxy]methyl]phenyl]sulphonyl]amino]tetrahydro-2H-pyran-4-yl]carbonyl]-N,N,N-trimethyl-ε-oxo, chloride, hydrochloride (1:1:1), (deltaS)-(MEN-16132), optionally in the form of the racemates, enantiomers and diastereomers thereof and optionally in the form of the pharmacologically acceptable acid addition salts, prodrugs, solvates or hydrates thereof.

Endothelin antagonists that may be used are preferably compounds selected from among actelion-1, ambrisentan, sitaxsentan, N-(2-acetyl-4.6-dimethylphenyl)-3-[[(4-chloro-3-methyl-5-isoxazolyl)amino]sulphonyl]-2-thiophenecarboxamide (TBC-3214) and bosentan, optionally in the form of the racemates, enantiomers and diastereomers thereof and optionally in the form of the pharmacologically acceptable acid addition salts, prodrugs, solvates or hydrates thereof.

Interleukin 1-beta converting enzyme (ICE) inhibitors that may be used are preferably compounds selected from among pralnacasan and N-(4-amino-3-chlorobenzoyl)-3-methyl-L-valyl-N-[(2R,3S)-2-ethoxytetrahydro-5-oxo-3-furanyl]-L-prolinamide (=VX-765), optionally in the form of the racemates, enantiomers and diastereomers thereof and optionally in the form of the pharmacologically acceptable acid addition salts, prodrugs, solvates or hydrates thereof.

Toll-like receptor (TLR) modulators that may be used are preferably compounds selected from among resiquimod, heplisav, resatorvid (TAK-242), optionally in the form of the racemates, enantiomers and diastereomers thereof and optionally in the form of the pharmacologically acceptable acid addition salts, prodrugs, solvates or hydrates thereof.

HMG-CoA Reductase inhibitors that may be used are preferably compounds selected from among lovastatin, simvastatin, pravastatin, fluvastatin and avorvastatin, optionally in the form of the racemates, enantiomers and diastereomers thereof and optionally in the form of the pharmacologically acceptable acid addition salts, prodrugs, solvates or hydrates thereof.

VLA-4 antagonists that may be used are preferably compounds selected from among natalizumab, valategrast, optionally in the form of the racemates, enantiomers and diastereomers thereof and optionally in the form of the pharmacologically acceptable acid addition salts, prodrugs, solvates or hydrates thereof.

SHIP agonists that may be used are preferably compounds selected from among 2,3,4,4a,5,6,6a,11,11a,11b-decahydro-4,4,6a,7,11b-pentamethyl, (4aS,6aR,11aR,11bS)-1H-benzo[a]fluoren-9-ol (AQX-MN100) and MN-106, optionally in the form of the racemates, enantiomers and diastereomers thereof and optionally in the form of the pharmacologically acceptable acid addition salts, prodrugs, solvates or hydrates thereof.

Anti-TNF-antibodies which may be used here are preferably compounds selected from among infliximab, adalimumab, golimumab, cytoFab and etanercept.

Substances to counter swelling of the airways that may be used are preferably compounds selected from among phenylephrine, phenylpropanolamine, pseudophedrine, oxymetazoline, epinephrine, naphazoline, xylometazoline, propylhexedrine and Ilevo-desoxyephedrine, optionally in the form of the racemates, enantiomers and diastereomers thereof and optionally in the form of the pharmacologically acceptable acid addition salts, prodrugs, solvates or hydrates thereof.

Antitussive substances that may be used are preferably compounds selected from among hydrocodone, caramiphen, carbetapentane and dextramethorphan, optionally in the form of the racemates, enantiomers and diastereomers thereof and optionally in the form of the pharmacologically acceptable acid addition salts, prodrugs, solvates or hydrates thereof.

Preferred lipoxin A4 derivatives which may be used here are preferably compounds selected from among 7,9,11,13-eicosatetraenoic acid, 5,6,15-trihydroxy, (5S,6R,7E,9E,11Z,13E,15R)-(15-epi-lipoxin a4), 7,9,11,13-eicosatetraenoic acid, 16-(4-fluorophenoxy)-5,6,15-trihydroxy, (5S,6R,7E,9E,11Z,13E,15S)-(ATL-1), aspirin-triggered lipoxin A(4) and analogues, protectin D1 (4,7,11,13,15,19-docosahexaenoic acid, 10,17-dihydroxy, (4Z,7Z,10R,11E,13E,15Z,17S,19Z)-, resolvin E1 (6,8,10,14,16-eicosapentaenoic acid, 5,12,18-trihydroxy, (5S,6Z,8E,10E,12R,14Z,16E,18R)—) and benzo-lipoxin A4 analogues, optionally in the form of the racemates, enantiomers and diastereomers thereof and optionally in the form of the pharmacologically acceptable acid addition salts, prodrugs, solvates or hydrates thereof.

Preferred FPRL1-modulators which may be used here are preferably compounds such as e.g. methyl 5(S),6(R),7-trihydroxyheptanoate, optionally in the form of the racemates, enantiomers and diastereomers thereof and optionally in the form of the pharmacologically acceptable acid addition salts, prodrugs, solvates or hydrates thereof.

Preferred PI3 kinase antagonists which may be used here are preferably compounds selected from among 5-(quinoxalin-6-ylmethylene)thiazolidine-2,4-dione (AS-605240), 2-[(6-amino-9H-purin-9-yl)methyl]-5-methyl-3-(2-methylphenyl)-4(3H)-quinazolinone (C-87114), and 2-methyl-2-[4-[3-methyl-2-oxo-8-(quinoline-3-yl)-2,3-dihydroimidazo[4,5-c]quinolin-1-yl]phenyl]propionitrile (BEZ-235), optionally in the form of the racemates, enantiomers and diastereomers thereof and optionally in the form of the pharmacologically acceptable acid addition salts, prodrugs, solvates or hydrates thereof.

Preferred CCR5 antagonists which may be used here are preferably compounds selected from among maraviroc (4,4-difluoro-N-[(1S)-3-[(3-exo)-3-[3-methyl-5-(1-methylethyl)-4H-1,2,4-triazol-4-yl]-8-azabicyclo[3.2.1]oct-8-yl]-1-phenylpropyl]-cyclohexanecarboxamide), CCR5 mAb004, vicriviroc ((4.6-dimethyl-5-pyrimidinyl)[4-[(3S)-4-[(1R)-2-methoxy-1-[4-(trifluoromethyl)phenyl]ethyl]-3-methyl-1-piperazinyl]-4-methyl-1-piperidinyl]-methanone) and nifeviroc (N-[1-[[(3S,4R)-1-(cyclopentylcarbonyl)-4-hydroxy-4-phenyl-3-pyrrolidinyl]methyl]-4-piperidinyl]-N-2-propen-1-yl-(4-nitrophenyl)methyl ester-carbaminic acid), is optionally in the form of the racemates, enantiomers and diastereomers thereof and optionally in the form of the pharmacologically acceptable acid addition salts, prodrugs, solvates or hydrates thereof.

Preferred CXCR1 or CXCR2 antagonists which may be used here are preferably compounds such as e.g. 3-[[3-[(dimethylamino)carbonyl]-2-hydroxyphenyl]amino]-4-[[(R)-1-(5-methylfuran-2-yl)propyl]amino]cyclobut-3-ene-1,2-dione (SCH-527123), optionally in the form of the racemates, enantiomers and diastereomers thereof and optionally in the form of the pharmacologically acceptable acid addition salts, prodrugs, solvates or hydrates thereof.

Preferred substances, according to the invention, are the acid addition salts of the above mentioned MAP kinase inhibitors, iNOS inhibitors, MRP4 inhibitors, leukotriene biosynthese inhibitors, non-steroidal anti-inflammatory agents (NSAIDs), CRTH2 antagonists, DP1-receptor modulators, thromboxane receptor antagonists, chemokine receptor antagonists, neurokinin (NK1 or NK2) antagonists, sphingosine1-phosphate receptor modulators, mucoregulators, PPAR gamma agonists, Rho kinase inhibitors, adenosine receptor modulators, bradykinin receptor antagonists, endothelin antagonists, interleukin 1-beta converting enzyme (ICE) inhibitors, toll-like receptor (TLR) modulators, HMG-CoA reductase inhibitors, VLA-4 antagonists, SHIP agonists, anti-TNF-antibodies, substances to combat swelling of the airways, antitussive substances, lipoxin A4 derivatives, PI3 kinase antagonists, FPRL1-modulators, CCR5 antagonists, CXCR1 or CXCR2-antagonists also selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous, subcutaneous or intramuscular administration. For inhalation, according to the invention, solutions containing 0.01 to 1.0, preferably 0.1 to 0.5% active substance are suitable. For administration by inhalation the use of powders, ethanolic or aqueous solutions is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers. Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

For pharmaceutical use the compounds according to the invention are generally used for warm-blooded vertebrates, particularly humans, in doses of 0.01-100 mg/kg of body weight, preferably 0.1-15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carb-oxymethylcellulose or fatty substances such as hard fat or suitable mixtures thereof to produce conventional galenic preparations such as plain or coated tablets, capsules, powders, suspensions, solutions, sprays or suppositories.

The Examples which follow illustrate the present invention without restricting its scope:

Examples of Pharmaceutical Formulations

A) Coated Tablets Containing 75 mg of Active Substance
Composition:

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinyl-pyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

B) Tablets Containing 100 mg of Active Substance
Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

C) Tablets Containing 150 mg of Active Substance
Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate.

Tablets are pressed from the mixture.

Weight of tablet: 300 mg die: 10 mm, flat

D) Hard Gelatine Capsules Containing 150 mg of Active Substance
Composition:

| 1 capsule contains: | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

E) Suppositories Containing 150 mg of Active Substance
Composition:

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

F) Suspension Containing 50 mg of Active Substance
Composition:

| 100 ml of suspension contain: | | |
|---|---|---|
| active substance | | 1.00 g |
| carboxymethylcellulose-Na-salt | | 0.10 g |
| methyl p-hydroxybenzoate | | 0.05 g |
| propyl p-hydroxybenzoate | | 0.01 g |
| glucose | | 10.00 g |
| glycerol | | 5.00 g |
| 70% sorbitol solution | | 20.00 g |
| flavouring | | 0.30 g |
| dist. water | ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

G) Ampoules Containing 10 mg Active Substance
Composition:

| active substance | | 10.0 mg |
|---|---|---|
| 0.01N hydrochloric acid q.s. | | |
| double-distilled water | ad | 2.0 ml |

Preparation:

The active substance is dissolved in the necessary amount of 0.01 N HCl, made isotonic with common salt, filtered sterile and transferred into 2 ml ampoules.

H) Ampoules Containing 50 mg of Active Substance
Composition:

| active substance | | 50.0 mg |
|---|---|---|
| 0.01N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

I) Capsules for Powder Inhalation Containing 5 mg of Active Substance

| 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg).

weight of capsule: 70.0 mg
size of capsule=3

J) Solution for Inhalation for Hand-Held Nebulisers Containing 2.5 mg Active Substance

| 1 spray contains: | |
|---|---|
| active substance | 2.500 mg |
| benzalkonium chloride | 0.001 mg |
| 1N hydrochloric acid q.s. | |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

The invention claimed is:

1. A method for the treatment of a disease of the airways accompanied by increased production of mucus, wherein the disease is selected from chronic bronchitis, chronic obstructive bronchitis (COPD), asthma, bronchiectasis, allergic or non-allergic rhinitis or sinusitis, cystic fibrosis, α1-antitrypsin deficiency, coughs, pulmonary emphysema, pulmonary fibrosis and hyperreactive airways, comprising administering to a patient a therapeutically effective amount of a compound of formula (I)

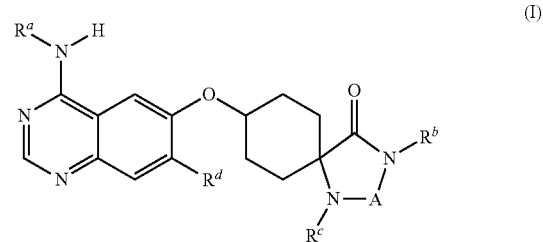

wherein
$R^a$ denotes a phenyl or 1-phenylethyl group, wherein the phenyl nucleus is substituted in each case by the groups $R^1$ to $R^3$, wherein
$R^1$ and $R^2$ which may be identical or different, denote hydrogen or
a group selected from among
F, Cl, Br, I, $OCH_2F$, $OCHF_2$, $OCF_3$, $CH_2F$, $CHF_2$, $CF_3$, CN, $NO_2$, $NH_2$ and OH,
or
a group selected from among
$C_{1-4}$-alkyl, $C_{1-4}$-alkyl-O, $C_{2-3}$-alkenyl, $C_{2-3}$-alkynyl,
phenyl, phenyl-O, phenyl-$C_{1-3}$-alkyl, phenyl-$C_{1-3}$-alkyl-O, heteroaryl, heteroaryl-O, heteroaryl-$C_{1-3}$-alkyl, heteroaryl-$C_{1-3}$-alkyl-O, while the above-mentioned phenyl groups are mono- or disubstituted by groups $R^5$,
and
$R^3$ denotes hydrogen,
or
a group selected from among
F, Cl, Br and $CH_3$,
$R^b$ denotes hydrogen, or a group, optionally substituted, selected from among $C_{1-6}$-alkyl, $C_{3-6}$-cycloalkyl- and $C_{3-6}$-cycloalkyl-$C_{1-3}$-alkyl,
$R^c$ denotes hydrogen, or an optionally substituted group selected from among $C_{1-6}$-alkyl, $C_{3-6}$-cycloalkyl, $C_{3-6}$-cycloalkyl-$C_{1-3}$-alkyl, $C_{1-6}$-alkyl-CO, $C_{3-6}$-cycloalkyl- CO, $C_{3-6}$-cycloalkyl-$C_{1-3}$-alkyl-CO, $C_{1-6}$-alkyl-$SO_2$, $C_{3-6}$-cycloalkyl-$SO_2$, $C_{3-6}$-cycloalkyl-$C_{1-3}$-alkyl-$SO_2$, phenyl-CO— and phenyl-$SO_2$, $R^d$ denotes hydrogen or a group selected from among F, Cl, Br, I, OH, $C_{1-4}$-alkyl, $C_{1-4}$-alkyl-O, $C_{1-2}$-alkyl-O substituted by 1 to 3 fluorine atoms, $C_{3-7}$-cycloalkyl-O, $C_{3-7}$-cycloalkyl-$C_{1-4}$-alkyl-O, tetrahydrofuran-3-yl-O, tetrahydropyran-3-yl-O, tetrahydro-pyran-4-yl-O, tetrahydrofuranyl-$C_{1-4}$-alkyl-O— and tetrahydropyranyl-$C_{1-4}$-alkyl-O, or $R^4$—$C_{1-4}$-alkyl, while the linking of the groups $R^4$ may take place via each C atom of the alkyl group, or $R^4$—$C_{2-4}$-alkyl-O, wherein the group $R^4$ is separated from the oxygen atom by at least 2 C atoms, or a group selected from among pyrrolidin-2-yl-$C_{1-4}$-alkyl-O, pyrrolidin-3-yl-$C_{1-4}$-alkyl-O, piperidin-2-yl-$C_{1-4}$-alkyl-O, piperidin-3-yl-$C_{1-4}$-alkyl-O, piperidin-4-yl-$C_{1-4}$-alkyl-O, azepan-2-yl-$C_{1-4}$-alkyl-O, azepan-3-yl-$C_{1-4}$-alkyl-O, azepan-4-yl-$C_{1-4}$-alkyl-O, morpholin-2-yl-$C_{1-4}$-alkyl-O, morpholin-3-yl-$C_{1-4}$-alkyl-O, 1-($C_{1-3}$-alkyl)-pyrrolidin-2-yl-$C_{1-4}$-alkyl-O, 1-($C_{1-3}$-alkyl)-pyrrolidin-3-yl-$C_{1-4}$-alkyl-O, 1-($C_{1-3}$-alkyl)-piperidin-2-yl-$C_{1-4}$-alkyl-O, 1-($C_{1-3}$-alkyl)-piperidin-3-yl-$C_{1-4}$-alkyl-O, 1-($C_{1-3}$-alkyl)-piperidin-4-yl-$C_{1-4}$-alkyl-O, 1-($C_{1-3}$-alkyl)-azepan-2-yl-$C_{1-4}$-alkyl-O, 1-($C_{1-3}$-alkyl)-azepan-3-yl-$C_{1-4}$-alkyl-O, 1-($C_{1-3}$-alkyl)-azepan-4-yl-$C_{1-4}$-alkyl-O, 4-($C_{1-3}$-alkyl)-morpholin-2-yl-$C_{1-4}$-alkyl-O— and 4-($C_{1-3}$-alkyl)-morpholin-3-yl-$C_{1-4}$-alkyl-O, while $R^4$ denotes a group, which may be identical or different, selected from among OH, $C_{1-3}$-alkyl-O, $C_{3-6}$-cycloalkyl-O, $NH_2$, $C_{1-3}$-alkyl-NH, ($C_{1-3}$-alkyl)$_2$N, (2-methoxyethyl)$_2$N, pyrrolidin-1-yl, piperidin-1-yl, azepan-1-yl, morpholin-4-yl, 1,4-oxazepan-4-yl, 2-oxa-5-aza-bicyclo[2,2,1]hept-5-yl, 3-oxa-8-aza-bicyclo[3.2.1]oct-8-yl, 8-oxa-3-aza-bicyclo[3.2.1]oct-3-yl, piperazin-1-yl, 4-($C_{1-3}$-alkyl)-piperazin-1-yl, 1,4-diazepan-1-yl, 4-($C_{1-3}$-alkyl)-1,4-diazepan-1-yl, HCO—NH, $C_{1-4}$-alkyl-CO—NH, $C_{1-3}$-alkyl-O—$C_{1-3}$-alkyl-CO—NH, $C_{1-4}$-alkyl-O—CO—NH, $H_2$NCONH, $C_{1-3}$-alkyl-NH—CO—NH, ($C_{1-3}$-alkyl)$_2$N—CONH, pyrrolidin-1-yl-CO—NH, piperidin-1-yl-CO—NH, piperazin-1-yl-CO—NH, 4-($C_{1-3}$-alkyl)-piperazin-1-yl-CO—NH, morpholin-4-yl-CO—NH— and $C_{1-4}$-alkyl-$SO_2$—NH, while the pyrrolidinyl, piperidinyl, azepan-1-yl, piperazinyl, 1,4-diazepan-1-yl, morpholinyl- and 1,4-oxazepan-4-yl groups mentioned above in the definition of the group $R^d$ may each additionally be substituted by one or two $C_{1-3}$-alkyl groups, and wherein the above-mentioned phenyl groups are mono- or disubstituted by groups $R^5$, wherein $R^5$ denotes hydrogen, or a group, which may be identical or different, selected from among F, Cl, Br, I, OH, CN, $C_{1-3}$-alkyl, $C_{1-3}$-alkyl-O, $CHF_2$, $CF_3$, —O—$CHF_2$ and —O—$CF_3$, and unless stated otherwise, the above-mentioned alkyl groups may be straight-chain or branched, A denotes a $C_2$-alkylene group wherein the $C_2$-alkylene group may be 1-, 2-, 3- or 4-substituted by a group $R^6$, and $R^6$ which may be identical or different, denotes hydrogen, or a group selected from among OH, $C_1$-$C_4$-alkyl and —O—$C_1$-$C_4$-alkyl optionally in the form of the tautomers, the racemates, the enantiomers, the diastereomers and the mixtures thereof, or a pharmacologically acceptable acid addition salt thereof.

2. The method according to claim 1, wherein the disease is chronic obstructive bronchitis (COPD) or asthma.

3. The method according to claim 1, wherein the compound of formula (I) is

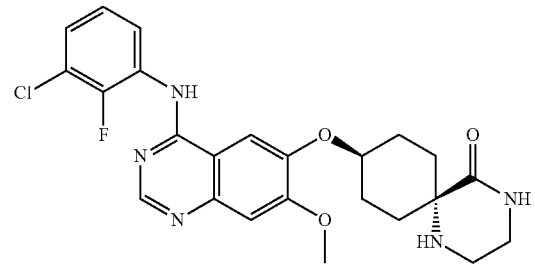 [SMILES: COc1cc2ncnc(Nc3cccc(Cl)c3F)c2cc1O[C@H]1CC[C@@]2(CC1)NCCNC2=O]

or a pharmacologically acceptable acid addition salt thereof.

4. The method according to claim 1, wherein the compound of formula (I) is

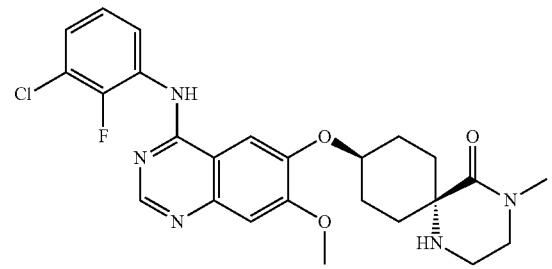 [SMILES: COc1cc2ncnc(Nc3cccc(Cl)c3F)c2cc1O[C@H]1CC[C@@]2(CC1)NCCN(C)C2=O]

or a pharmacologically acceptable acid addition salt thereof.

5. The method according to claim 1, wherein the compound of formula (I) is

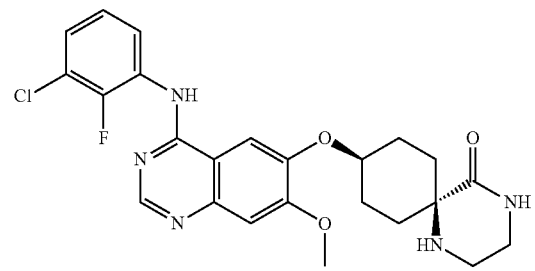 [SMILES: COc1cc2ncnc(Nc3cccc(Cl)c3F)c2cc1O[C@H]1CC[C@]2(CC1)NCCNC2=O]

or a pharmacologically acceptable acid addition salt thereof.

6. The method according to claim 1, wherein the compound of formula (I) is

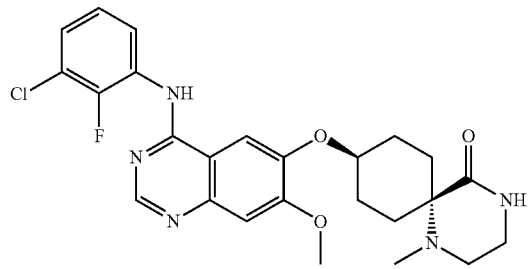 [SMILES: COc1cc2ncnc(Nc3cccc(Cl)c3F)c2cc1O[C@H]1CC[C@]2(CC1)C(=O)NCCN2C]

or a pharmacologically acceptable acid addition salt thereof.

7. The method according to claim 1, wherein the compound of formula (I) is

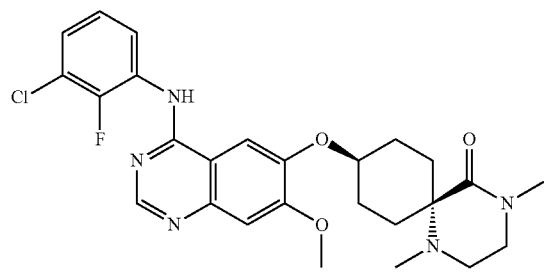 [SMILES: COc1cc2ncnc(Nc3cccc(Cl)c3F)c2cc1O[C@H]1CC[C@]2(CC1)C(=O)N(C)CCN2C]

or a pharmacologically acceptable acid addition salt thereof.

8. The method according to claim 1, wherein the compound of formula (I) is

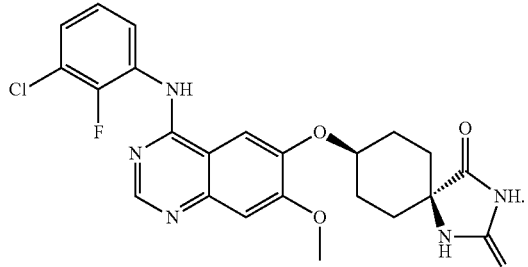

or a pharmacologically acceptable acid addition salt thereof.

9. The method according to claim 1, wherein the compound of formula (I) is

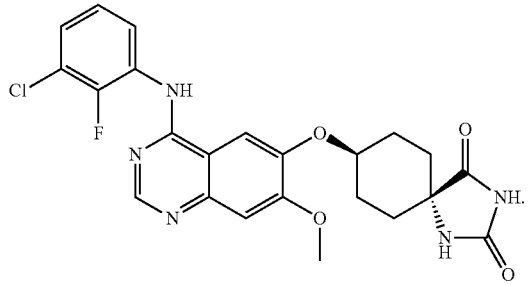 [SMILES: COc1cc2ncnc(Nc3cccc(Cl)c3F)c2cc1O[C@H]1CC[C@@]2(CC1)NC(=O)NC2=O]

or a pharmacologically acceptable acid addition salt thereof.

* * * * *